US009746471B2

(12) United States Patent
Sobol et al.

(10) Patent No.: US 9,746,471 B2
(45) Date of Patent: Aug. 29, 2017

(54) P53 BIOMARKERS

(75) Inventors: Robert E. Sobol, Rancho Santa Fe, CA (US); Kerstin Menander, Bellaire, TX (US)

(73) Assignee: MULTIVIR INC., Houston, TX (US)

( * ) Notice: Subject to any disclaimer, the term of this patent is extended or adjusted under 35 U.S.C. 154(b) by 1786 days.

(21) Appl. No.: 12/863,807

(22) PCT Filed: Jan. 26, 2009

(86) PCT No.: PCT/US2009/032029
§ 371 (c)(1),
(2), (4) Date: Jan. 12, 2011

(87) PCT Pub. No.: WO2009/094647
PCT Pub. Date: Jul. 30, 2009

(65) Prior Publication Data
US 2011/0097389 A1 Apr. 28, 2011

Related U.S. Application Data

(60) Provisional application No. 61/023,736, filed on Jan. 25, 2008, provisional application No. 61/030,874, filed on Feb. 22, 2008, provisional application No. 61/044,373, filed on Apr. 11, 2008.

(51) Int. Cl.
| | | |
|---|---|---|
| *A61K 31/713* | (2006.01) | |
| *G01N 33/574* | (2006.01) | |
| *G01N 33/68* | (2006.01) | |
| *C07K 14/47* | (2006.01) | |

(52) U.S. Cl.
CPC ....... *G01N 33/574* (2013.01); *C07K 14/4746* (2013.01); *G01N 33/6875* (2013.01); *G01N 2800/52* (2013.01)

(58) Field of Classification Search
USPC ..................... 424/93.2; 514/44 R; 435/320.1
See application file for complete search history.

(56) References Cited

U.S. PATENT DOCUMENTS

| | | | |
|---|---|---|---|
| 5,747,469 A * | 5/1998 | Roth et al. .................. 514/44 R |
| 6,740,320 B1 * | 5/2004 | Zhang et al. ................. 424/93.2 |
| 6,797,702 B1 * | 9/2004 | Roth et al. .................. 514/44 R |
| 6,805,858 B1 * | 10/2004 | Zhang et al. ................. 424/93.2 |
| 7,109,179 B2 * | 9/2006 | Roth et al. .................. 514/44 R |
| 2003/0012770 A1 * | 1/2003 | Zhang et al. ................. 424/93.2 |
| 2005/0227918 A1 | 10/2005 | Farrell et al. ................. 514/18.9 |
| 2006/0074565 A1 | 4/2006 | Miller et al. .................... 702/20 |

FOREIGN PATENT DOCUMENTS

| | | |
|---|---|---|
| WO | WO 2005-080593 | 9/2005 |
| WO | WO 2007/090125 | 1/2007 |

OTHER PUBLICATIONS

Trkova et al. Analysis of genetic events in 17p13 and 9p21 regions supports predominant monoclonal origin of multifocal and recurrent bladder cancer Cancer Letters vol. 242, Issue 1, Oct. 8, 2006, pp. 68-76.*

Gabrilovich et al Drug Evaluation INGN 201 (Advexin®): adenoviral p53 gene therapy for cancer Aug. 2006, vol. 6, No. 8 , pp. 823-832.*
St john et al., Cancer Gene Therapy [2000, 7(5):749-756]Endogenous p53 gene status predicts the response of human squamous cell carcinomas to wild-type p53.*
Michor et al. Nature Reviews. 4:197-206; 2004.*
Roth and Cristiano J. Natl. Cancer Inst. 89:21-39; 1997.*
BioDrugss 2003; pp. 216-222.*
P53 From Wikipedia, the free encyclopedia Last visited Nov. 12, 2013.*
Zhang et al., High-efficiency gene transfer and high-level expression of wild-type p53 in human lung cancer cells mediated by recombinant adenovirus. Cancer Gene Ther. Mar. 1994;1(1):5-13. (abstract).*
European Search Report issued in Application No. 09703365, dated May 26, 2011.
Menander et al., "Identification of a predictive molecular biomarker of p53 therapy (adenoviral p53) in patients with recurrent squamous cell carcinoma of the head and neck," abstract presented in *Proceedings of the Annual Meeting of the American Association for Cancer Research*,48:1-2, 2007.
Nemunaitis et al., "Biomarkers predict p53 gene therapy efficacy in recurrent squamous cell carcinoma of the head and neck," *Molecular Therapy, 12th Annual Meeting of the American Society of Gene Tehrapy*; 17, S139, 2009.
Nemunaitis et al., "Biomarkers predict p53 gene therapy efficacy in recurrent squamouc cell carcinoma of the head and neck," *Clinical Cancer Research*, 15:7719-7725, 2009.
Sobol et al., "Biomarkers predict 53 gene therapy efficacy in recurrent squamous cell carcinoma of the head and neck," abstract presented in *Proceedings of the Annual Meeting of the American Association for Cancer Research*, 50:1-2, 2009.
Boulay et al., "P21 gene expression as an indicator for the activity of adenovirus-p53 gene therapy in non-small cell lung cancer patients," *Cancer Gene Therapy*, 7(9):1215-1219, 2000.
Cascallo et al., "Genetic background determines the response to adenovirus-mediated wild-type p53 expression in pancreatic tumor cells," *Cancer Gene Therapy*, 6(5):428-436, 1999.
Clayman et a!., "Adenovirus-mediated p53 gene transfer in patients with advanced recurrent head and neck squamous cell carcinoma," *Journal of Clinical Oncology*, 16(6):2221-2232, 1998.
De Vries, "Targeted point mutations of p53 lead to dominant-negative inhibition of wild-type p53 function," *PNAS*, 99(5):2948-2953, 2002.
Gallo et al., "p53 oncoprotein expression in parotid gland carcinoma is associated with clinical outcome," *Cancer*, 75: 2037-2044, 1995.
Geisler et al., "p16 and p53 Protein Expression as Prognostic Indicators of Survival and Disease Recurrence from Head and Neck Cancer," *Clin. Cancer Res.*, 8:3445-3453, 2002.
George et al., "p53 gene and protein status: the role of p53 alterations in predicting outcome in patients with bladder cancer," *Journal of Clinical Oncology*, 25(34):5352-5358, 2007.

(Continued)

*Primary Examiner* — Maria Leavitt
(74) *Attorney, Agent, or Firm* — Parker Highlander PLLC

(57) ABSTRACT

The present invention relates to the identification of p53 biomarker profiles that predict response in patients with hyperproliferative disease such as cancer to a therapy, and their use in methods of treating such patients with an anti-hyperproliferative disease gene therapy.

10 Claims, 21 Drawing Sheets

(56) References Cited

OTHER PUBLICATIONS

Figure 1:
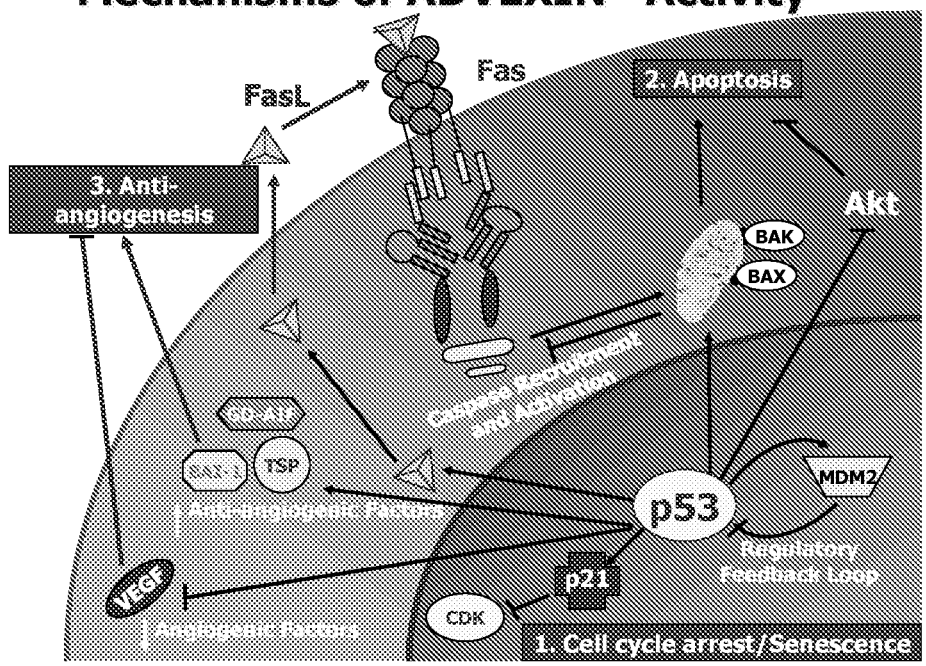

Harris et al., "Adenovirus-mediated p53 gene transfer inhibits growth of human tumor cells expressing mutant p53 protein," *Cancer Gene Therapy*, 3(2): 121-130, 1996.
Karlsson et al., "Sequential broadening of ctl responses in early HIV-1 infection is associated with viral escape," *PLoS One*, 2(2):e225, 17 pages, 2007.
Kyzas et al., "Selective reporting biases in cancer prognostic factor studies," *Journal of the National Cancer Institute*, 97(14):1043-1055, 2005.
Lai et al., "Increasing genomic instability during premalignant neoplastic progression revealed through high resolution array-CGH," *Genes, Chromosomes and Cancer*, 46:532-542, 2007.
Lips et al, "Reliable high-throughput genotyping and loss-of-heterozygosity detection in formalin-fixed, paraffin-embedded tumors using single nucleotide polymorphism arrays," *Cancer Res.*, 65(22):10188-10191, 2005.
Matsumura et al., "p53 and MDM2 expression in oral squamous cell carcinoma," *Oncology*, 53(4):308-312, 1996.
McKaig et al., "Human Papillomavirus and head and neck cancer: Epidemiology and molecular biology," *Head & Neck*, 20(3): 250-265, 1998.
McPake et al., "Wild-type p53 induction mediated by replication deficient adenoviral vectors," *Cancer Research*, 59:4247-4251, 1999.
Mieog et al., "Tumour response to preoperative anthracycline-based chemotherapy in operable breast cancer: the predictive role of p53 gene expression," *European Journal of Cancer*, 42:1369-1379, 2006.
Mulder et al., "Evaluation of p53 protein expression as a marker for long-term prognosis in colorectal carcinoma," *Br. J. Cancer*, 71:1257-1262, 1995.
Nemunaitis et al., "Recombinant granulocyte-macrophage colony-stimulating factor after autologous bone marrow transplantation for lymphoid cancer," 324(25): 1773-1778, 1991.
Olivier et al., "The clinical value of somatic TP53 gene mutations in 1,794 patients with breast cancer," *Clin. Cancer Res.*, 12(4):1157-1167, 2006.
Poeta et al., "TP53 mutations and survival in squamous-cell carcinoma of the head and neck," *The New England Journal of Medicine*, 357:2252-2261, 2007.
Recondo at al., "Recurrent and/or metastatic head and neck squamous cell carcinoma: A clinical, univariate and multivariate analysis of response and survival with cisplatin-based chemotherapy," *Laryngoscope*, 101(5):494-501, 1991.
Resnick and Inga, "Functional mutants of the sequence-specific transcription factor p53 and implications for master genes of diversity," *PNAS*, 100(17):9934-9939, 2003.
Sarkis et al., "Prognostic value of p53 nuclear overexpression in patients with invasive bladder cancer treated with neoadjuvant MVAC," *Journal of Clinical Oncology*, 13:1384-1390, 1995.
Sauter et al., "p53 correlates with improved survival in patients with esophageal adenocarcinoma," *J. Surgical Oncology*, 58(4):269-273, 1995.
Senzer et aL, "p53 therapy in a patient with Li-Fraumeni syndrome," *Mol. Cancer Ther.* 6(5):1478-1482,2007.
Souissi et al., "Locus-specific mutation databases: pitfalls and good practice based on the p53 experience," *Nature Reviews Cancer*, 6:83-90, 2006.
St. John et al., "Endogenous p53 gene status predicts the response of human squamous cell carcinomas to wild-type," *Cancer Gene Therapy*, 7(5):749-756, 2000.
Stenmark-Askmalm et al., "p53 as a prognostic factor in stage I breast cancer," *British Journal Cancer*, 72(3):715-719, 1995.
Trkova et al., "A Li-Fraumeni syndrome family with retained heterozygosity for a germline TP53 mutation in two tumors," *Cancer Genetics and Cytogenetics*, 145:60-64, 2003.
Valentin-Vega et al., "High levels of the p53 inhibitor MDM4 in head and neck squamous carcinomas," *Human Pathology*, 38(10):1553-1562, 2007.
Wen et al., "Development and validation of sensitive assays to quantitative gene expression after p53 gene therapy and palitaxel chemotherapy using in vivo dosing in tumor xenograft models," *Cancer Gene Therapy*, 7(11):1469-1480, 2000.
Soussi et al., "Assessing TP53 status in human tumors to evaluate clinical outcome," *Nature Reviews Cancer*, 1:1-8, 2001.
International Search Report, issued in International Application No. PCT/US2009/032029, mailed Jul. 29, 2009.
International Preliminary Report on Patentability, issued in International Application No. PCT/US2009/032029, mailed on Jul. 27, 2010.
Lang et al., "Enhancement of radiosensitivity of wild-type p53 human glioma cells by adenovirus-mediated delivery of the p53 gene," *J. Neurosurg.*, 89(1):125-32, 1998.
Office Communication issued in Canadian Patent Application No. 2,713,232, dated Nov. 8, 2016.
Office Communication issued in Chinese Patent Application No. 200980108333.3 dated Apr. 2, 2013. (English translation thereof).
Office Communication issued in Mexican Patent Application No. MX/a/2010/008168, dated Dec. 14, 2012. (English summary thereof).
"INGN 201: Ad-p53, Ad5CMV-p53, adenoviral p53, p53 gene therapy—introgen, RPR/INGN 201," *Drugs R D.*, 8(3):176-187, 2007. (Abstract).
Office Communication issued in Canadian Patent Application No. 2,713,232, dated Jan. 20, 2016.

* cited by examiner

P53 BIOMARKERS

This application is a national phase application under 35 U.S.C. §371 of International Application No. PCT/US2009/032029 filed Jan. 26, 2009 which claims the benefit of priority to U.S. Provisional Application Ser. No. 61/023,736, filed Jan. 25, 2008, U.S. Provisional Application Ser. No. 61/030,874, filed Feb. 22, 2008, and U.S. Provisional Application Ser. No. 61/044,373, filed Apr. 11, 2008, the entire contents of all are hereby incorporated by reference.

BACKGROUND OF THE INVENTION

I. Field of the Invention

The present invention relates generally to the fields of oncology and cancer therapy. More particularly, it concerns the assessment of factors to predict the efficacy of an anti-hyperproliferative disease therapy.

II. Description of Related Art

Cancer is a leading cause of death in most countries, and the result of billions of dollars in healthcare expense around the world. It is now well established that a variety of cancers are caused, at least in part, by genetic abnormalities that result in either the overexpression of cancer causing genes, called "oncogenes," or from loss of function mutations in protective genes, often called "tumor suppressor" genes. An example is p53—a 53 kD nuclear phosphoprotein that controls cell proliferation. Mutations to the p53 gene and allele loss on chromosome 17p, where this gene is located, are among the most frequent alterations identified in human malignancies. The p53 protein is highly conserved through evolution and is expressed, albeit at low levels, in most normal tissues. Wild-type p53 has been shown to be involved in control of the cell cycle (Mercer, 1992), transcriptional regulation (Fields and Jang, 1990; Mietz et al., 1992), DNA replication (Wilcock and Lane, 1991; Bargonetti et al., 1991), and induction of apoptosis (Yonish-Rouach et al., 1991; Shaw et al., 1992).

Various mutant p53 alleles are known in which a single base substitution results in the synthesis of proteins that have quite different growth regulatory properties and, ultimately, lead to malignancies (Hollstein et al., 1991). In fact, the p53 gene has been found to be the most frequently mutated gene in common human cancers (Hollstein et al., 1991; Weinberg, 1991), and mutation of p53 is particularly associated with those cancers linked to cigarette smoke (Hollstein et al., 1991; Zakut-Houri et al., 1985). The overexpression of p53 in breast tumors has also been documented (Casey et al., 1991). Interestingly, however, the beneficial effects of p53 are not limited to cancers that contain mutated p53 molecules. In a series of papers, Clayman et al. (1995) demonstrated that growth of cancer cells expressing wild-type p53 molecules was also inhibited by expression of p53 from a viral vector.

As a result of these findings, considerable effort has been placed into p53 gene therapy. Retroviral delivery of p53 to humans was reported some time ago (Roth et al., 1996). There, a retroviral vector containing the wild-type p53 gene under control of a beta-actin promoter was used to mediate transfer of wild-type p53 into 9 human patients with non-small cell lung cancers by direct injection. No clinically significant vector-related toxic effects were noted up to five months after treatment. In situ hybridization and DNA polymerase chain reaction showed vector-p53 sequences in post-treatment biopsies. Apoptosis (programmed cell death) was more frequent in post-treatment biopsies than in pre-treatment biopsies. Tumor regression was noted in three patients, and tumor growth stabilized in three other patients. Similar studies have been conducted using adenovirus to deliver p53 to human patients with squamous cell carcinoma of the head and neck (SCCHN) (Clayman et al., 1998). Surgical and gene transfer-related morbidities were minimal, and the overall results provided preliminary support for the use of Ad-p53 gene transfer as a surgical adjuvant in patients with advanced SCCHN.

Advances in the understanding of the critical role of abnormal p53 function in tumor proliferation and treatment resistance provided the rationale for developing p53 gene therapies for SCCHN and other cancers (Hartwell and Kastan, 1994; Kastan et al., 1995; Edelman and Nemunaitis, 2003; Ahomadegbe et al., 1995; Ganly et al., 2000; Zhang et al., 1995; Clayman et al., 1995; Clayman et al., 1998; Clayman et al., 1999; Swisher et al., 1999; Nemunaitis et al., 2000; Peng, 2005). For example, ADVEXIN® (Ad5CMV-p53, INGN 201) is comprised of a replication-incompetent adenovirus type 5 vector containing the normal p53 tumor suppressor gene as its therapeutic component.

However, despite gene therapy successes, it is presently unclear why some patients respond to p53 and other therapies while others do not. There remains a need to identify specific patient subsets that will most benefit from this treatment.

Several clinical prognostic factors influencing response to a therapy and survival have been identified in patients with recurrent SCCHN (Argiris et al., 2004; Pivot et al., 2001; Recondo et al., 1991). Molecular biomarkers have more recently been used to predict prognosis. However, with respect to the use of p53 biomarkers to predict prognosis, the field is characterized by conflicting data with some studies indicating the ability of p53 biomarkers to predict outcomes (Recondo et al., 1991; Gallo et al., 1995; Mulder et al., 1995; Sarkis et al., 1995; Sauter et al., 1995; Stenmark-Askmalm et al., 1995; Matsumura et al., 1996; McKaig et al., 1998; Nemunaitis et al., 1991) while others indicate that p53 biomarkers do not predict patient outcomes (Kyzas et al., 2005). In fact, one of the largest studies in head and neck cancers, a meta-analysis combining the results of 42 studies involving 3,388 patients revealed no statistically significant correlation between p53 biomarker status and clinical outcome (Kyzas et al., 2005).

Hence, there is a need to properly define p53 biomarker profiles capable of more reliable prediction of patient outcomes to guide the appropriate use of current therapies and to evaluate the efficacy of new treatments.

SUMMARY OF THE INVENTION

Thus, in accordance with the present invention, there is provided a method of predicting a favorable response to a p53 gene therapy for a human subject having a tumor: (a) determining whether tumor cells of said tumor comprise at least one wild-type p53 allele; and/or (b) determining whether tumor cells of said tumor express p53 protein at a level that is higher than that expressed in normal p53-expressing non-tumor cells.

In certain aspects, the present inventors have determined that tumor cells that (i) comprise at least one wild-type p53 allele, and/or (ii) express a level of p53 protein that is not higher than that expressed in normal p53-expressing non-tumor cells, and/or (iii) express an elevated level of p53 protein, defined as a level that is higher than that expressed in normal p53-expressing non-tumor cells, wherein said p53 protein does not inhibit the function of wild-type p53, then any one of (i) through (iii) would be predictive that such a patient will have a favorable response to the p53 gene therapy. The p53 gene therapy may be a gene therapy comprising using a p53 gene or a gene involved in a p53 pathway, for example, ADVEXIN® (Ad5CMV-p53, INGN 201).

In certain embodiments, if tumor cells are found to (1) not contain at least one wild-type p53 allele, and/or (2) contain two mutant p53 alleles, and/or (3) express a mutant p53 protein at levels higher than that expressed by normal p53-expressing normal cells and such mutant p53 inhibits the function of wild-type p53, for example, mutants that comprise missense point mutations in the DNA binding domain with intact tetramerization regions, then such is indicative of a poor response to the p53 gene therapy. Other types of dominant-negative mutations are known in the art and others may also be identified by functional assays (Resnick et al., 2003). High level expression determined by immunohistology of such dominant-negative mutations are also indicative of a poor response to therapy.

Evaluation of increased levels of p53 may be performed using a variety of techniques, including measuring levels of p53 protein by antibody detection of p53 in a tumor cell (e.g., detectable using an immunoassay such as immunohistochemistry (IHC)). Alternatively, p53 transcripts may be amplified and measured in a cell to evaluate overexpression of or increased levels of p53 using, for example, quantitative PCR or RT-PCR. However, it is anticipated that virtually any test for analysis of p53 may be calibrated, by comparison to p53 detection in a sufficient number of p53-expressing non-tumor cells, for use with the present invention, for example, ELISA, immunoassay, radioimmunoassay (RIA), immunoradiometric assay, fluoroimmunoassay, chemiluminescent assay, bioluminescent assay, gel electrophoresis, Western blot analysis or in situ hybridization assay.

The presence of wild-type p53 allele and mutant gene structure may be determined using in situ hybridization, Northern blotting or nuclease protection or using a variety of genotyping techniques based on hybridization with a plurality of probes, e.g., sequencing, gene arrays or gene chips. Particularly, genomic sequences are amplified in tumor cells of the tumor which may be paraffin-embedded.

The tumor may be a benign tumor growth (e.g., benign prostatic hyperplasia, oral leukoplakia; a colon polyp, an esophageal pre-cancerous growth, or a benign lesion). The tumor may be cancer, such as oral cancer, oropharyngeal cancer, nasopharyngeal cancer, respiratory cancer, a urogenital cancer, a gastrointestinal cancer, a central or peripheral nervous system tissue cancer, an endocrine or neuroendocrine cancer, a hematopoietic cancer, a glioma, a sarcoma, a carcinoma, a lymphoma, a melanoma, a fibroma, a meningioma, brain cancer, oropharyngeal cancer, nasopharyngeal cancer, renal cancer, biliary cancer, prostatic cancer, pheochromocytoma, pancreatic islet cell cancer, a Li-Fraumeni tumor, thyroid cancer, parathyroid cancer, pituitary tumors, adrenal gland tumors, osteogenic sarcoma tumors, multiple neuroendrcine type I and type II tumors, breast cancer, lung cancer, head & neck cancer, prostate cancer, esophageal cancer, tracheal cancer, skin cancer brain cancer, liver cancer, bladder cancer, stomach cancer, pancreatic cancer, ovarian cancer, uterine cancer, cervical cancer, testicular cancer, colon cancer, rectal cancer or skin cancer. For example, the tumor may be squamous cell carcinoma (SCCHN), more specifically, recurrent SCCHN.

Favorable response to the therapy may comprise reduction in tumor size or burden, blocking of tumor growth, reduction in tumor-associated pain, reduction in tumor-associated pathology, reduction in tumor-associated symptoms, tumor non-progression, increased disease free interval, increased time to progression, induction of remission, reduction of metastasis, or increased patient survival. Particularly, "tumor response" may refer to tumor growth control (tumor growth control (TGC) defined by complete (CR) and partial (PR) reductions in size of >50% or Stable Disease (SD); TGC=CR+PR+SD) or reductions in tumor size of >10%.

In certain embodiments, there is also provided a method further defined as comprising the steps of (a) determining whether the tumor cells comprise two wild-type p53 alleles; and, if so, then (b) administering a p53 gene therapy to the subject. In anther embodiment, the method may be defined as comprising the steps of (a) determining whether the tumor cells comprise at least one wild-type p53 allele and whether the tumor cells do not overexpress p53 protein; and, if so, then (b) administering to the subject a p53 gene therapy. In a further embodiment, the method could be defined as comprising the steps of (a) determining whether the tumor cells do not contain a p53 mutant allele; and, if so, then (b) administering to the subject a p53 gene therapy. In a still further embodiment, the method may be defined as comprising the steps of (a) determining whether the tumor cells do not overexpress a p53 mutant protein that inhibit the function of wild-type p53; and, if so, then (b) administering to the subject a p53 gene therapy.

In some other embodiments, the method may be further defined as comprising the steps of (a) determining whether the tumor cells overexpress a p53 protein that does not inhibit the function of wild-type p53; and, if so, then (b) administering to the subject a p53 gene therapy. In anther embodiment, the method may be further defined as comprising the steps of (a) determining whether the tumor cells overexpress a mutant p53 protein and such mutant p53 inhibits the function of wild-type p53; and, if so, then (b) administering to the subject a therapy other than p53 therapy. In a further embodiment, the method may be defined as comprising the steps of (a) determining whether the tumor cells do not contain at least one wild-type p53 allele; and, if so, then (b) administering to the subject a therapy other than p53 therapy. In a still further embodiment, the method may be defined as comprising the steps of (a) determining whether the tumor cells contain two mutant p53 allele; and, if so, then (b) administering to the subject a therapy other than p53 therapy. The other therapy may be methotrexate.

In certain aspects, the method further comprise a second anti-tumor therapy. The second anti-tumor therapy may be a surgical therapy, chemotherapy, radiation therapy, cryotherapy, hyperthermia treatment, phototherapy, radioablation therapy, hormonal therapy, immunotherapy, small molecule therapy, receptor kinase inhibitor therapy and biological therapies such as monoclonal antibodies, siRNA, antisense oligonucleotides, ribozymes or gene therapy.

The biological therapy may be a gene therapy, such as tumor suppressor gene therapy, a cell death protein gene therapy, a cell cycle regulator gene therapy, a cytokine gene therapy, a toxin gene therapy, an immunogene therapy, a suicide gene therapy, a prodrug gene therapy, an anti-cellular proliferation gene therapy, an enzyme gene therapy, or an anti-angiogenic factor gene therapy.

The tumor suppressor therapy may be APC, CYLD, HIN-1, KRAS2b, p16, p19, p21, p27, p27mt, p53, p57, p73, PTEN, FHIT, Rb, Uteroglobin, Skp2, BRCA-1, BRCA-2, CHK2, CDKN2A, DCC, DPC4, MADR2/JV18, MEN1, MEN2, MTS1, NF1, NF2, VHL, WRN, WT1, CFTR, C-CAM, CTS-1, zac1, ras, MMAC1, FCC, MCC, FUS1, Gene 26 (CACNA2D2), PL6, Beta* (BLU), Luca-1 (HYAL1), Luca-2 (HYAL2), 123F2 (RASSF1), 101F6, or Gene 21 (NPRL2). The pro-apoptotic protein therapy may be mda7, CD95, caspase-3, Bax, Bag-1, CRADD, TSSC3, bax, hid, Bak, MKP-7, PARP, bad, bcl-2, MST1, bbc3, Sax, BIK, or BID. The cell cycle regulator therapy may be an antisense oncogene, an oncogene siRNA, an oncogene single-chain antibody, or an oncogene ribozyme. The cytokine therapy may be GM-CSF, G-CSF, IL-1α, IL-1β, IL-2, IL-3, IL-4, IL-5, IL-6, IL-7, IL-8, IL-9, IL-10, IL-11, IL-12, IL-13, IL-14, IL-15, IL-16, IL-17, IL-18, IL-19, IL-20, IL-21, IL-22, IL-23, IL-24, IL-25, IL-26, IL-27, IL-28, IL-29, IL-30, IL-31, IL-32 IFN-α, IFN-β, IFN-γ, MIP-1α, MIP-1β, TGF-β, TNF-α, TNF-β, or PDGF. The anti-angiogenic therapy may be angiostain, endostain, avastin or an antisense, siRNA, single-chain antibody, or a ribozyme against a pro-angiogenic factor.

The cancer cell may have a normal p53 gene and/or protein structure or an abnormal p53 gene and/or protein structure. For example, the p53 gene may produce a p53 protein which is identical to a wild-type p53 protein. In other embodiments, a mutation may exist in the p53 protein (e.g., a truncation, deletion, substitution, trans-dominant mutation, etc.). The p53 gene may have at least a wild-type p53 allele (i.e., the proper promoter, introns, exons, and orientation is present) or the p53 gene may have a mutant allele (e.g., a missense, deletion, substitution, rearrangement, etc.).

In certain embodiments, the gene therapy may be delivered by a non-viral vector. The non-viral vector may be entrapped in a lipid vehicle (e.g., a liposome). The vehicle may be a nanoparticle. The gene therapy may be delivered by a viral vector (e.g., retroviral vector, an adenoviral vector, an adeno-associated viral vector, a pox viral vector, a polyoma viral vector, a lentiviral vector, or a herpesviral vector).

The gene therapy may be a loco-regional gene therapy. The loco-regional gene therapy may comprise a localized gene therapy. The localized gene therapy may comprise direct injection of the tumor, injection of tumor vasculature, regional gene therapy, or administration into a tumor-associated lymph vessel or duct. The administration may comprise intraperitoneal, intrapleural, intravesicular, or intrathecal administration. The regional gene therapy may comprise administration into the vasculature system of a limb associated with the tumor.

Certain embodiments also include a kit comprising a p53 antibody or probes for detecting an amount of p53 protein in a tumor sample and a plurality of probes for determining a p53 gene or transcript structure. The kit is used to determine whether tumor cells comprises at least one wild-type p53 allele and whether tumor cells of the same tumor express p53 protein at a level that is higher than that expressed in normal p53-expressing non-tumor cells for prediction of favorable response to a p53 gene therapy.

"p53" as used herein, refers to a wild-type or mutant (e.g., trans-dominant, missense, etc.) p53 protein.

It is contemplated that any method or composition described herein can be implemented with respect to any other method or composition described herein.

The use of the word "a" or "an" when used in conjunction with the term "comprising" in the claims and/or the specification may mean "one," but it is also consistent with the meaning of "one or more" or "at least one." The term "about" means, in general, the stated value plus or minus 5%. The use of the term "or" in the claims is used to mean "and/or" unless explicitly indicated to refer to alternatives only or the alternative are mutually exclusive, although the disclosure supports a definition that refers to only alternatives and "and/or."

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will be apparent to those skilled in the art from this detailed description.

DETAILED DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1—Mechanisms of ADVEXIN® (Ad5CMV-p53, INGN 201) Activity.

Figure 2:
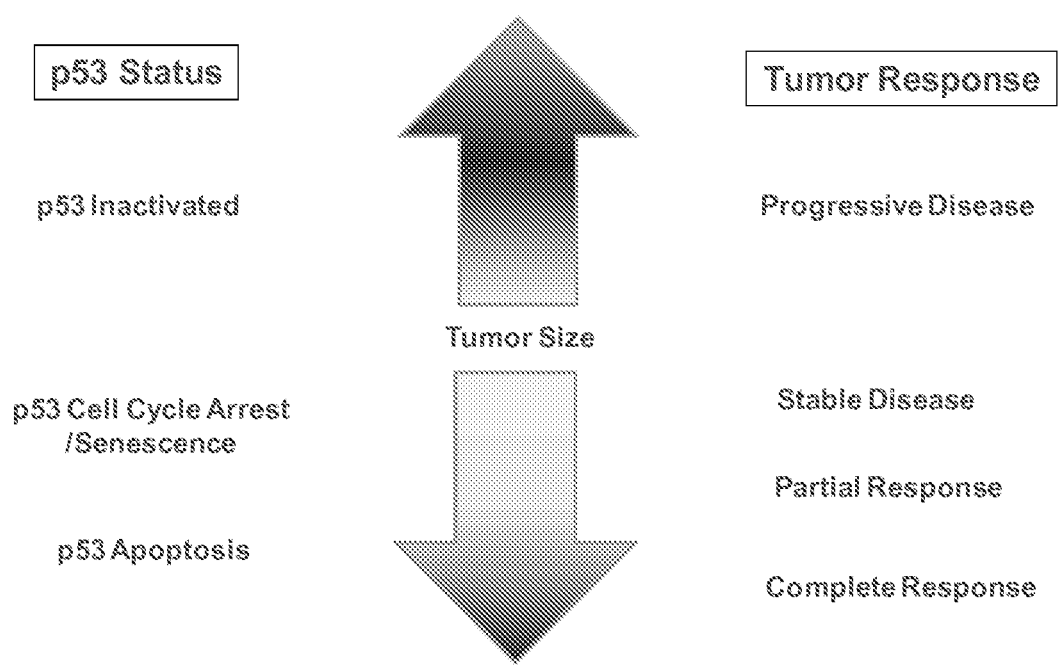

FIG. 2—Spectrum of Anti-Tumor Responses to ADVEXIN® (Ad5CMV-p53, INGN 201) Therapy.

Figure 3:
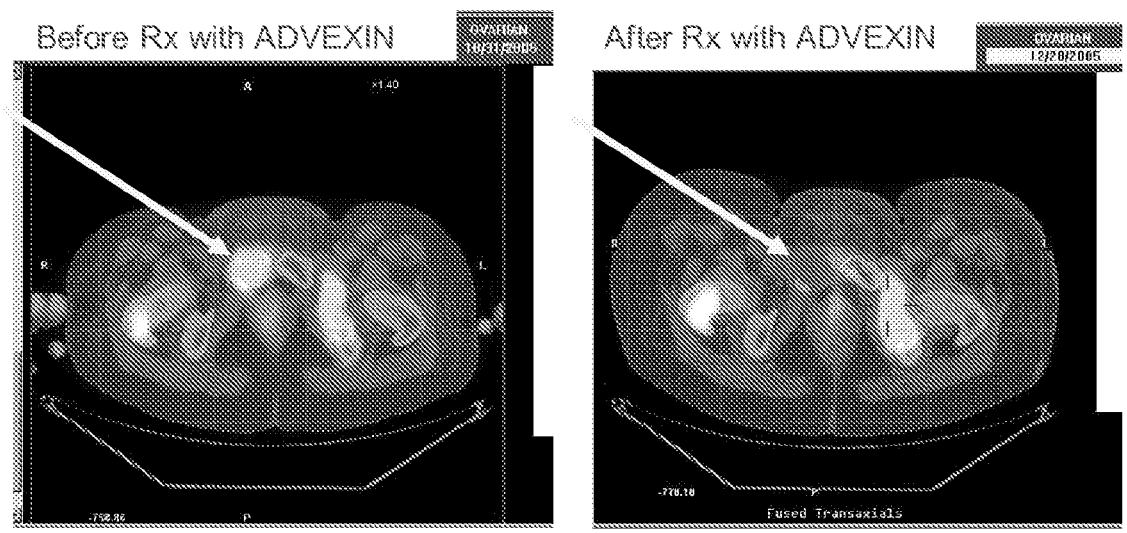

FIG. 3—Senescence/Stable Disease Response in Li-Fraumeni Tumor Following ADVEXIN® (Ad5CMV-p53, INGN 201) Therapy. Complete remission by PET scan of pelvic tumor in a Li-Fraumeni patient following ADVEXIN® (Ad5CMV-p53, INGN 201) therapy of injected tumor (arrow). Concomitant CT scans revealed stable disease without reduction of tumor. Clinically, tumor response was associated with decreased pelvic pain and lower extremity edema (Senzer, 2007).

Figure 4:
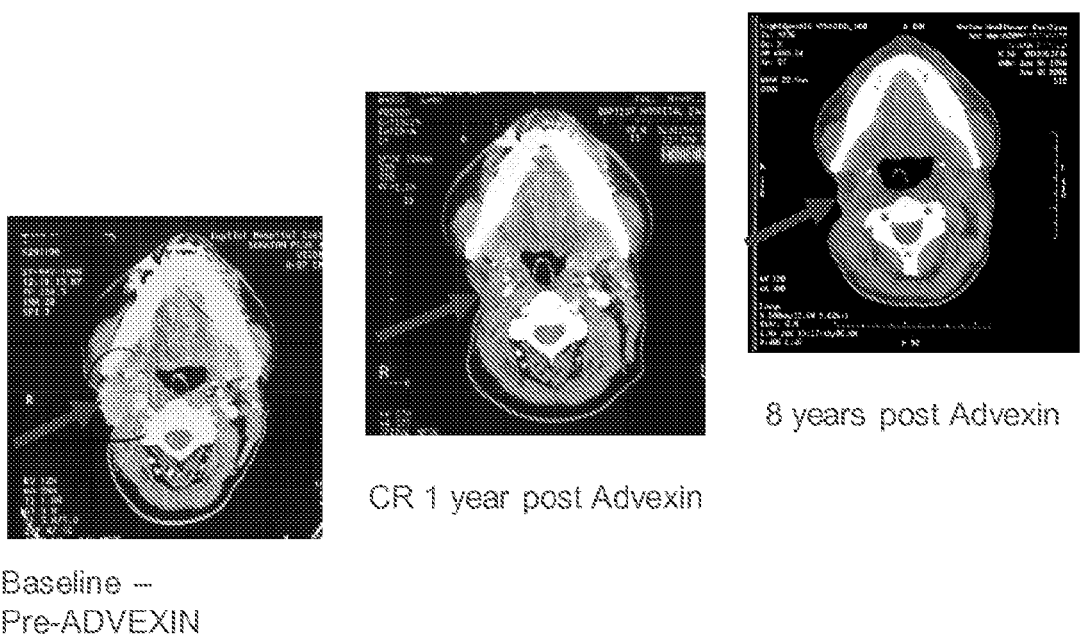

FIG. 4—Apoptosis/Tumor Reduction Response in a Recurrent Head & Neck Tumor Following ADVEXIN® (Ad5CMV-p53, INGN 201) Therapy. Reduction of tumor size with complete remission by CT scan in recurrent SCCHN following ADVEXIN® (Ad5CMV-p53, INGN 201) therapy of injected tumor (arrow).

Figure 5:
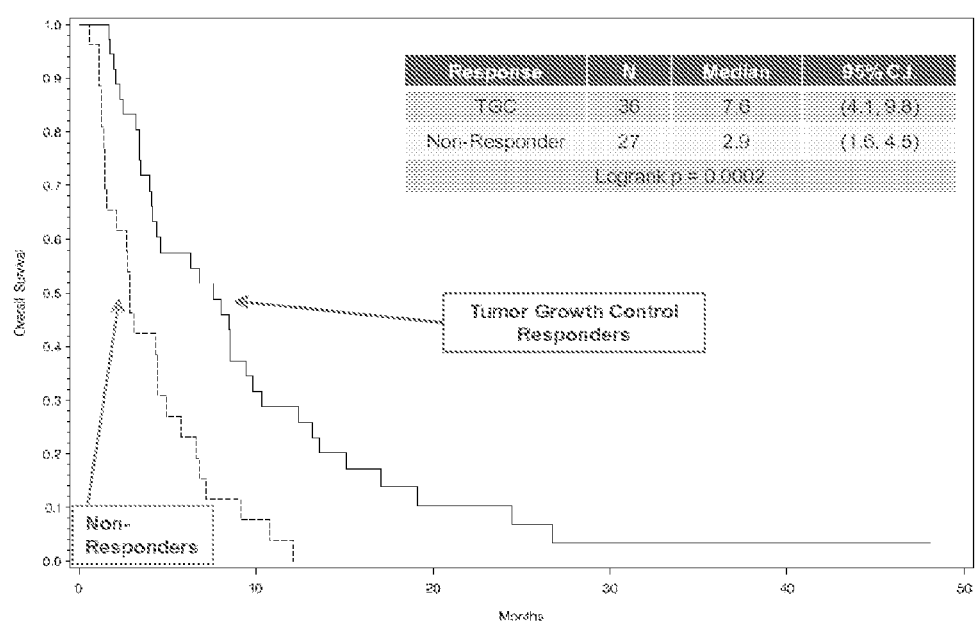

FIG. 5—Correlation of Tumor Growth Control with Increased Survival Following ADVEXIN® (Ad5CMV-p53, INGN 201) Monotherapy—ITT Population T301.

Figure 6:
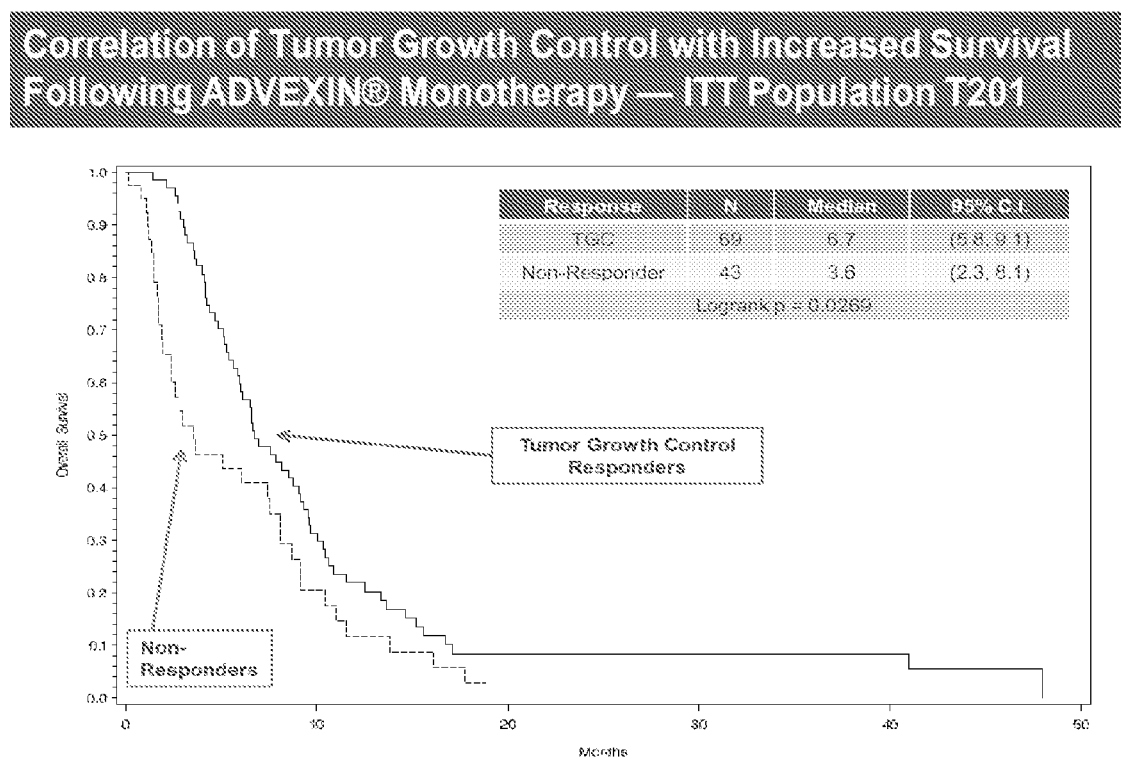

FIG. 6—Correlation of Tumor Growth Control with Increased Survival Following ADVEXIN® (Ad5CMV-p53, INGN 201) Monotherapy—ITT Population T201.

Figure 7:
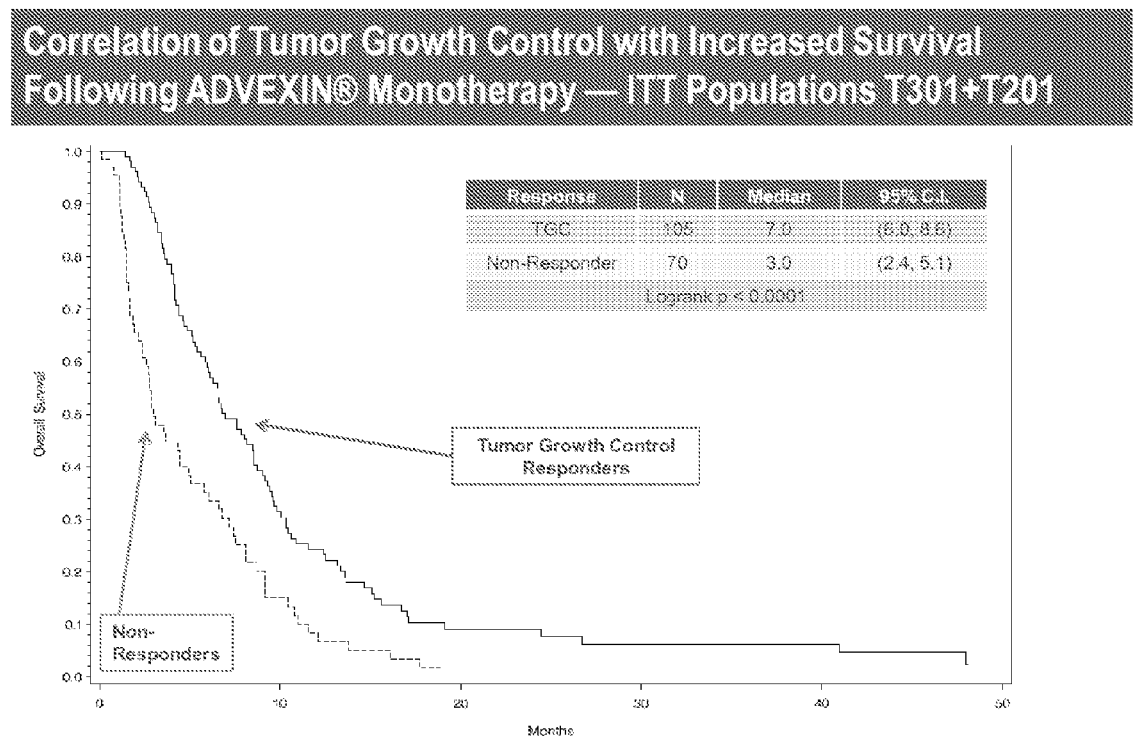

FIG. 7—Correlation of Tumor Growth Control with Increased Survival Following ADVEXIN® (Ad5CMV-p53, INGN 201) Monotherapy—ITT Populations T301+T201.

Figure 8:
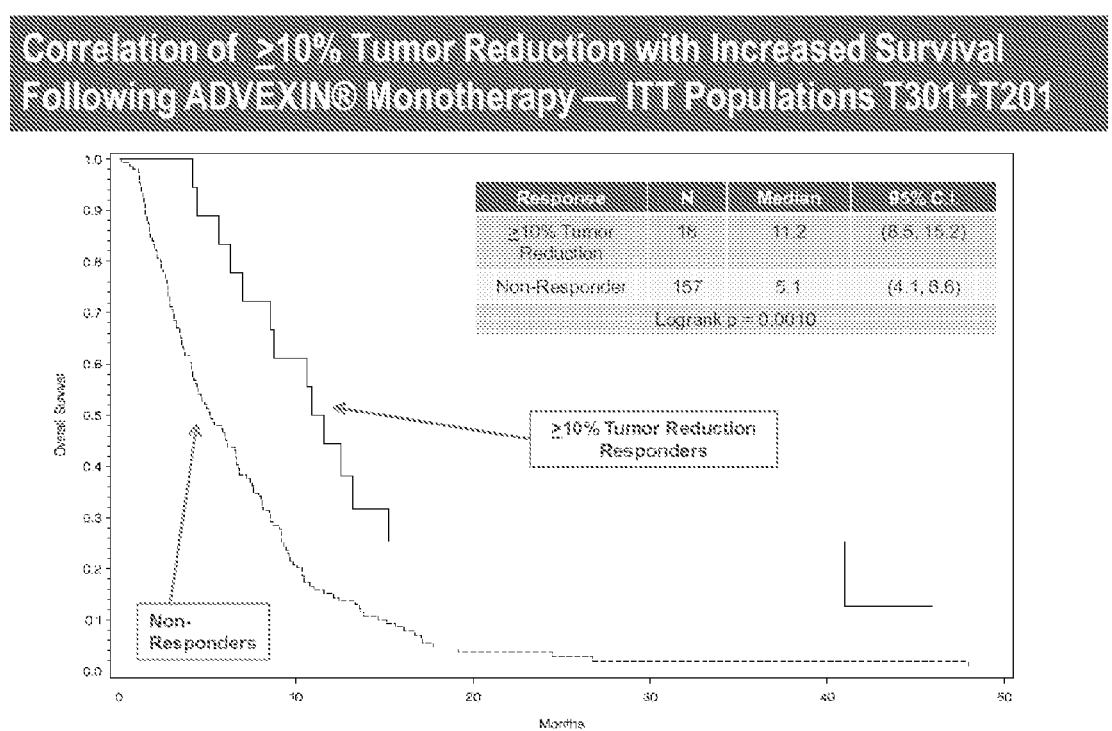

FIG. 8—Correlation of .gtoreq.10% Tumor Reduction with Increased Survival Following ADVEXIN® (Ad5CMV-p53, INGN 201) Monotherapy—ITT Populations T301+T201.

Figure 9:
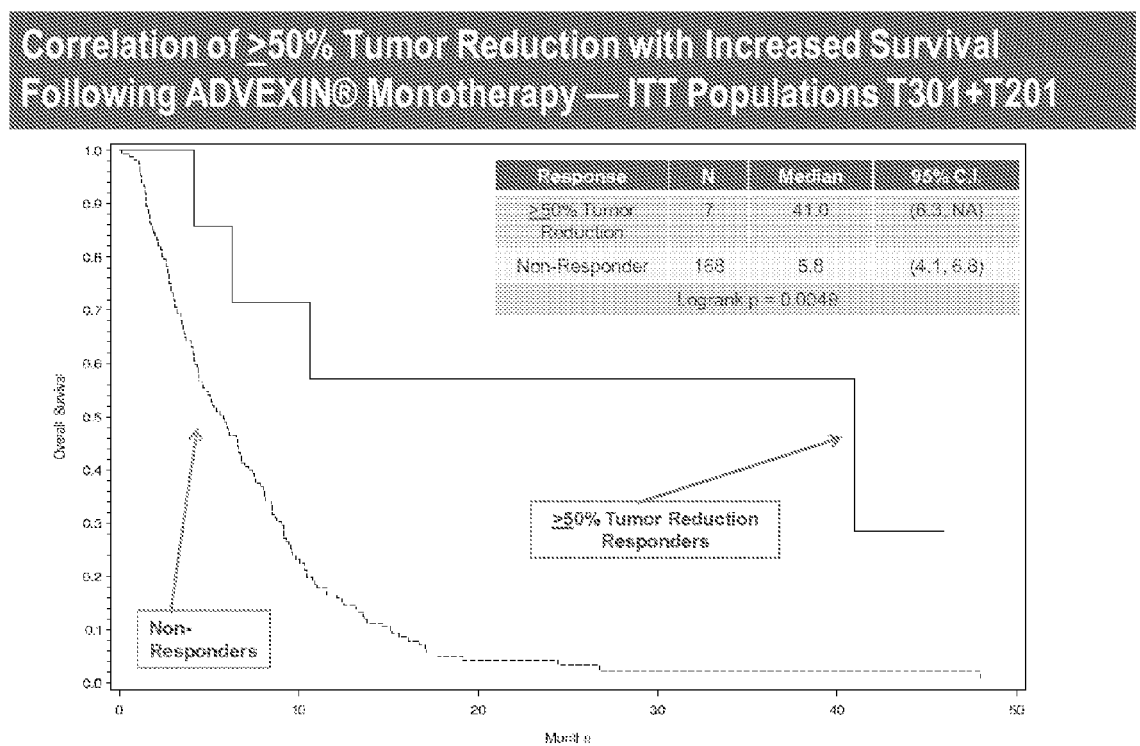

FIG. 9—Correlation of .gtoreq.50% Tumor Reduction with Increased Survival Following ADVEXIN® (Ad5CMV-p53, INGN 201) Monotherapy—ITT Populations T301+T201.

Figure 10:
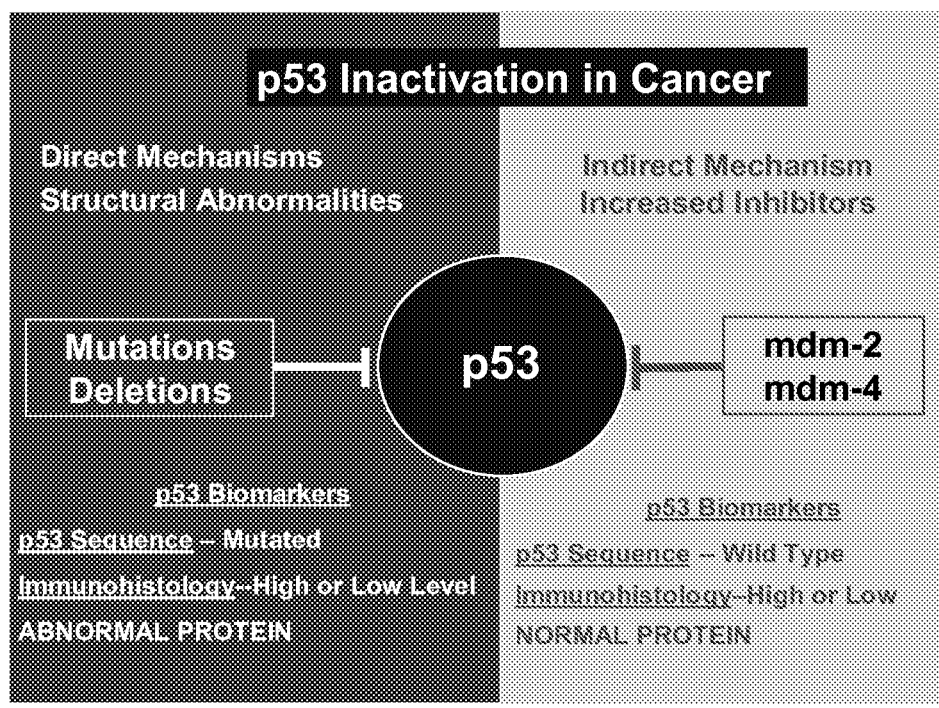

FIG. 10—Mechanisms of p53 Inactivation and Corresponding p53 Sequencing and Immunohistochemistry Biomarker Profiles.

Figure 11:
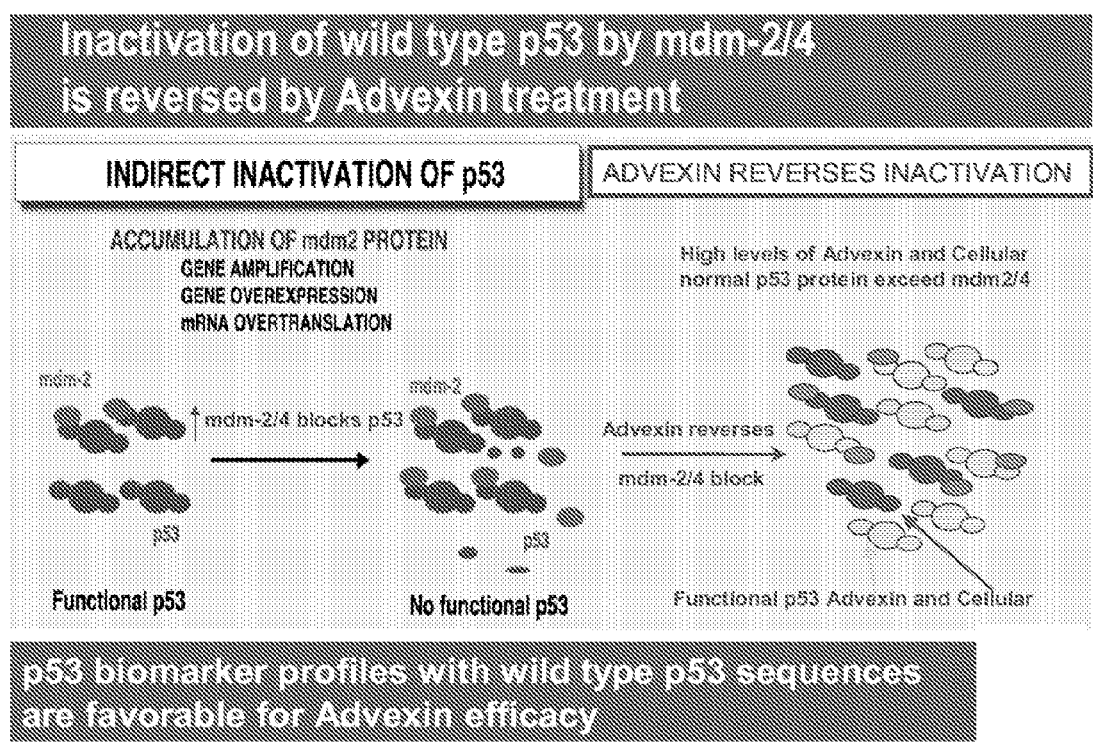

FIG. 11—Inactivation of Wild-Type p53 by mdm-2/4 is Reversed by ADVEXIN® (Ad5CMV-p53, INGN 201) Treatment. In tumors with wild-type p53 sequences, normal endogenous p53 is inactivated by up regulation of the p53 inhibitors mdm-2 and mdm-4. An increased level of normal p53 provided by ADVEXIN® (Ad5CMV-p53, INGN 201) is able to reverse the inhibition of mdm-2/4.

Figure 12:
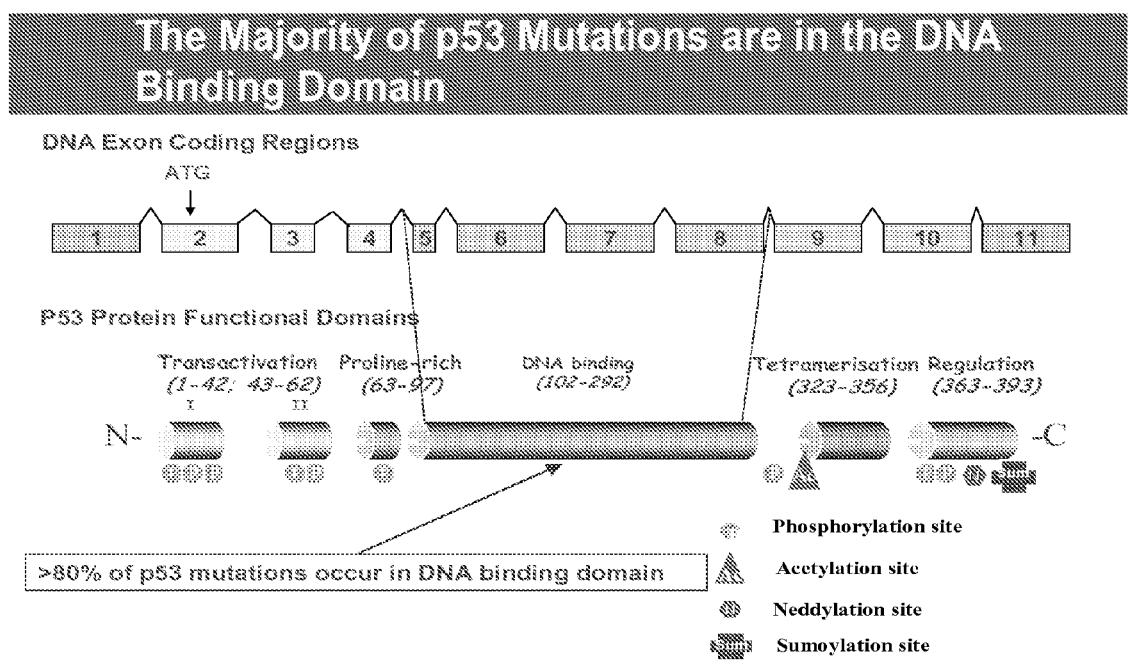

FIG. 12—Majority of p53 Mutations are in the DNA Binding Domain.

Figure 13:
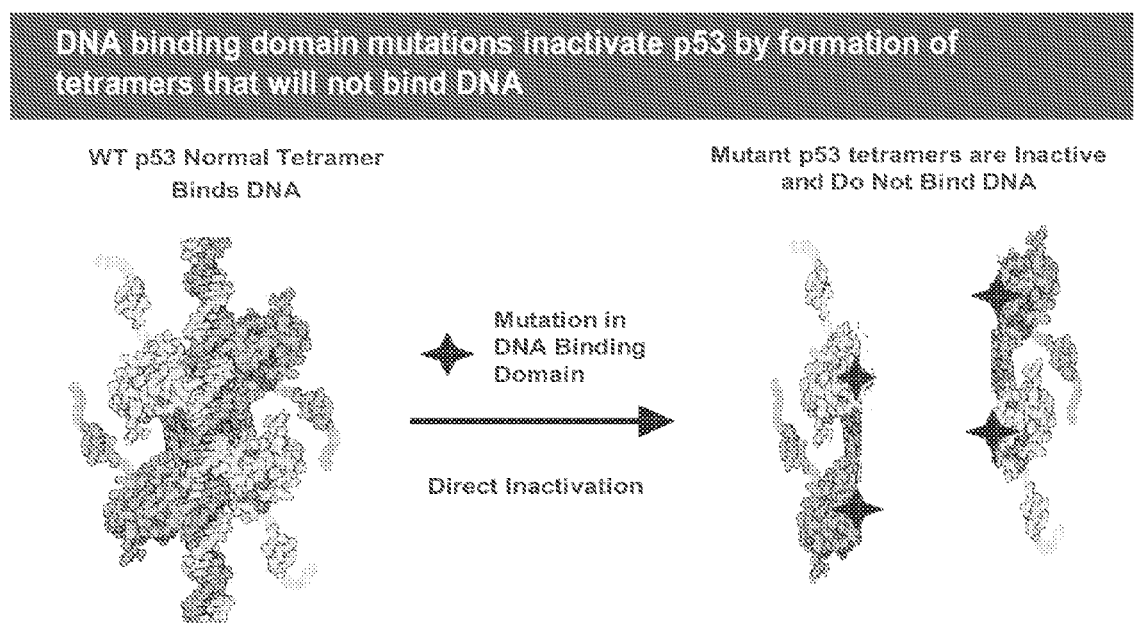

FIG. 13—DNA Binding Domain Mutations Inactivate p53 by Formation of Tetramers That Will Not Bind DNA.

Figure 14:
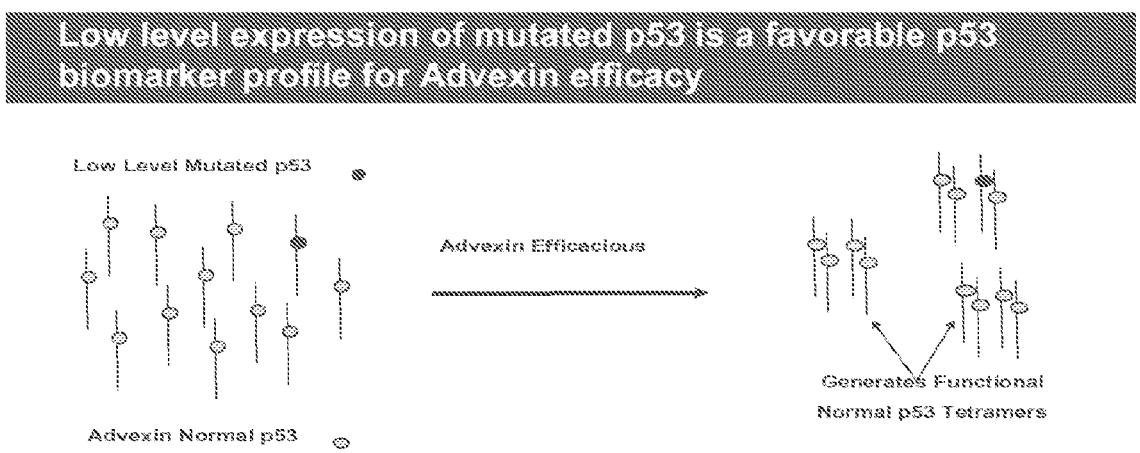

FIG. 14—Low Level Expression of Mutated p53 is a Favorable p53 Biomarker Profile for ADVEXIN® (Ad5CMV-p53, INGN 201) Efficacy.

Figure 15:
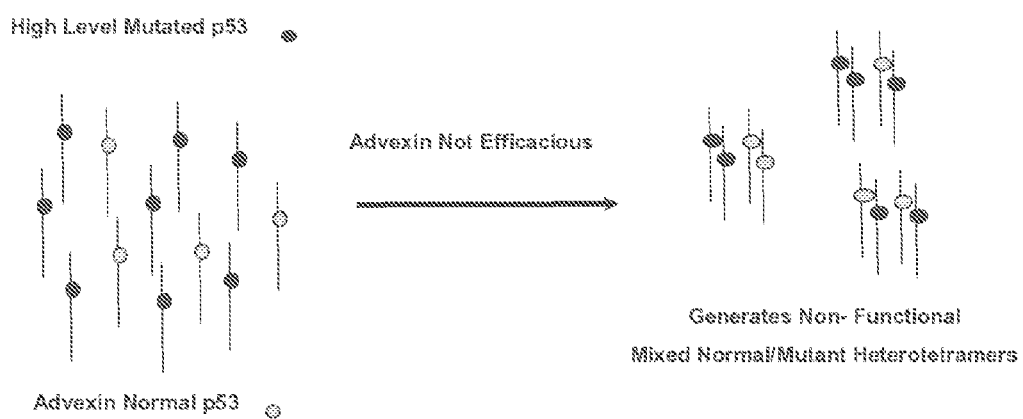

FIG. 15—High Level Mutated p53 Expression is an Unfavorable Dominant-Negative p53 Biomarker Profile for ADVEXIN® (Ad5CMV-p53, INGN 201) Efficacy.

Figure 16:
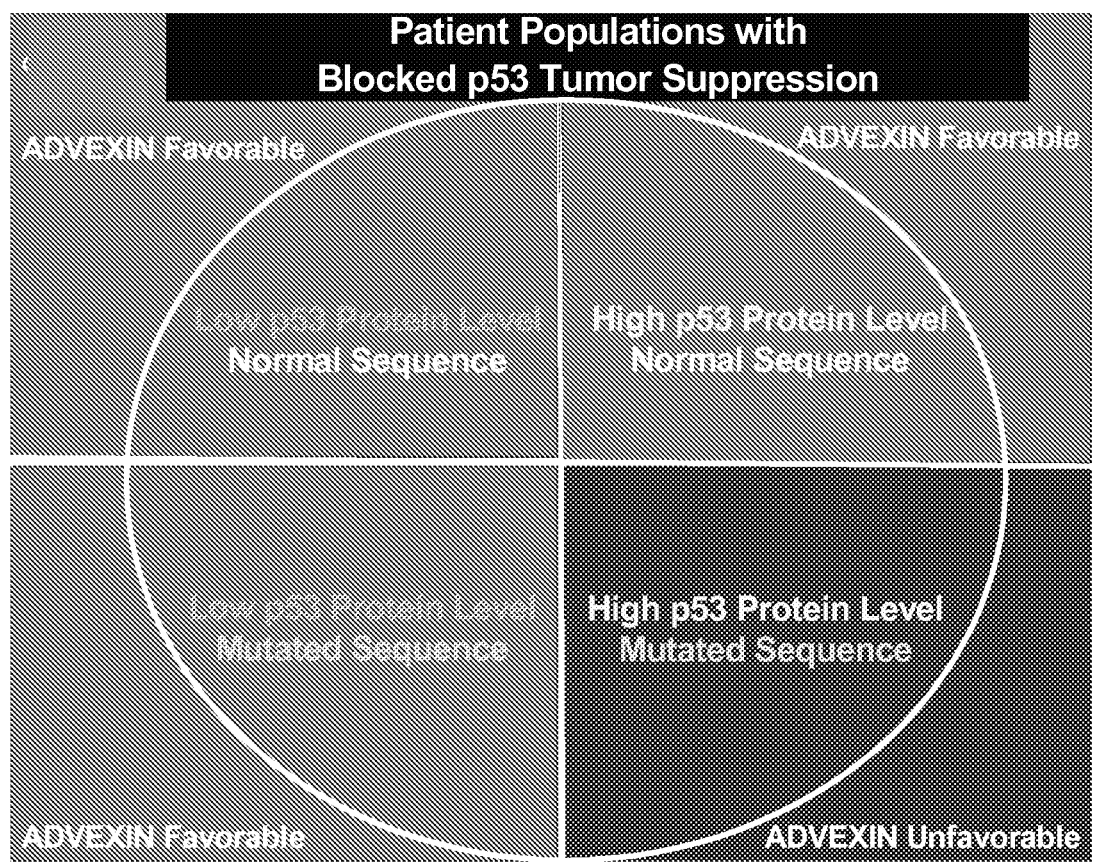

FIG. 16—Patient Populations with Blocked p53 Tumor Suppression.

Figure 17:
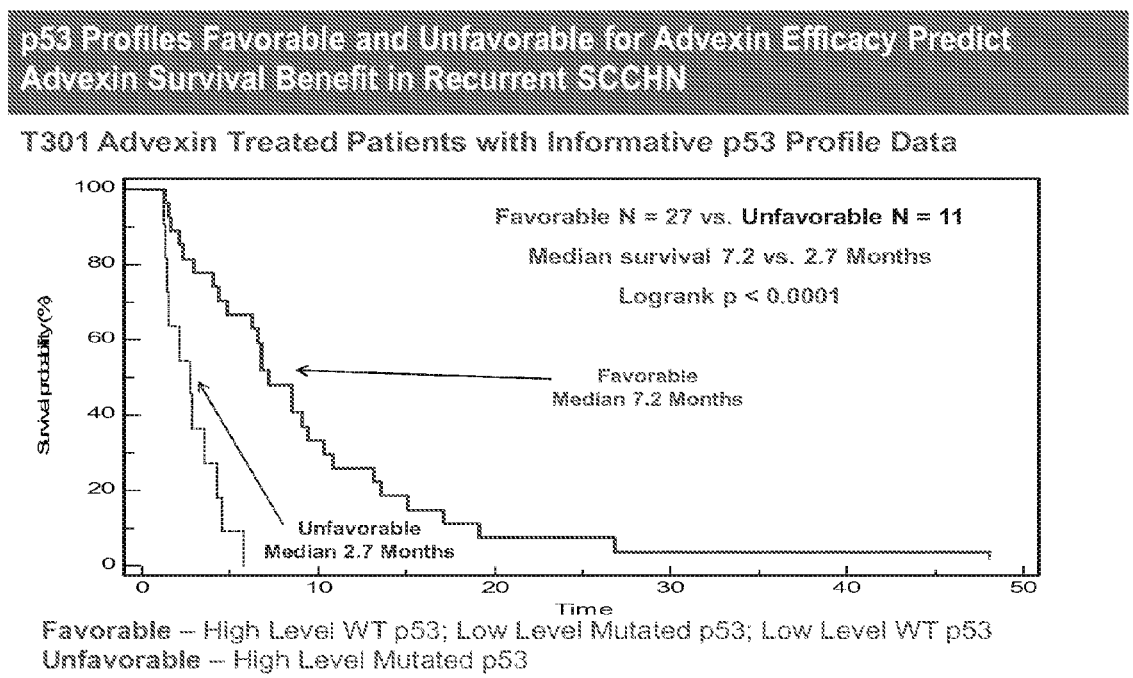

FIG. 17—p53 Profiles Favorable and Unfavorable for ADVEXIN® (Ad5CMV-p53, INGN 201). Efficacy Predict ADVEXIN® (Ad5CMV-p53, INGN 201) Survival Benefit in Recurrent SCCHN Cancer (T301). Favorable—high level wild-type p53; low level mutated p53; low level wild-type p53. Unfavorable—high level mutated p53.

Figure 18:
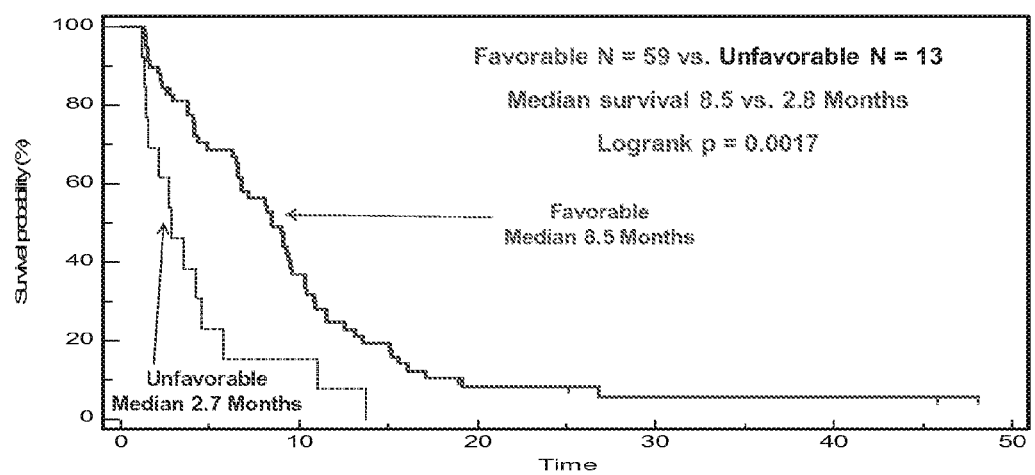

FIG. 18—p53 Profiles Favorable and Unfavorable for ADVEXIN® (Ad5CMV-p53, INGN 201) Efficacy Predict ADVEXIN® (Ad5CMV-p53, INGN 201) Survival Benefit in Recurrent SCCHN Cancer (T301+T201). Favorable—high level wild-type p53; low level mutated p53; low level wild-type p53. Unfavorable—high level mutated p53.

Figure 19:
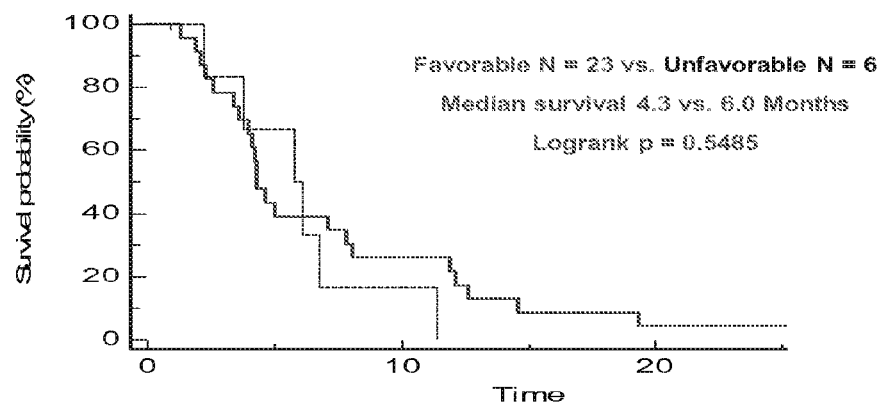

FIG. 19—p53 Profiles Favorable and Unfavorable for ADVEXIN® (Ad5CMV-p53, INGN 201) Efficacy Do Not Predict Methotrexate Outcome in Recurrent SCCHN Cancer. Favorable—high level wild-type p53; low level mutated p53; low level wild-type p53. Unfavorable—high level mutated p53.

Figure 20:
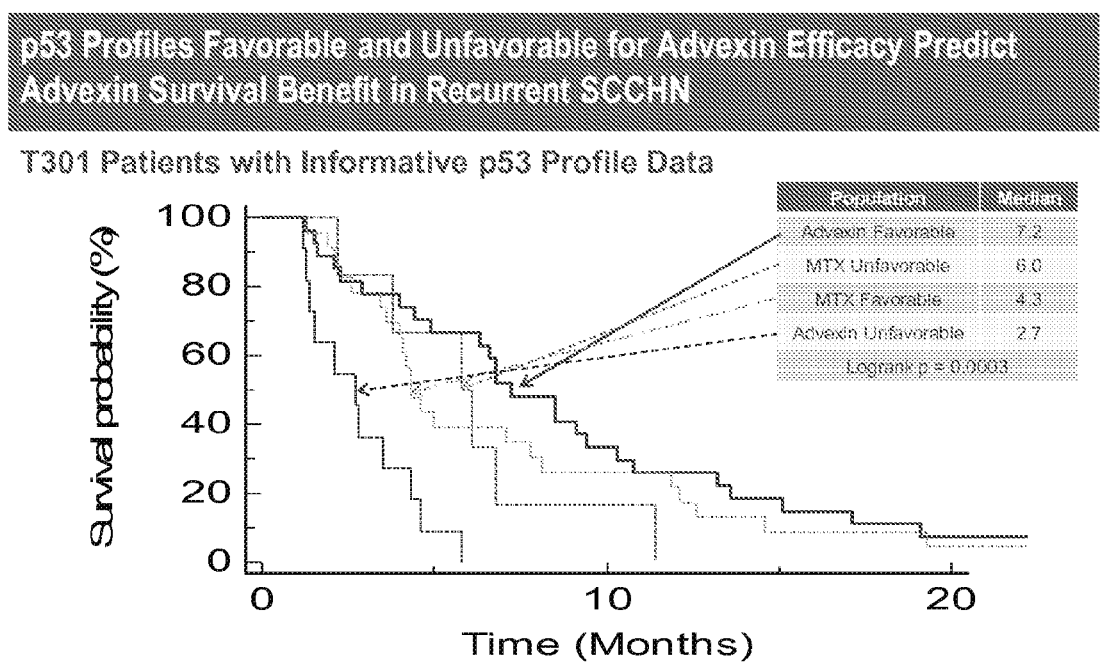

FIG. 20—p53 Profiles Favorable and Unfavorable for ADVEXIN® (Ad5CMV-p53, INGN 201) Efficacy Predict ADVEXIN® (Ad5CMV-p53, INGN 201) Survival Benefit in Recurrent SCCHN Cancer (T301). Favorable—high level wild-type p53; low level mutated p53; low level wild-type p53. Unfavorable—high level mutated p53.

Figure 21:
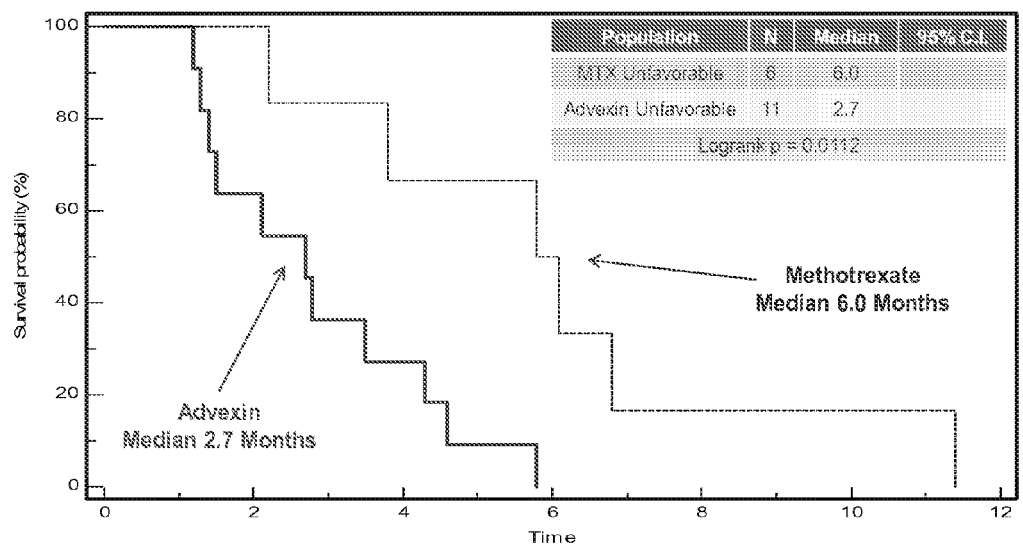

FIG. 21 Methotrexate is Efficacious in Patients With p53 Profiles Unfavorable for ADVEXIN® (Ad5CMV-p53, INGN 201) Efficacy in Recurrent SCCHN Cancer. Favorable—high level wild-type p53; low level mutated p53; low level wild-type p53. Unfavorable—high level mutated p53.

DESCRIPTION OF THE ILLUSTRATIVE EMBODIMENTS

I. The Present Invention

As discussed herein, gene therapy at the clinical level has been under study for a over a decade, including a number of cancer therapy trials. Overall, the success of this approach has been promising with increased benefits over those seen with traditional therapeutic approaches. However, as with most anti-cancer treatments, there still remains a substantial need to improve the identification of patient populations that may benefit most from the efficacy of gene therapy or other treatments.

The previous evaluation of p53 biomarker profiles are inadequate to fully predict the response of treatment or prognosis because they fail to identify all cases that have a functional normal p53 protein, which is the key to predictive and prognostic determinations. Previous applications teach away from this invention by typically considering detection of either an abnormally elevated p53 protein or p53 gene mutations, but not containing a functional normal p53 protein as a predictive or prognostic marker. The inventors discovered unexpectedly that the correct combination and applications of p53 expression amount and gene mutational status that are required to identify the presence of normal functional p53 protein to predict therapeutic responses to a p53 gene therapy. This unexpected result indicates why prior attempts to utilize p53 immunohistology or sequencing analyses have led to conflicting results regarding the ability of these p53 biomarker profiles to routinely predict treatment responses and prognosis.

Here, the inventors provide a method using p53 biomarker profile combinations to predict the response or degree of benefit to a patient from a cancer therapy. In a particular embodiment, the cancer therapy is a gene therapy, for example, adenoviral p53 gene therapy such as ADVEXIN® (Ad5CMV-p53, INGN 201) therapy.

A. p53 Tumor Biomarker Profile Predicting Response to a p53 Gene Therapy

The inventors discover that the following tumor biomarker combinations typically predict favorable efficacy and prognostic outcomes: (1) high level of normal p53 protein (e.g., immunohistochemistry positive with wild-type p53 sequence); (2) low level of p53 protein (immunohistology negative) with detection of at least one normal allele with one abnormal p53 gene sequence (negative immunohistology may be observed when there is one normal p53 allele and one abnormal allele as described by Trkova et al. (2003)); or (3) low level of normal p53 protein (immunohistology negative with wild-type p53 sequence). Each of these biomarker profiles typically defines a condition where a normal p53 gene is likely to be active. In this regard, a p53 gene therapy that will result in increased expression of the normal p53 gene will contribute to therapeutic efficacy and overcome p53 inactivation mediated by inhibitors like MDM2, MDM4 or low level expression of dominant-negative p53 mutated protein as discussed below. Transduction of cells with replication-deficient adenoviral vector alone could also induce wild-type p53 expression in cells containing a wild-type p53 gene (Mcpake et al., 1999).

Normal p53 gene structure is defined as a p53 gene structure that is identical to that in p53-expressing non-tumor normal cells. Wild-type p53 alleles have the same DNA sequence as those in p53 non-tumor normal cells. Elevated level of p53 protein or overexpression of p53 is defined as a level that is higher than that expressed in normal p53-expressing non-tumor cells. Normal level of p53 protein is defined as a level that is not higher than that expressed in normal p53-non-tumor cells.

1. Elevated p53 Level and Normal p53 Gene Predict Favorable Response

A high level of p53 expression coupled with a normal p53 genotype (consisting of wild-type P53 alleles) indicates the presence of high levels of normal p53. Many of these tumors are known to have elevated levels of MDM2 or MDM4 that inhibits p53 activity (Valentin-Vega et al., 2007). However, Valenitn-Vega et al. (2007) does not teach that this circumstance correlates with any favorable prognostic benefit which is only taught in this invention. The present invention indicates that when these tumors are exposed to therapeutic agents that induce stress responses with further up-regulation of p53 expression or which deliver additional wild-type p53 like ADVEXIN® (Ad5CMV-p53, INGN 201), or which down regulate p53 inhibitors like nutlins, the suppression is overcome and the tumor suppressor pathways are then activated resulting in therapeutic efficacy and therapeutic responses, e.g. reductions in tumor size, etc.

2. Low p53 Level and Normal p53 Gene Predict Favorable Response

Similar circumstances occur when the immunohistological evaluation of p53 reveals a low level of expression with normal p53 gene sequences (consisting of wild-type p53 alleles). These tumors either have no p53 defect or they may have up-regulated p53 inhibitors like MDM2 or MDM4 or possibly other methods to block p53 (Valentin-Vega et al., 2007). However, Valenitn-Vega et al. (2007) does not teach that this circumstance correlates with any favorable prognostic benefit which is only taught in this invention. In patients with low level normal p53 protein expression profiles, the administration of wild-type p53 and/or a p53 gene therapy that results in p53 upregulation of stress responses or down regulates p53 inhibitors like nutlins, will increase expression of normal p53 relative to its suppressors and overcome the p53 inhibitors with resultant therapeutic tumor suppressor effects.

3. Low p53 Level and Abnormal p53 Gene Predict Favorable Response

Poeta (2007), Olivier (2006) and Soussi (2006) teach that the presence of a mutated p53 gene, which can inhibit the action of normal p53, is a circumstance that predicts for poor clinical outcomes. These cases generally have mutations of p53 in the DNA binding domain with intact tetramerization domains that result in the ability of the mutated p53 to bind to and inactivate normal p53. Such mutations are termed dominant-negative p53 mutations or inactivating or blocking mutations. However, their presence alone (as detected by gene sequencing methods) is not sufficient to correctly predict outcome as described by Poeta (2007), Olivier (2006) and Soussi (2006), because they fail to consider the level of such inhibitory protein that effects its ability to inactivate a second normal p53 allele when it is present. In addition to the presence of such inactivating or dominant-negative mutations, the level of its expression is important to determine its effect on normal p53. The instant invention discloses that the presence of an inactivating p53 mutation did not correlate with a poor response to p53 treatment if there was a low level of p53 protein expression.

Trkova et al. (2003) have described that patients with mutated p53 sequences and low p53 levels by immunohistology evaluations often have a second normal p53 gene. However, Trkova et al. (2003) does not teach that this circumstance correlates with any favorable prognostic benefit which is only disclosed by the present invention.

4. High p53 Level and Abnormal p53 Gene

As described above, the presence of a mutated p53 gene alone is not sufficient to predict for poor clinical response to cancer therapy. The present invention discloses that conditions that would either permit or prevent the function of normal p53 are the key factor for predictive and prognostic applications of p53 biomarker profiles by combination of p53 amount and gene sequencing analyses. If these mutations of p53 are expressed at high level and are blocking mutations that can inhibit normal p53 function even if a wild-type p53 gene is present, e.g., dominant-negative mutations in the DNA binding domain with intact tetramerization domains that result in the ability of the mutated p53 to bind to and inactivate normal p53, these cases are more likely associated with poor response to a p53 gene therapy because normal p53 function introduced or induced by the therapy are blocked by a high level of disruptive p53 mutants. These types of mutations comprise approximately 80% of p53 mutations (missense mutations in the DNA binding domain with intact tetramerization capability) and they will be associated with a poor response to treatment when the p53 protein encoded by such mutated p53 genes are expressed at high levels in the tumor cell.

However, in the tumor cells expressing high p53 and mutated p53, if these mutations are mutations that do not inhibit function of wild-type p53, e.g., mutations with truncated tetramerization domains that resulting mutated p53 cannot bind and inactive normal p53, these tumor cells can respond favorably to a p53 gene therapy.

Overall, compared with the above p53 biomarker profile analysis, all previous methods of p53 biomarker evaluations (Kyzas et al., 2005; George et al., 2007; Olivier et al., 2006; Geisler et al., 2002; Poeta et al., 2007; Soussi et al., 2006) teach only partial recognition of the critical elements that are required to uniformly and specifically predict therapeutic outcomes. All methods that rely solely on immunohistochemistry (Geisler et al., 2002) or solely upon gene sequencing analyses (Poeta et al., 2007, Soussi et al., 2006, Olivier et al., 2006) miss important information regarding either the presence or level of normal or abnormal p53 protein that is critical to the correct prognostic/predictive decisions. Studies that combine p53 immunohistology and gene sequencing evaluations (Kyzas et al., 2005; George et al., 2007) have either combined the information inadequately, incompletely or incorrectly leading to erroneous conclusions regarding the predictive ability of these assessments.

For example, George et al. (2007) fail to teach the importance of the presence of a functional p53 gene/protein in their application of p53 immunohistology and p53 sequencing analyses. They include patients with both high and low level expression of exon 5 p53 protein mutations in the best prognostic category. They ignore the importance of the level of expression of the mutated exon 5 p53 protein and maintain that patients with exon 5 p53 mutations behave like those with normal p53 gene configurations. The poor prognosis of patients with high level expression of mutated exon 5 p53 protein is not anticipated or predicted by the teaching of George et al. (2007) who consider all exon 5 mutated cases to have a good prognosis regardless of their expression level of p53. In p53 clinical trials, none of these high level exon 5 p53 mutated protein expressing patients had a response to treatment and their median survival was similar to those of other patients with transdominant-negative p53 mutations in other DNA binding domain exons. The majority of the cases in the George et al. (2007) study with exon 5 mutations had low level expression of p53 protein that they incorrectly term wild-type when it will reflect low levels of abnormal p53 mutated protein. In their study, these cases were combined for classification with a smaller number of high expressing mutated exon 5 p53 protein cases that did not significantly alter the median survival of a favorable prognostic group they defined by combining all of these cases with an even larger number of patients having normal levels of normal p53 protein. Hence, George et al. (2007) does not to teach the importance of recognizing profiles where normal p53 will not be functional by failing to teach the importance of a high level of inactivating p53 transdominant-negative p53 protein from exon 5 mutations that can inactivate normal p53 if present.

These conclusions could not have been known or deduced from combining the results of the existing literature as evidenced by the failure of the preceding studies to utilize or define the correct combinations. This invention revealed the correct and proper protein expression and gene sequencing combinations to identify favorable and unfavorable p53 profiles based upon conditions that would either permit or prevent the function of normal p53 as described herein as the key factor for predictive and prognostic applications of p53 biomarker profiles.

B. Assessment of p53 Biomarker Profile by Combinational Analysis of p53 Gene Structure and Expression Level

1. Determination of p53 Gene Structure p53, one of the best known tumor suppressors, is a phosphoprotein of about 390 amino acids, which can be subdivided into five domains: an N-terminal transcription-activation domain (TAD), which activates transcription factors; a proline rich domain important for the apoptotic activity of p53; a central DNA-binding core domain (DBD), which contains one zinc atom and several arginine amino acid (encoded by exons 5-8); a homo-oligomerisation (tetramerization) domain (OD)—tetramerization is essential for the activity of p53 in vivo; a C-terminal involved in downregulation of DNA binding of the central domain.

p53 is located in the nucleus of cells and is very labile. Agents which damage DNA induce p53 to become very stable by a post-translational mechanism, allowing its concentration in the nucleus to increase dramatically. p53 suppresses progression through the cell cycle in response to DNA damage, thereby allowing DNA repair to occur before replicating the genome. Hence, p53 prevents the transmission of damaged genetic information from one cell generation to the next by initiating apoptosis if the damage to the cell is severe.

As discussed above, mutations in p53 can cause cells to become oncogenically transformed, and transfection studies have shown that p53 acts as a tumor suppressor, able to restore some level of normal growth to cancerous cells in vitro. p53 is a transcription factor and once activated, it represses transcription of several genes which are involved in stimulating cell growth, while stimulating expression of other genes involved in cell cycle control.

Mutations that deactivate p53 in cancer usually occur in the DNA binding domain. Most of these DNA binding mutations leave intact the tetramerization domain that can tetramerize with wild-type p53 molecules and inhibit the ability of the heterogenous tetramer to bind to its target DNA sequences, thus blocking the function of normal p53 in transcriptional activation of downstream genes. Therefore p53 with DNA binding domain mutations that can oligomerize with normal p53 have a dominant-negative effect on the function of p53. Mutations with dominant-negative effects may also be confirmed using functional assays as described below.

In certain aspects, cells that have elevated levels of p53 will thus be those cells having p53 missense mutations, trans-dominant mutations and gain of function mutations (e.g., de Vries et al., 2002) that lead to overexpression or decreased degradation of p53. The inventors contemplate that, particularly in patients with a high level of expression of mutated p53 protein that inhibit wild-type p53 function, such as p53 with missense mutating or trans-dominant mutations in exons 5-8 DNA binding core domain with intact tetramerization domains, a given p53 overexpressing cell, when transduced with adenoviral p53, will be less likely to produce enough wild-type p53 to swamp out the effects of an overexpressing endogenous p53 gain of function or trans-dominant allele, thus the patients will more likely be unfavorable responders to a p53 gene therapy. The similar prediction of unfavorable response applies to tumor cells which do not contain a wild-type p53 allele or contain two mutant p53 alleles. For a patient predicted to have a unfavorable response to a p53 gene therapy, the present invention may provide a method comprising administering the patient with a therapy other than a p53 therapy, such as methotrexate.

In some other aspects, cells that have at least wild-type p53 allele and/or cells that do not have a high level of blocking or inhibiting mutated p53 will probably respond to a p53 gene therapy favorably as predicted by the p53 biomarker profile. p53 gene therapy for introducing exogenous wild-type p53 combined with the effect of adenoviral vector on induction of endogenous wild-type p53 will increase wild-type p53 production in the cell and overcome the defects in those cases.

In order to detect the p53 gene structure in a tumor tissue, it is helpful to isolate and evaluate the tumor sample to account for the presence of normal cells that may be present in these tissues. Means for enriching a tissue preparation for tumor cells are known in the art. For example, the tissue may be isolated from paraffin-embedded or cryostat sections that have been stained and evaluated microscopically to determine a preponderance of tumor cells. Cancer cells may also be separated from normal cells by flow cytometry. These as well as other techniques for separating tumor from normal cells are well known in the art.

If the tumor tissue is highly contaminated with normal cells, detection of mutations is still readily achieved by sequencing techniques and chip arrays that employ PCR amplification of sample nucleic acid sequences. The presence of normal cells in the sample may make the detection of normal p53 alleles in the tumor cells more difficult to distinguish. The recent development of microdissection systems based on laser technology has largely solved this important problem. Laser microdissection is a powerful tool for the isolation of specific cell populations (or single cells) from stained sections of both formalin-fixed, paraffin-embedded and frozen tissues, from cell cultures and even of a single chromosome within a metaphase cell. Resulting material is suitable for a wide range of downstream assays such as LOH (loss of heterozygosity) studies, gene expression analysis at the mRNA level and a variety of proteomic approaches such as 2D gel analysis, reverse phase protein array and SELDI protein profiling. The application of single cell PCR is also contemplated to avoid normal tissue contamination.

Fluorescence in situ hybridization (FISH) and single nucleotide polymorphism arrays are additional methods that can detect the presence of normal p53 alleles in tumor cells even in samples containing a mixture of tumor and normal cells (Yamamoto et al., 2007; Ross, et al., 2007, George et al., 2007; Flotho et al., 2007; Fitzgibbon et al., 2007; Melcher et al., 2007; Purdie et al., 2007; Kawamata et al., 2008; Lindbjerg et al., 2007; van Beers et al., 2006).

Detection of point mutations may be accomplished by molecular cloning of the p53 allele (or alleles) present in the tumor tissue and sequencing that allele(s) using techniques well known in the art. Alternatively, the polymerase chain reaction can be used to amplify p53 gene sequences directly from a genomic DNA preparation from the tumor tissue. The DNA sequence of the amplified sequences can then be determined. The polymerase chain reaction itself is well known in the art. See e.g., Saiki et al. (1988); U.S. Pat. Nos. 4,683,202; and 4,683,195.

Specific deletions or truncation of p53 genes can also be detected. For example, restriction fragment length polymorphism (RFLP) probes for the p53 gene or surrounding marker genes can be used to score loss or partial loss of a p53 allele. Other techniques for detecting deletions or truncation, as are known in the art can be used.

Alternatively, mismatch detection can be used to detect point mutations in the p53 gene or its mRNA product. While these techniques are less sensitive than sequencing, they are simpler to perform on a large number of tumors. An example of a mismatch cleavage technique is the RNase protection method, which is described in detail in Winter et al. (1985); Meyers et al. (1985).

In similar fashion, DNA probes can be used to detect mismatches, through enzymatic or chemical cleavage. See, e.g., Cotton et al. (1988); Shenk et al. (1975). Alternatively, mismatches can be detected by shifts in the electrophoretic mobility of mismatched duplexes relative to matched duplexes. See, e.g., Cariello (1988). With either riboprobes or DNA probes, the cellular mRNA or DNA which might contain a mutation can be amplified using PCR before hybridization.

DNA sequences of the p53 gene from the tumor tissue which have been amplified by use of polymerase chain reaction may also be screened using allele-specific probes. These probes are nucleic acid oligomers, each of which contains a region of the p53 gene sequence harboring a known mutation. For example, one oligomer may be about 30 nucleotides in length, corresponding to a portion of the p53 gene sequence. At the position coding for the 175th codon of p53 gene the oligomer encodes an alanine, rather than the wild-type codon valine. By use of a battery of such allele-specific probes, the PCR amplification products can be screened to identify the presence of a previously identified mutation in the p53 gene. Hybridization of allele-specific probes with amplified p53 sequences can be performed, for example, on a nylon filter. Hybridization to a particular probe indicates the presence of the same mutation in the tumor tissue as in the allele-specific probe.

The identification of p53 gene structural changes in tumor cells has been facilitated through the development and application of a diverse series of high resolution, high throughput microarray platforms. Essentially there are two types of array; those that carry PCR products from cloned nucleic acids (e.g. cDNA, BACs, cosmids) and those that use oligonucleotides. Each has advantages and disadvantages but it is now possible to survey genome wide DNA copy number abnormalities and expression levels to allow correlations between losses, gains and amplifications in tumor cells with genes that are over- and under-expressed in the same samples. The gene expression arrays that provide estimates of mRNA levels in tumors have given rise to exon-specific arrays that can identify both gene expression levels, alternative splicing events and mRNA processing alterations. Oligonucleotide arrays are also being used to interrogate single nucleotide polymorphisms (SNPs) throughout the genome for linkage and association studies and these have been adapted to quantify copy number abnormalities and loss of heterozygosity events. Ultimately DNA sequencing arrays will allow resequencing of chromosome regions and whole genomes.

In the present invention, SNP-based arrays or other gene arrays or chips are contemplated to determine the presence of wild-type p53 allele and the structure of mutations. A single nucleotide polymorphism (SNP), a variation at a single site in DNA, is the most frequent type of variation in the genome. For example, there are an estimated 5-10 million SNPs in the human genome. As SNPs are highly conserved throughout evolution and within a population, the map of SNPs serves as an excellent genotypic marker for research. An SNP array is a useful tool to study the whole genome.

In addition, SNP array can be used for studying the Loss Of Heterozygosity (LOH). LOH is a form of allelic imbalance that can result from the complete loss of an allele or from an increase in copy number of one allele relative to the other. While other chip-based methods (e.g., comparative genomic hybridization can detect only genomic gains or deletions), SNP array has the additional advantage of detecting copy number neutral LOH due to uniparental disomy (UPD). In UPD, one allele or whole chromosome from one parent are missing leading to reduplication of the other parental allele (uni-parental=from one parent, disomy=duplicated). In a disease setting this occurrence may be pathologic when the wild-type allele (e.g., from the mother) is missing and instead two copies of the heterozygous allele (e.g., from the father) are present. This usage of SNP array has a huge potential in cancer diagnostics as LOH is a prominent characteristic of most human cancers. Recent studies based on the SNP array technology have shown that not only solid tumors (e.g. gastric cancer, liver cancer etc) but also hematologic malignancies (ALL, MDS, CML etc) have a high rate of LOH due to genomic deletions or UPD and genomic gains. In the present invention, using high density SNP array to detect LOH allows identification of pattern of allelic imbalance to determine the presence of wild-type p53 allele (Lips et al., 2005; Lai et al., 2007).

Examples for current p53 gene sequence and single nucleotide polymorphism arrays include p53 Gene Chip (Affymetrix, Santa Clara, Calif.), Roche p53 Ampli-Chip (Roche Molecular Systems, Pleasanton, Calif.), GeneChip Mapping arrays (Affymetrix, Santa Clara, Calif.), SNP Array 6.0 (Affymetrix, Santa Clara, Calif.), BeadArrays (Illumina, San Diego, Calif.), etc.

Mutations of wild-type p53 genes may also be detected on the basis of the mutation of a wild-type expression product of the p53 gene. Such expression products include both the mRNA as well as the p53 protein product itself. Point mutations may be detected by sequencing the mRNA directly or via molecular cloning of cDNA made from the mRNA. The sequence of the cloned cDNA can be determined using DNA sequencing techniques which are well known in the art. The cDNA can also be sequenced via the polymerase chain reaction (PCR).

A panel of monoclonal antibodies could be used in which each of the epitopes involved in p53 functions are represented by a monoclonal antibody. Loss or perturbation of binding of a monoclonal antibody in the panel would indicate mutational alteration of the p53 protein and thus of the p53 gene itself. Mutant p53 genes or gene products can also be detected in body samples, such as, serum, stool, or other body fluids, such as urine and sputum. The same techniques discussed above for detection of mutant p53 genes or gene products in tissues can be applied to other body samples.

2. Assessment of p53 Protein Level

Various patient parameters, including patient/disease history/characteristics as well as molecular characteristics (e.g., overexpression of p53 in a cancerous tumor combined with gene structure analysis), may be used as prognostic factors to predict the response or degree of benefit to a patient from a cancer therapy (e.g., adenoviral p53 gene therapy) as taught in the current invention.

Assessments of increased p53 protein levels may be direct, as in the use of quantitative immunohistochemistry (IHC) or other antibody based assays (Western blot, FIA, a radioimmunoassay (RIA), RIP, ELISA, immunoassay, immunoradiometric assay, a fluoroimmunoassay, an immunoassay, a chemiluminescent assay, a bioluminescent assay, a gel electrophoresis), or indirectly by quantitating the transcripts for these genes (in situ hybridization, nuclease protection, Northern blot or PCR, including RT-PCR).

With respect to immunohistology, normal cells express p53 at low levels that provide for absent of only faint staining in a small percentage of cells when viewed by light microscopy. Detection of visible nuclear staining in larger proportions of the tumor cells is indicative of the state of elevated, overexpressing, or high levels of p53 protein.

While not intending to be bound by any specific theory, the inventors propose that when a tumor cell exhibits elevated levels of p53 protein comparable to those in normal somatic cells, such an elevated level, is indicative of a dysfunction in the p53 tumor suppressor pathway, the principal pathway that regulates the cells apoptotic response to genetic mutation. It is postulated by the inventors that when there is a defect at some juncture in the pathway, that such a defect reveals itself in the elevated p53 levels. For example, it is known that when there is a defect in the p53 protein itself (i.e., resulting in a "mutant" p53), specifically in the DNA binding domain, and such a defect results in a dysfunctional p53 protein, which can tetramerize with normal p53 protein but cannot bind to DNA, the function of normal p53 is blocked. The cell overexpresses the dysfunctional protein relative to that seen in normal cells in a vain attempt to achieve a "normal" level of p53 protein function. Furthermore, tumor cells with high levels of mutated p53 that can block the function of normal p53 would also have a selective advantage compared to cells able to express functional levels of normal p53 that would suppress tumor growth. In addition, in some instances, the mutated p53 protein may be less amenable to degradation or clearance from the cell than wild-type p53, contributing to the apparent increased p53 content of the cell.

Elevated levels of p53 are known to signify abnormalities of the p53 tumor suppressor pathway and are associated with a poor prognosis in SCCHN cancers (Geisler et al., 2002); however, the present invention discloses that increased p53 protein levels alone is not sufficient to predict response to cancer therapy. In a particular embodiment, immunohistochemical detection of elevated levels of p53 compared to normal p53 expressing non-tumor tissues, which is due to high level of mutant proteins that can block the function of normal wild-type p53, provides an integrated prediction of a more likely unfavorable response to a p53 gene therapy. Indeed, it is contemplated that such a correlation will be evident as well in the case of gene therapy or other medicaments which often induce p53-mediated stress responses.

The present inventors also propose that a subset of tumors with elevated p53 protein could more likely be favorable responders. When defects occur elsewhere in the pathway (for example, in genes or genetic elements upstream or downstream of p53 protein in the pathway), that such defect(s) also can result in a disruption in the pathway, and thus lead to p53 protein elevation, again presumably due to the cell's attempt to compensate for loss or reduction of proper p53 pathway activity. Indeed, while virtually all normal somatic cells express p53 protein at near undetectable levels (e.g., detectable only by extremely sensitive techniques, such as RT-PCR), it has been found that a definable subset of tumors have elevated p53 protein, even though wild-type p53 allele or normal p53 gene structure is present. In this case, p53 function is often suppressed by elevated expression of p53 inhibitors like the molecules MDM2 and MDM4. In such tumor cells with elevated normal p53 protein, treatments that stimulate p53 stress responses can favorably alter the ratio of normal p53 to p53 inhibitor levels resulting in restoration of normal p53 activity and a favorable response to therapy. In tumors without any normal p53 or where the mutated p53 has blocking transdominant effects as described in this invention, normal p53 function will not be effected and these tumors will be less likely to respond favorably to a p53 gene therapy that exerts its effects through activation of p53-dependent pathways (p53-dependent apoptosis, senescence or cell cycle arrest).

Another case of favorable responders is exemplified by tumor cells with elevated p53 protein with a truncated tetramerization domain. Those mutant proteins cannot tetramerize with wild-type p53 protein to interfere with their DNA binding so these mutations do not inhibit function of wild-type p53 protein. These tumors would have favorable responses to p53 treatment when a second normal p53 allele is present or when exogenously administered normal p53 is delivered to the tumor.

The most common and convenient way of detecting such "elevated levels" of a tumor suppressor such as p53 is to select a technique that is sensitive enough to reflect or detect the protein levels commonly seen in cancer cells, yet not sufficiently sensitive to detect those levels common to normal somatic cells. Immunohistochemistry ("IHC") techniques include a family of exemplary detection technologies applicable that can be employed to detect the "elevated level" of p53, and thus are particularly applicable to the present invention (see, e.g., Ladner et al., 2000). Conveniently, IHC techniques are not generally sensitive enough to detect the small amounts of p53 protein produced, e.g., in normal somatic cells, and for that reason are now typically employed to detect elevated levels of p53 protein. A specific advantage for practice in connection with the present invention is that IHC detection of p53 protein will not generally discriminate between wild-type and mutant or aberrant p53 protein (since the underlying antibody can be selected, particularly in the case of the present invention, to detect most p53 proteins whether mutant or normal). In these cases, concurrent detection of p53 gene sequences and copy number are combined to determine the whether the patient has a p53 profile favorable or unfavorable for a response to a p53 gene therapy.

Nevertheless, the present invention is of course in no way limited to the use of IHC techniques to identify and select patients having tumors with elevated levels of p53 protein, or other measurable defects in the p53 pathway, in that the invention contemplates the use of any technique that will discriminate between cells exhibiting normal and abnormal expression of p53. Examples would include detection techniques that have been appropriately calibrated to distinguish between normal and abnormal levels of p53 mRNA expression and/or p53 protein translation levels. Such methods will include, in addition to immunological detection of p53 proteins, nucleic acid hybridization techniques such as gene arrays and chips, that are used to detect differences in mRNA levels, and thus may be employed to discriminate p53 mRNA levels. Exemplary normal and tumor cells (in the form of cell lines) that are known to typically have normal and elevated levels of p53 protein include cells such as WI-38, CCD 16 and MRC-9, and cell lines such as SCC61, SCC173 and SCC179, obtainable from common providers such as the ATCC and others.

This present invention, as set forth above, disclose that p53 therapy, and in particular, adenoviral p53 therapy, may work favorably in the subgroup of cancer patients with elevated wild-type p53 levels and an absence of high level expression of p53 mutations with blocking activity. In contrast, tumor cells with elevated p53 protein which block wild-type p53 protein respond poorly to a p53 gene therapy. This classification which combines protein level, gene sequence and gene copy number considerations provides an accurate prediction of therapeutic responders in the presence of elevated protein rather than an incomplete prognosis solely dependent on elevated protein level or mutation analysis alone.

3. Characterization of Mutant p53 Function

Mutations that can inhibit function of wild-type p53 genes can be detected by screening for loss of wild-type p53 protein function. Although all of the functions which the p53 protein undoubtedly possesses have yet to be elucidated, at least DNA binding functions are known. For example, protein p53 binds to the SV40 large T antigen as well as to the adenovirus E1B antigen or other known target DNA sequence. For a person skilled in the art, conventional methods can be used to detect loss of the ability of the p53 protein to bind to either or both of these antigens or other target DNA even in the presence of wild-type p53 protein, which indicates a mutational alteration in the protein which reflects a mutational alteration of the gene itself which could block function of wild-type p53 probably through tetramerization with wild-type p53 and prevent the binding with target DNA.

In the past decade, experimental functional assays have been performed in yeast and human cells as known for people skilled in the art to measure various properties of p53 mutant proteins including: transactivation activities of mutant proteins on reporter genes placed under the control of p53 response elements; dominant-negative effects over the wild-type protein; induction of cell-cycle arrest or apoptosis; temperature sensitivity; activities of mutant proteins that are independent and unrelated to the wild-type protein. Recently, results from these functional assays have been integrated into the International Agency for Research on Cancer (IARC) TP53 database through world wide web at p53.iarc.fr/. This database provides structured data and analysis tools to study p53 mutation patterns (Peitjean et al., 2007; Resnick and Inga, 2003). These methods may be employed to identify those p53 mutations that have the ability to exert dominant-negative blocking effects that would inhibit normal p53 function. When such transdominant-negative p53 mutations are expressed at high levels or when there is no ability for a cell to express normal p53, e.g., no normal p53 allele, such cases have an unfavorable outcome to a p53 gene therapy.

II. Cancer Therapies

In accordance with certain embodiments of the present invention, applicants also provide methods for predicting favorable response to a therapeutic cancer treatment and administering a therapy based on the p53 biomarker profile as described above. More particularly, the invention relates to treating hyperproliferative diseases by administering a anti-tumor therapy such as a p53 gene therapy.

A. Hyperproliferative Disease

A hyperproliferative disease is a disease associated with the abnormal growth or multiplication of cells. The hyperproliferative disease may be a disease that manifests as lesions in a subject, such a tumor. The tumor may be a benign tumor growth or cancer.

Exemplary tumor for which treatment is contemplated in the present invention include the following: squamous cell carcinoma, basal cell carcinoma, adenoma, adenocarcinoma, linitis plastica, insulinoma, glucagonoma, gastrinoma, vipoma, cholangiocarcinoma, hepatocellular carcinoma, adenoid cystic carcinoma, carcinoid tumor, prolactinoma, oncocytoma, hurthle cell adenoma, renal cell carcinoma, endometrioid adenoma, cystadenoma, pseudomyxoma peritonei, Warthin's tumor, thymoma, thecoma, granulosa cell tumor, arrhenoblastoma, Sertoli-Leydig cell tumor, paraganglioma, pheochromocytoma, glomus tumor, melanoma, soft tissue sarcoma, desmoplastic small round cell tumor, fibroma, fibrosarcoma, myxoma, lipoma, liposarcoma, leiomyoma, leiomyosarcoma, myoma, myosarcoma, rhabdomyoma, rhabdomyosarcoma, pleomorphic adenoma, nephroblastoma, brenner tumor, synovial sarcoma, mesothelioma, dysgerminoma, germ cell tumors, embryonal carcinoma, yolk sac tumor, teratomas, dermoid cysts, choriocarcinoma, mesonephromas, hemangioma, angioma, hemangiosarcoma, angiosarcoma, hemangioendothelioma, hemangioendothelioma, Kaposi's sarcoma, hemangiopericytoma, lymphangioma, cystic lymphangioma, osteoma, osteosarcoma, osteochondroma, cartilaginous exostosis, chondroma, chondrosarcoma, giant cell tumors, Ewing's sarcoma, odontogenic tumors, cementoblastoma, ameloblastoma, craniopharyngioma gliomas mixed oligoastrocytomas, ependymoma, astrocytomas, glioblastomas, oligodendrogliomas, neuroepitheliomatous neoplasms, neuroblastoma, retinoblastoma, meningiomas, neurofibroma, neurofibromatosis, schwannoma, neurinoma, neuromas, granular cell tumors, alveolar soft part sarcomas, lymphomas, non-Hodgkin's lymphoma, lymphosarcoma, Hodgkin's disease, small lymphocytic lymphoma, lymphoplasmacytic lymphoma, mantle cell lymphoma, primary effusion lymphoma, mediastinal (thymic) large cell lymphoma, diffuse large B-cell lymphoma, intravascular large B-cell lymphoma, Burkitt lymphoma, splenic marginal zone lymphoma, follicular lymphoma, extranodal marginal zone B-cell lymphoma of mucosa-associated lymphoid tissue (MALT-lymphoma), nodal marginal zone B-cell lymphoma, mycosis fungoides, Sezary syndrome, peripheral T-cell lymphoma, angioimmunoblastic T-cell lymphoma, subcutaneous panniculitis-like T-cell lymphoma, anaplastic large cell lymphoma, hepatosplenic T-cell lymphoma, enteropathy type T-cell lymphoma, lymphomatoid papulosis, primary cutaneous anaplastic large cell lymphoma, extranodal NK/T cell lymphoma, blastic NK cell lymphoma, plasmacytoma, multiple myeloma, mastocytoma, mast cell sarcoma, mastocytosis, mast cell leukemia, langerhans cell histiocytosis, histiocytic sarcoma, langerhans cell sarcoma dendritic cell sarcoma, follicular dendritic cell sarcoma, Waldenstrom macroglobulinemia, lymphomatoid granulomatosis, acute leukemia, lymphocytic leukemia, acute lymphoblastic leukemia, acute lymphocytic leukemia, chronic lymphocytic leukemia, adult T-cell leukemia/lymphoma, plasma cell leukemia, T-cell large granular lymphocytic leukemia, B-cell prolymphocytic leukemia, T-cell prolymphocytic leukemia, pecursor B lymphoblastic leukemia, precursor T lymphoblastic leukemia, acute erythroid leukemia, lymphosarcoma cell leukemia, myeloid leukemia, myelogenous leukemia, acute myelogenous leukemia, chronic myelogenous leukemia, acute promyelocytic leukemia, acute promyelocytic leukemia, acute myelomonocytic leukemia, basophilic leukemia, eosinophilic leukemia, acute basophilic leukemia, acute myeloid leukemia, chronic myelogenous leukemia, monocytic leukemia, acute monoblastic and monocytic leukemia, acute megakaryoblastic leukemia, acute myeloid leukemia and myelodysplastic syndrome, chloroma or myeloid sarcoma, acute panmyelosis with myelofibrosis, hairy cell leukemia, juvenile myelomonocytic leukemia, aggressive NK cell leukemia, polycythemia vera, myeloproliferative disease, chronic idiopathic myelofibrosis, essential thrombocytemia, chronic neutrophilic leukemia, chronic eosinophilic leukemia/hypereosinophilic syndrome, posttransplant lymphoproliferative disorder, chronic myeloproliferative disease, myelodysplastic/myeloproliferative diseases, chronic myelomonocytic leukemia and myelodysplastic syndrome.

The hyperproliferative disease or cancer may be treated after its initial diagnosis or subsequently by therapeutic nucleic acids or other therapies or combination of two or more therapies. A hyperproliferative disease or cancer recurrence may be defined as the reappearance or rediagnosis of a patent as having any hyperproliferative disease or cancer following any treatment including one or more of surgery, radiotherapy or chemotherapy. The patient with relapsed disease need not have been reported as disease free, but merely that the patient has exhibited renewed hyperproliferative disease or cancer growth following some degree of clinical response by the first therapy. The clinical response may be, but is not limited to, stable disease, tumor regression, tumor necrosis, absence of demonstrable cancer, reduction in tumor size or burden, blocking of tumor growth, reduction in tumor-associated pain, reduction in tumor associated pathology, reduction in tumor associated symptoms, tumor non-progression, increased disease free interval, increased time to progression, induction of remission, reduction of metastasis, or increased patient survival.

B. Squamous Cell Carcinoma

In particular, the tumor may be squamous cell carcinoma (SCCHN), more particularly, recurrent SCCHN. Recurrent SCCHN is one of the most horrible cancers. These tumors have very high mortality rates and cause severe suffering. Recurrent SCCHN tumors and standard therapies result in patient disfigurement and significant morbidities that impede fundamental functions like eating, swallowing and breathing. Patients often require invasive measures like feeding tubes and tracheotomies to support nutrition and respiration. Unfortunately, current therapies for this disease are woefully inadequate and result in considerable toxicity that often exacerbates tumor morbidities. The majority of patients do not respond to standard therapies and median survival is only 4 to 6 months. All of the chemotherapies utilized in treatment (methotrexate, cisplatinum, 5FU, and the taxanes) can result in oral mucositis which can exacerbate tumor morbidities. While the monoclonal antibody ERBITUX® (cetuximab) does not induce stomatitis, it can produce skin eruptions and increase radiation necrosis side effects.

In addition to the poor safety profiles of conventional treatments, responses are typically of short durations and the need for additional therapies is nearly universal. Hence, recurrent SCCHN clearly represents a medical condition with dire unmet needs that requires additional therapies preferably with agents that do not produce toxicities that compound tumor morbidities.

C. p53 Gene Therapy

In one embodiment, p53 gene therapy is contemplated. Human p53 gene therapy has been described in the literature since the mid-1990's. Roth et al. (1996) reported on retroviral-based therapy, and Clayman et al. (1998) described adenoviral delivery. U.S. Pat. Nos. 5,747,469; 6,017,524; 6,143,290; 6,410,010; and 6,511,847, U.S. Application 2002/0077313 and U.S. Application 2002/0006914 each describe methods of treating patients with p53, and are hereby incorporated by reference.

Local, regional (together loco-regional) or systemic delivery of expression constructs to patients is contemplated. It is proposed that this approach will provide clinical benefit, defined broadly as any of the following: reducing primary tumor size, reducing occurrence or size of metastasis, reducing or stopping tumor growth, inducing remission, increasing the duration before recurrence, reducing tumor-associated pain, inhibiting tumor cell division, killing a tumor cell, inducing apoptosis in a tumor cell, reducing or eliminating tumor recurrence, and/or increasing patient survival.

In particular aspects, the p53 gene therapy is ADVEXIN® (Ad5CMV-p53, INGN 201). ADVEXIN® (Ad5CMV-p53, INGN 201) is effective as a single agent and its anti-tumor activity correlates with the expression of ADVEXIN® (Ad5CMV-p53, INGN 201). delivered p53 protein resulting in subsequent alterations in the expression of p53-responsive genes. These genes and their gene products influence a wide range of cellular processes that lead to anti-tumor effects. Understanding the nature of these processes is critical to interpreting the types of clinical responses that are observed following ADVEXIN® (Ad5CMV-p53, INGN 201) treatment.

ADVEXIN® (Ad5CMV-p53, INGN 201) is one of the first anti-cancer agents that induces cellular senescence as a key mechanism of action. The induction of cellular senescence results in "permanent cell cycle arrest" and is observed following transient restoration of p53 activity in tumors with inactivated p53. Clinically, the induction of permanent cell cycle arrest would be associated with stabilization of tumor growth rather than reductions in tumor size. Animal tumor models and human clinical trials have clearly confirmed the activation of cell cycle arrest/senescence following ADVEXIN® (Ad5CMV-p53, INGN 201) therapy. P53 also activates anti-angiogenic mechanisms which are also associated with the stabilization of tumor growth rather than reductions in tumor size. Alternatively, apoptosis or "programmed cell death" is another key pathway activated by p53 restoration. With respect to clinical tumor responses, apoptosis induction would be expected to result in reductions of tumor size following ADVEXIN® (Ad5CMV-p53, INGN 201) therapy. These key p53 tumor suppression mechanisms and their molecular mediators are illustrated in FIG. 1.

Typically, all three therapeutic pathways (Cell cycle arrest-Apoptosis-Anti-Angiogenesis) are induced within a tumor following restoration of p53 activity. Individual tumor cells may activate either the cell cycle arrest/senescence or apoptosis pathways and the factors which determine which pathway is triggered for a particular cell are presently unclear. Depending upon which of these mechanisms are predominantly induced within the tumor cells will determine the nature of the clinical responses observed following ADVEXIN® (Ad5CMV-p53, INGN 201) therapy. As diagramed in FIG. 2, a spectrum of anti-tumor responses is expected ranging from stabilization of tumor growth to complete tumor eradication, including senescence/stabelstable disease (FIG. 3) and apoptosis/tumor reduction (FIG. 4), depending upon the relative proportion of cells which activate either cellular senescence or apoptosis pathways.

Consistent with these considerations of therapeutic mechanisms, there is a growing body of data indicating that conventional tumor response criteria based upon complete (CR) and partial (PR) reductions in size of .gtoreq.50% do not optimally identify clinically relevant responses associated with increased survival (Lara et al., 2008). Lara et al. (2008) recently reported results of three randomized, controlled Southwest Oncology Group clinical trials involving 984 lung cancer patients indicating that tumor growth control (TGC) defined by CR, PR or Stable Disease was significantly superior to conventional CR+PR definitions in predicting survival. Similarly, Choi and colleagues (2007) demonstrated that a ≥10% reduction in tumor size by computerized tomography (CT) was highly correlated with tumor response by positron emission tomography (PET) and was a more sensitive predictor of survival benefit than standard response criteria in gastrointestinal stromal tumors treated with imatinib (Choi, 2007; Benjamin, 2007).

Hence, for agents like ADVEXIN® (Ad5CMV-p53, INGN 201). that are known to induce cell cycle arrest and senescence as important mechanisms of action, tumor response definitions based upon tumor growth control (TGC=CR+PR+SD) or reductions in tumor size of ≥10% are more appropriate for defining tumor responses predictive of increased survival following treatment.

III. Therapeutic Genes

In certain embodiments of the invention, there is provide a method of administering the patient a p53 gene therapy, a therapy other than p53 gene therapy or a second anti-tumor therapy based on the p53 biomarker profile of the patient. The method may use therapeutic nucleic acids in certain aspects, and particular p53 gene in the p53 gene therapy.

A. Therapeutic Nucleic Acids

A "therapeutic nucleic acid" is defined herein to refer to a nucleic acid which can be administered to a subject for the purpose of treating or preventing a disease. The nucleic acid herein is one which is known or suspected to be of benefit in the treatment of a hyperproliferative disease. Therapeutic benefit may arise, for example, as a result of alteration of expression of a particular gene or genes by the nucleic acid. Alteration of expression of a particular gene or genes may be inhibition or augmentation of expression of a particular gene. Certain embodiments of the present invention concern the administration of a therapeutic nucleic acid.

A "nucleic acid" as used herein will generally refer to a molecule (i.e., a strand) of DNA, RNA or a derivative or analog thereof, comprising a nucleotide base. A nucleotide base includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 8 and about 100 nucleotide bases in length. The term "polynucleotide" refers to at least one molecule of greater than about 100 nucleotide bases in length.

In certain embodiments, a "gene" refers to a nucleic acid that is transcribed. In certain aspects, the gene includes regulatory sequences involved in transcription or message production. In particular embodiments, a gene comprises transcribed sequences that encode for a protein, polypeptide or peptide. As will be understood by those in the art, this functional term "gene" includes genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered nucleic acid segments may express, or may be adapted to express proteins, polypeptides, polypeptide domains, peptides, fusion proteins, mutant polypeptides and/or the like.

"Isolated substantially away from other coding sequences" means that the gene of interest forms part of the coding region of the nucleic acid segment, and that the segment does not contain large portions of naturally-occurring coding nucleic acid, such as large chromosomal fragments or other functional genes or cDNA coding regions. Of course, this refers to the nucleic acid as originally isolated, and does not exclude genes or coding regions later added to the nucleic acid by the hand of man.

In particular embodiments the therapeutic nucleic acid is in the form of a nucleic acid "expression construct." Throughout this application, the term "expression construct" is meant to include any type of nucleic acid in which all or part of the nucleic acid is capable of being transcribed. The transcribed portion may encode a therapeutic gene capable of being translated into a therapeutic gene product such as a protein, but it need not be. In other embodiments the transcribed portion may simply act to inhibit or augment expression of a particular gene.

In certain embodiments of the present invention, the therapeutic nucleic acid encodes a "therapeutic gene." As will be understood by those in the art, the term "therapeutic gene" includes genomic sequences, cDNA sequences, and smaller engineered gene segments that express, or may be adapted to express, proteins, polypeptides, domains, peptides, fusion proteins, and mutants, all of which are capable of providing a clinical benefit to a patient suffering from a hyperproliferative disease. The therapeutic nucleic acid encoding a therapeutic gene may comprise a contiguous nucleic acid sequence of about 5 to about 20,000 or more nucleotides, nucleosides, or base pairs.

Patients with unresectable tumors may be treated according to the present invention. As a consequence, the tumor may reduce in size, or the tumor vasculature may change such that the tumor becomes resectable. If so, standard surgical resection may be permitted. Another particular mode of administration that can be used in conjunction with surgery is treatment of an operative tumor bed. Thus, in either the primary gene therapy treatment, or in a subsequent treatment, one may perfuse the resected tumor bed with the vector during surgery, and following surgery, optionally by inserting a catheter into the surgery site.

B. Purification and Expression of Nucleic Acids

A nucleic acid may be purified on polyacrylamide gels, cesium chloride centrifugation gradients, column chromatography or by any other means known to one of ordinary skill in the art (see for example, Sambrook et al., 2001, incorporated herein by reference). In certain aspects, the present invention concerns a nucleic acid that is an isolated nucleic acid. As used herein, the term "isolated nucleic acid" refers to a nucleic acid molecule (e.g., an RNA or DNA molecule) that has been isolated free of, or is otherwise free of, bulk of cellular components or in vitro reaction components, and/or the bulk of the total genomic and transcribed nucleic acids of one or more cells. Methods for isolating nucleic acids (e.g., equilibrium density centrifugation, electrophoretic separation, column chromatography) are well known to those of skill in the art.

In accordance with the present invention, it will be desirable to produce therapeutic proteins in a target cell. Expression typically requires that appropriate signals be provided in the vectors or expression cassettes, and which include various regulatory elements, such as enhancers/promoters from viral and/or mammalian sources that drive expression of the genes of interest in host cells. Elements designed to optimize messenger RNA stability and translatability in host cells may also be included. Drug selection markers may be incorporated for establishing permanent, stable cell clones.

Viral vectors are selected eukaryotic expression systems. Included are adenoviruses, adeno-associated viruses, retroviruses, herpesviruses, lentivirus and poxviruses including vaccinia viruses and papilloma viruses including SV40. Viral vectors may be replication-defective, conditionally-defective or replication-competent. Also contemplated are non-viral delivery systems, including lipid-based vehicles.

C. Vectors and Expression Constructs

The term "vector" is used to refer to a carrier nucleic acid molecule into which a nucleic acid sequence can be inserted for introduction into a cell where it can be replicated and/or expressed. A nucleic acid sequence can be "exogenous" or "heterologous" which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Sambrook et al., 2001 and Ausubel et al., 1996, both incorporated herein by reference).

The term "expression vector" refers to any type of genetic construct comprising a nucleic acid coding for a RNA capable of being transcribed. In some cases, RNA molecules are then translated into a protein, polypeptide, or peptide. Expression vectors can contain a variety of "control sequences," which refer to nucleic acid sequences necessary for the transcription and possibly translation of an operable linked coding sequence in a particular host cell. In addition to control sequences that govern transcription and translation, vectors and expression vectors may contain nucleic acid sequences that serve other functions as well, as described below.

In order to express p53 or a therapeutic gene other than p53, it is necessary to provide an expression vector. The appropriate nucleic acid can be inserted into an expression vector by standard subcloning techniques. The manipulation of these vectors is well known in the art. Examples of fusion protein expression systems are the glutathione S-transferase system (Pharmacia, Piscataway, N.J.), the maltose binding protein system (NEB, Beverley, Mass.), the FLAG system (IBI, New Haven, Conn.), and the 6×His system (Qiagen, Chatsworth, Calif.).

In yet another embodiment, the expression system used is one driven by the baculovirus polyhedron promoter. The gene encoding the protein can be manipulated by standard techniques in order to facilitate cloning into the baculovirus vector. A particular baculovirus vector is the pBlueBac vector (Invitrogen, Sorrento, Calif.). The vector carrying the gene of interest is transfected into *Spodoptera frugiperda* (Sf9) cells by standard protocols, and the cells are cultured and processed to produce the recombinant protein. Mammalian cells exposed to baculoviruses become infected and may express the foreign gene only. This way one can transduce all cells and express the gene in dose dependent manner.

There also are a variety of eukaryotic vectors that provide a suitable vehicle in which recombinant polypeptide can be produced. HSV has been used in tissue culture to express a large number of exogenous genes as well as for high level expression of its endogenous genes. For example, the chicken ovalbumin gene has been expressed from HSV using an α promoter. Herz and Roizman (1983). The lacZ gene also has been expressed under a variety of HSV promoters.

Throughout this application, the term "expression construct" is meant to include any type of genetic construct containing a nucleic acid coding for a gene product in which part or all of the nucleic acid encoding sequence is capable of being transcribed. The transcript may be translated into a protein, but it need not be. Thus, in certain embodiments, expression includes both transcription of a gene and translation of a RNA into a gene product. In other embodiments, expression only includes transcription of the nucleic acid.

In particular embodiments, the nucleic acid is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7-20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30-110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription.

The particular promoter that is employed to control the expression of a nucleic acid is not believed to be critical, so long as it is capable of expressing the nucleic acid in the targeted cell. Thus, where a human cell is targeted, it is particularly to position the nucleic acid coding region adjacent to and under the control of a promoter that is capable of being expressed in a human cell. Generally speaking, such a promoter might include either a human or viral promoter.

In various other embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose.

Enhancers were originally detected as genetic elements that increased transcription from a promoter located at a distant position on the same molecule of DNA. This ability to act over a large distance had little precedent in classic studies of prokaryotic transcriptional regulation. Subsequent work showed that regions of DNA with enhancer activity are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

One will typically include a polyadenylation signal to effect proper polyadenylation of the transcript. The nature of the polyadenylation signal is not believed to be crucial to the successful practice of the invention, and any such sequence may be employed. Particular embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements (Bittner et al., 1987).

In various embodiments of the invention, the expression construct may comprise a virus or engineered construct derived from a viral genome. The ability of certain viruses to enter cells via receptor-mediated endocytosis and to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986) and adeno-associated viruses. Retroviruses also are attractive gene transfer vehicles (Nicolas and Rubenstein, 1988; Temin, 1986) as are vaccinia virus (Ridgeway, 1988) and adeno-associated virus (Ridgeway, 1988). Such vectors may be used to (i) transform cell lines in vitro for the purpose of expressing proteins of interest or (ii) to transform cells in vitro or in vivo to provide therapeutic polypeptides in a gene therapy scenario.

a. Viral Vectors

Viral vectors are a kind of expression construct that utilizes viral sequences to introduce nucleic acid and possibly proteins into a cell. The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Vector components of the present invention may be a viral vector that encode one or more candidate substance or other components such as, for example, an immunomodulator or adjuvant for the candidate substance. Non-limiting examples of virus vectors that may be used to deliver a nucleic acid of the present invention are described below.

Adenovirus is a non-enveloped double-stranded DNA virus. The virion consists of a DNA-protein core within a protein capsid. Virions bind to a specific cellular receptor, are endocytosed, and the genome is extruded from endosomes and transported to the nucleus. The genome is about 36 kB, encoding about 36 genes. In the nucleus, the "immediate early" E1A proteins are expressed initially, and these proteins induce expression of the "delayed early" proteins encoded by the E1B, E2, E3, and E4 transcription units. Virions assemble in the nucleus at about 1 day post-infection (p.i.), and after 2-3 days the cell lyses and releases progeny virus. Cell lysis is mediated by the E3 11.6K protein, which has been renamed "adenovirus death protein" (ADP).

Adenovirus is particularly suitable for use as a gene transfer vector because of its mid-sized genome, ease of manipulation, high titer, wide target-cell range and high infectivity. Both ends of the viral genome contain 100-200 base pair inverted repeats (ITRs), which are cis elements necessary for viral DNA replication and packaging. The early (E) and late (L) regions of the genome contain different transcription units that are divided by the onset of viral DNA replication. The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression and host cell shut-off (Renan, 1990). The products of the late genes, including the majority of the viral capsid proteins, are expressed only after significant processing of a single primary transcript issued by the major late promoter (MLP). The MLP (located at 16.8 m.u.) is particularly efficient during the late phase of infection, and all the mRNA's issued from this promoter possess a 5'-tripartite leader (TPL) sequence which makes them particular mRNA's for translation.

Adenovirus may be any of the 51 different known serotypes or subgroups A-F. Adenovirus type 5 of subgroup C is the human adenovirus about which the most biochemical and genetic information is known, and it has historically been used for most constructions employing adenovirus as a vector. Recombinant adenovirus often is generated from homologous recombination between shuttle vector and provirus vector. Due to the possible recombination between two proviral vectors, wild-type adenovirus may be generated from this process. Therefore, it is critical to isolate a single clone of virus from an individual plaque and examine its genomic structure.

Viruses used in gene therapy may be either replication-competent or replication-deficient. Generation and propagation of the adenovirus vectors which are replication-deficient depends on a helper cell line, the prototype being 293 cells, prepared by transforming human embryonic kidney cells with Ad5 DNA fragments; this cell line constitutively expresses E1 proteins (Graham et al., 1977). However, helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the particular helper cell line is 293.

Racher et al. (1995) have disclosed improved methods for culturing 293 cells and propagating adenovirus. In one format, natural cell aggregates are grown by inoculating individual cells into 1 liter siliconized spinner flasks (Techne, Cambridge, UK) containing 100-200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Adenovirus growth and manipulation is known to those of skill in the art, and exhibits broad host range in vitro and in vivo. This group of viruses can be obtained in high titers, e.g., $10^9$-$10^{13}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Animal studies have suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

As stated above, Ad vectors are based on recombinant Ad's that are either replication-defective or replication-competent. Typical replication-defective Ad vectors lack the E1A and E1B genes (collectively known as E1) and contain in their place an expression cassette consisting of a promoter and pre-mRNA processing signals which drive expression of a foreign gene. These vectors are unable to replicate because they lack the E1A genes required to induce Ad gene expression and DNA replication. In addition, the E3 genes can be deleted because they are not essential for virus replication in cultured cells. It is recognized in the art that replication-defective Ad vectors have several characteristics that make them suboptimal for use in therapy. For example, production of replication-defective vectors requires that they be grown on a complementing cell line that provides the E1A proteins in trans.

Several groups have also proposed using replication-competent Ad vectors for therapeutic use. Replication-competent vectors retain Ad genes essential for replication, and thus do not require complementing cell lines to replicate. Replication-competent Ad vectors lyse cells as a natural part of the life cycle of the vector. An advantage of replication-competent Ad vectors occurs when the vector is engineered to encode and express a foreign protein. Such vectors would be expected to greatly amplify synthesis of the encoded protein in vivo as the vector replicates. For use as anti-cancer agents, replication-competent viral vectors would theoretically be advantageous in that they would replicate and spread throughout the tumor, not just in the initially infected cells as is the case with replication-defective vectors.

Yet another approach is to create viruses that are conditionally-replication competent. Onyx Pharmaceuticals recently reported on adenovirus-based anti-cancer vectors which are replication-deficient in non-neoplastic cells, but which exhibit a replication phenotype in neoplastic cells lacking functional p53 and/or retinoblastoma (pRB) tumor suppressor proteins (U.S. Pat. No. 5,677,178). This phenotype is reportedly accomplished by using recombinant adenoviruses containing a mutation in the E1B region that renders the encoded E1B-55K protein incapable of binding to p53 and/or a mutation(s) in the E1A region which make the encoded E1A protein (p289R or p243R) incapable of binding to pRB and/or p300 and/or p107. E1B-55K has at least two independent functions: it binds and inactivates the tumor suppressor protein p53, and it is required for efficient transport of Ad mRNA from the nucleus. Because these E1B and E1A viral proteins are involved in forcing cells into S-phase, which is required for replication of adenovirus DNA, and because the p53 and pRB proteins block cell cycle progression, the recombinant adenovirus vectors described by Onyx should replicate in cells defective in p53 and/or pRB, which is the case for many cancer cells, but not in cells with wild-type p53 and/or pRB.

Another replication-competent adenovirus vector has the gene for E1B-55K replaced with the herpes simplex virus thymidine kinase gene (Wilder et al., 1999a). The group that constructed this vector reported that the combination of the vector plus gancyclovir showed a therapeutic effect on a human colon cancer in a nude mouse model (Wilder et al., 1999b). However, this vector lacks the gene for ADP, and accordingly, the vector will lyse cells and spread from cell-to-cell less efficiently than an equivalent vector that expresses ADP.

One may also take advantage of various promoter systems to create adenovirus vectors which overexpress p53. Vectors may also be replication competent or conditionally replicative. Other versions of engineered adenoviruses include disrupting E1A's ability to bind p300 and/or members of the Rb family members, or Ad vectors lacking expression of at least one E3 protein selected from the group consisting of 6.7K, gp19K, RIDα (also known as 10.4K); RIDβ (also known as 14.5K) and 14.7K. Because wild-type E3 proteins inhibit immune-mediated inflammation and/or apoptosis of Ad-infected cells, a recombinant adenovirus lacking one or more of these E3 proteins may stimulate infiltration of inflammatory and immune cells into a tumor treated with the adenovirus and that this host immune response will aid in destruction of the tumor as well as tumors that have metastasized. A mutation in the E3 region would impair its wild-type function, making the viral-infected cell susceptible to attack by the host's immune system. These viruses are described in detail in U.S. Pat. No. 6,627,190.

Other adenoviral vectors are described in U.S. Pat. Nos. 5,670,488; 5,747,869; 5,932,210; 5,981,225; 6,069,134; 6,136,594; 6,143,290; 6,210,939; 6,296,845; 6,410,010; and 6,511,184; U.S. Publication No. 2002/0028785.

Oncolytic viruses are also contemplated as vectors in the present invention. Oncolytic viruses are defined herein to generally refer to viruses that kill tumor or cancer cells more often than they kill normal cells. Exemplary oncolytic viruses include adenoviruses which overexpress ADP. These viruses are discussed in detail in U.S. Patent Application 20040213764, U.S. Patent Application 20020028785, and U.S. patent application Ser. No. 09/351,778, each of which is specifically incorporated by reference in its entirety into this section of the application and all other sections of the application. Exemplary oncolytic viruses are discussed elsewhere in this specification. One of ordinary skill in the art would be familiar with other oncolytic viruses that can be applied in the pharmaceutical compositions and methods of the present invention.

Adeno-associated virus (AAV) is an attractive vector system for use in the methods of the present invention as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

Retroviruses have promise as therapeutic vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136).

Recombinant lentiviral vectors are capable of infecting non-dividing cells and can be used for both in vivo and ex vivo gene transfer and expression of nucleic acid sequences.

For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

Herpes simplex virus (HSV) has generated considerable interest in treating nervous system disorders due to its tropism for neuronal cells, but this vector also can be exploited for other tissues given its wide host range. Another factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations.

HSV also is relatively easy to manipulate and can be grown to high titers. Thus, delivery is less of a problem, both in terms of volumes needed to attain sufficient MOI and in a lessened need for repeat dosings. For a review of HSV as a gene therapy vector, see Glorioso et al. (1995).

HSV, designated with subtypes 1 and 2, are enveloped viruses that are among the most common infectious agents encountered by humans, infecting millions of human subjects worldwide. The large, complex, double-stranded DNA genome encodes for dozens of different gene products, some of which derive from spliced transcripts. In addition to virion and envelope structural components, the virus encodes numerous other proteins including a protease, a ribonucleotides reductase, a DNA polymerase, a ssDNA binding protein, a helicase/primase, a DNA dependent ATPase, a dUTPase and others.

HSV genes form several groups whose expression is coordinately regulated and sequentially ordered in a cascade fashion (Honess and Roizman, 1974; Honess and Roizman 1975). The expression of α genes, the first set of genes to be expressed after infection, is enhanced by the virion protein number 16, or α-transinducing factor (Post et al., 1981; Batterson and Roizman, 1983). The expression of β genes requires functional α gene products, most notably ICP4, which is encoded by the α4 gene (DeLucao et al., 1985). γ genes, a heterogeneous group of genes encoding largely virion structural proteins, require the onset of viral DNA synthesis for optimal expression (Holland et al., 1980).

In line with the complexity of the genome, the life cycle of HSV is quite involved. In addition to the lytic cycle, which results in synthesis of virus particles and, eventually, cell death, the virus has the capability to enter a latent state in which the genome is maintained in neural ganglia until some as of yet undefined signal triggers a recurrence of the lytic cycle. Avirulent variants of HSV have been developed and are readily available for use in gene therapy contexts (U.S. Pat. No. 5,672,344).

Vaccinia virus vectors have been used extensively because of the ease of their construction, relatively high levels of expression obtained, wide host range and large capacity for carrying DNA. Vaccinia contains a linear, double-stranded DNA genome of about 186 kb that exhibits a marked "A-T" preference. Inverted terminal repeats of about 10.5 kb flank the genome. The majority of essential genes appear to map within the central region, which is most highly conserved among poxviruses. Estimated open reading frames in vaccinia virus number from 150 to 200. Although both strands are coding, extensive overlap of reading frames is not common.

At least 25 kb can be inserted into the vaccinia virus genome (Smith and Moss, 1983). Prototypical vaccinia vectors contain transgenes inserted into the viral thymidine kinase gene via homologous recombination. Vectors are selected on the basis of a tk-phenotype. Inclusion of the untranslated leader sequence of encephalomyocarditis virus, the level of expression is higher than that of conventional vectors, with the transgenes accumulating at 10% or more of the infected cell's protein in 24 h (Elroy-Stein et al., 1989).

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

b. Non-Viral Delivery

Lipid-based non-viral formulations provide an alternative to viral gene therapies. Although many cell culture studies have documented lipid-based non-viral gene transfer, systemic gene delivery via lipid-based formulations has been limited. A major limitation of non-viral lipid-based gene delivery is the toxicity of the cationic lipids that comprise the non-viral delivery vehicle. The in vivo toxicity of liposomes partially explains the discrepancy between in vitro and in vivo gene transfer results. Another factor contributing to this contradictory data is the difference in liposome stability in the presence and absence of serum proteins. The interaction between liposomes and serum proteins has a dramatic impact on the stability characteristics of liposomes (Yang and Huang, 1997). Cationic liposomes attract and bind negatively charged serum proteins. Liposomes coated by serum proteins are either dissolved or taken up by macrophages leading to their removal from circulation. Current in vivo liposomal delivery methods use aerosolization, subcutaneous, intradermal, intratumoral, or intracranial injection to avoid the toxicity and stability problems associated with cationic lipids in the circulation. The interaction of liposomes and plasma proteins is largely responsible for the disparity between the efficiency of in vitro (Felgner et al., 1987) and in vivo gene transfer (Zhu et al., 1993; Philip et al., 1993; Solodin et al., 1995; Thierry et al., 1995; Tsukamoto et al., 1995; Aksentijevich et al., 1996).

Recent advances in liposome formulations have improved the efficiency of gene transfer in vivo (Templeton et al. 1997; WO 98/07408, incorporated herein by reference). A novel liposomal formulation composed of an equimolar ratio of 1,2-bis(oleoyloxy)-3-(trimethyl ammonio)propane (DOTAP) and cholesterol significantly enhances systemic in vivo gene transfer, approximately 150-fold. The DOTAP: cholesterol lipid formulation is said to form a unique structure termed a "sandwich liposome." This formulation is reported to "sandwich" DNA between an invaginated bilayer or "vase" structure. Beneficial characteristics of these liposomes include a positive to negative charge or $\rho$, colloidal stabilization by cholesterol, two-dimensional DNA packing and increased serum stability.

The production of lipid formulations often is accomplished by sonication or serial extrusion of liposomal mixtures after (I) reverse phase evaporation (II) dehydration-rehydration (III) detergent dialysis and (IV) thin film hydration. Once manufactured, lipid structures can be used to encapsulate compounds that are toxic (chemotherapeutics) or labile (nucleic acids) when in circulation. Liposomal encapsulation has resulted in a lower toxicity and a longer serum half-life for such compounds (Gabizon et al., 1990). Numerous disease treatments are using lipid based gene transfer strategies to enhance conventional or establish novel therapies, in particular therapies for treating hyperproliferative diseases.

Liposomes are vesicular structures characterized by a lipid bilayer and an inner aqueous medium. Multilamellar liposomes have multiple lipid layers separated by aqueous medium. They form spontaneously when lipids are suspended in an excess of aqueous solution. The lipid components undergo self-rearrangement before the formation of structures that entrap water and dissolved solutes between the lipid bilayers (Ghosh and Bachhawat, 1991). Lipophilic molecules or molecules with lipophilic regions may also dissolve in or associate with the lipid bilayer.

The liposomes are capable of carrying biologically active nucleic acids, such that the nucleic acids are completely sequestered. The liposome may contain one or more nucleic acids and is administered to a mammalian host to efficiently deliver its contents to a target cell. The liposomes may comprise DOTAP and cholesterol or a cholesterol derivative. In certain embodiments, the ratio of DOTAP to cholesterol, cholesterol derivative or cholesterol mixture is about 10:1 to about 1:10, about 9:1 to about 1:9, about 8:1 to about 1:8, about 7:1 to about 1:7, about 6:1 to about 1:6, about 5:1 to about 1:5, about 4:1 to about 1:4, about 3:1 to 1:3, 2:1 to 1:2, and 1:1. In further embodiments, the DOTAP and/or cholesterol concentrations are about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, or 30 mM. The DOTAP and/or Cholesterol concentration can be between about 1 mM to about 20 mM, 1 mM to about 18 mM, 1 mM to about 16 mM, about 1 mM to about 14 mM, about 1 mM to about 12 mM, about 1 mM to about 10 mM, 1 to 8 mM, 2 to 7 mM, 3 to 6 mM and 4 to 5 mM. Cholesterol derivatives may be readily substituted for the cholesterol or mixed with the cholesterol in the present invention. Many cholesterol derivatives are known to the skilled artisan. Examples include but are not limited to cholesterol acetate and cholesterol oleate. A cholesterol mixture refers to a composition that contains at least one cholesterol or cholesterol derivative.

The formulation may also be extruded using a membrane or filter, and this may be performed multiple times. Such techniques are well-known to those of skill in the art, for example in Martin (1990). Extrusion may be performed to homogenize the formulation or limit its size. A contemplated method for preparing liposomes in certain embodiments is heating, sonicating, and sequential extrusion of the lipids through filters of decreasing pore size, thereby resulting in the formation of small, stable liposome structures. This preparation produces liposomal complexes or liposomes only of appropriate and uniform size, which are structurally stable and produce maximal activity.

For example, it is contemplated in certain embodiments of the present invention that DOTAP:Cholesterol liposomes are prepared by the methods of Templeton et al. (1997; incorporated herein by reference). Thus, in one embodiment, DOTAP (cationic lipid) is mixed with cholesterol (neutral lipid) at equimolar concentrations. This mixture of powdered lipids is then dissolved with chloroform, the solution dried to a thin film and the film hydrated in water containing 5% dextrose (w/v) to give a final concentration of 20 mM DOTAP and 20 mM cholesterol. The hydrated lipid film is rotated in a 50° C. water bath for 45 minutes, then at 35° C. for an additional 10 minutes and left standing at room temperature overnight. The following day the mixture is sonicated for 5 minutes at 50° C. The sonicated mixture is transferred to a tube and heated for 10 minutes at 50° C. This mixture is sequentially extruded through syringe filters of decreasing pore size (1 µm, 0.45 µm, 0.2 µm, 0.1 µm).

It also is contemplated that other liposome formulations and methods of preparation may be combined to impart desired DOTAP:Cholesterol liposome characteristics. Alternate methods of preparing lipid-based formulations for nucleic acid delivery are described by Saravolac et al. (WO 99/18933). Detailed are methods in which lipids compositions are formulated specifically to encapsulate nucleic acids. In another liposome formulation, an amphipathic vehicle called a solvent dilution microcarrier (SDMC) enables integration of particular molecules into the bi-layer of the lipid vehicle (U.S. Pat. No. 5,879,703). The SDMCs can be used to deliver lipopolysaccharides, polypeptides, nucleic acids and the like. Of course, any other methods of liposome preparation can be used by the skilled artisan to obtain a desired liposome formulation in the present invention.

Other formulations for delivering genes into tumors known to those skilled in the art may also be utilized in the invention. The present invention also includes nanoparticle liposome formulations for topical delivery of a nucleic acid expression construct. For instance, the liposome formulation may comprise DOTAP and cholesterol. An example of such a formulation containing a nucleic acid expression construct is shown below.

Cationic lipid (DOTAP) may be mixed with the neutral lipid cholesterol (Chol) at equimolar concentrations (Avanti Lipids). The mixed powdered lipids can be dissolved in HPLC-grade chloroform (Mallinckrodt, Chesterfield, Mo.) in a 1-L round-bottomed flask. After dissolution, the solution may be rotated on a Buchi rotary evaporator at 30° C. for 30 min to make a thin film. The flask containing the thin lipid film may then be dried under a vacuum for 15 min. Once drying is complete, the film may be hydrated in 5% dextrose in water (D5W) to give a final concentration of 20 mM DOTAP and 20 mM cholesterol, referred to as 20 mM DOTAP:Chol. The hydrated lipid film may be rotated in a water bath at 50° C. for 45 min and then at 35° C. for 10 min. The mixture may then be allowed to stand in the parafilm-covered flask at room temperature overnight, followed by sonication at low frequency (Lab-Line, TranSonic 820/H) for 5 min at 50° C. After sonication, the mixture may be transferred to a tube and heated for 10 min at 50° C., followed by sequential extrusion through Whatman (Kent, UK) filters of decreasing size: 1.0, 0.45, 0.2 and 0.1 µm using syringes. Whatman Anotop filters, 0.2 µm and 0.1 µm, may be used. Upon extrusion, the liposomes can be stored under argon gas at 4° C.

A nucleic acid expression construct in the form of plasmid DNA, for example 150 µg may be diluted in D5W. Stored liposomes may also be diluted in a separate solution of D5W. Equal volumes of both the DNA solution and the liposome solution can then be mixed to give a final concentration of, for example, 150 µg DNA/300 µl volume (2.5 µg/5 µl). Dilution and mixing may be performed at room temperature. The DNA solution mau then be added rapidly at the surface of the liposome solution by using a Pipetman pipet tip. The DNA:liposome mixture can then be mixed rapidly up and down twice in the pipette tip to form DOTAP:Cholesterol nucleic acid expression construct complexes.

Using the teachings of the specification and the knowledge of those skilled in the art, one can conduct tests to determine the particle size of the DOTAP:Chol-nucleic acid expression complex. For instance, the particle size of the DOTAP:Chol-nucleic acid expression construct complex may be determined using the N4-Coulter Particle Size analyzer (Beckman-Coulter). For this determination, 5 µl of the freshly prepared complex should be diluted in 1 ml of water prior to particle size determination. Additionally, a spectrophotometric reading of the complex at O.D. 400 nm may also be employed in analysis. For this analysis, 5 µl of the sample may be diluted in 95 µl of D5W to make a final volume of 100 µl. Applying the formulation techniques above with the size analysis methods should demonstrate a size of the complex between 374-400 nm.

Nanocapsules can generally entrap compounds in a stable and reproducible way. To avoid side effects due to intracellular polymeric overloading, such ultrafine particles (sized around 0.1 µm) should be designed using polymers able to be degraded in vivo. Biodegradable polyalkyl-cyanoacrylate nanoparticles that meet these requirements are contemplated for use in the present invention, and such particles may be are easily made. Methods pertaining to the use of nanoparticles that may be used with the methods and compositions of the present invention include U.S. Pat. Nos. 6,555,376, 6,797,704, U.S. Patent Appn. 20050143336, U.S. Patent Appn. 20050196343 and U.S. Patent Appn. 20050260276, each of which is herein specifically incorporated by reference in its entirety. U.S. Patent Publication 20050143336 for example, provides examples of nanoparticle formulations containing tumor suppressor genes such as p53 and FUS-1 in nucleic acid form which are complexed with cationic lipids such as DOTAP or neutral lipids such as DOPE which form liposomes.

2. Vector Delivery and Cell Transformation

Suitable methods for nucleic acid delivery for transformation of an organelle, a cell, a tissue or an organism for use with the current invention are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989; Nabel et al., 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harland and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973;

Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (WO 94/09699 and WO 95/06128; U.S. Pat. Nos. 5,610,042; 5,322,783, 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); and any combination of such methods.

3. Expression Systems

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC® 2.0 from INVITROGEN® and BACPACK™ BACULOVIRUS EXPRESSION SYSTEM FROM CLONTECH®.

Other examples of expression systems include STRATAGENE®'s COMPLETE CONTROL™ Inducible Mammalian Expression System, which involves a synthetic ecdysone-inducible receptor, or its pET Expression System, an *E. coli* expression system. Another example of an inducible expression system is available from INVITROGEN®, which carries the T-REX™ (tetracycline-regulated expression) System, an inducible mammalian expression system that uses the full-length CMV promoter. INVITROGEN® also provides a yeast expression system called the *Pichia methanolica* Expression System, which is designed for high-level production of recombinant proteins in the methylotrophic yeast *Pichia methanolica*. One of skill in the art would know how to express a vector, such as an expression construct, to produce a nucleic acid sequence or its cognate polypeptide, protein, or peptide.

It is contemplated that the therapeutic gene may be "overexpressed," i.e., expressed in increased levels relative to its natural expression in cells. Such overexpression may be assessed by a variety of methods, including radio-labeling and/or protein purification. However, simple and direct methods are contemplated, for example, those involving SDS/PAGE and protein staining or western blotting, followed by quantitative analyses, such as densitometric scanning of the resultant gel or blot. A specific increase in the level of the recombinant protein, polypeptide or peptide in comparison to the level in natural cells is indicative of overexpression, as is a relative abundance of the specific protein, polypeptides or peptides in relation to the other proteins produced by the host cell, e.g., visible on a gel.

In some embodiments, the expressed proteinaceous sequence forms an inclusion body in the host cell, the host cells are lysed, for example, by disruption in a cell homogenizer, washed and/or centrifuged to separate the dense inclusion bodies and cell membranes from the soluble cell components. This centrifugation can be performed under conditions whereby the dense inclusion bodies are selectively enriched by incorporation of sugars, such as sucrose, into the buffer and centrifugation at a selective speed. Inclusion bodies may be solubilized in solutions containing high concentrations of urea (e.g., 8M) or chaotropic agents such as guanidine hydrochloride in the presence of reducing agents, such as β-mercaptoethanol or DTT (dithiothreitol), and refolded into a more desirable conformation, as would be known to one of ordinary skill in the art.

The nucleotide and protein sequences for therapeutic genes have been previously disclosed, and may be found at computerized databases known to those of ordinary skill in the art. One such database is the National Center for Biotechnology Information's Genbank and GenPept databases (www.ncbi.nlm.nih.gov/). The coding regions for these known genes may be amplified and/or expressed using the techniques disclosed herein or by any technique that would be known to those of ordinary skill in the art. Additionally, peptide sequences may be synthesized by methods known to those of ordinary skill in the art, such as peptide synthesis using automated peptide synthesis machines, such as those available from Applied Biosystems (Foster City, Calif.).

IV. Combination Tumor Therapies

In accordance with certain aspects of the present invention, one or more therapies may be applied with combinational benefit to the patients. Such therapies include radiation, chemotherapy, surgery, cytokines, immunotherapy, biological therapies, toxins, drugs, dietary, or a gene therapy. Examples are discussed below.

To kill cancer cells, slow their growth, or to achieve any of the clinical endpoints discussed above, one may contact the cancer cell or tumor with primary p53 gene therapy in combination with a second anti-cancer therapy. These two modalities are provided in a combined amount effective to kill or inhibit proliferation of the cancer cell, or to achieve the desired clinical endpoint, including increasing patient survival. This process may involve contacting the cancer cell or tumor with both modalities at the same time. This may be achieved by contacting cancer cell or tumor with a single composition or pharmacological formulation that includes both agents, or by contacting the cancer cell or tumor with two distinct compositions or formulations, at the same time, wherein one composition includes the primary gene therapy, and the other includes the second therapy.

Alternatively, the primary p53 gene therapy may precede or follow the second therapy by intervals ranging from minutes to weeks. In embodiments where the two modalities are applied separately to the cancer cell or tumor, one would generally ensure that a significant period of time did not expire between the time of each delivery, such that both would still be able to exert an advantageously combined effect on the cancer cell or tumor. In such instances, it is contemplated that one would contact the cell with both modalities within about 12-24 hours of each other and, more particularly, within about 6-12 hours of each other, with a delay time of only about 12 hours being most particular. In some situations, it may be desirable to extend the time period for treatment significantly, however, where several days (2, 3, 4, 5, 6, or 7) to several weeks (1, 2, 3, 4, 5, 6, 7 or 8) lapse between the respective administrations.

It is also conceivable that more than one administration of each modality will be desired. Various combinations may be employed, where the primary gene therapy is "A" and the second therapy is "B":

A/B/A B/A/B A/B/A A/A/B A/B/B B/A/A B/B/B/A B/A/B/B
B/B/A/B A/A/B/B A/B/A/B A/B/B/A B/B/A/A B/A/B/A
B/A/A/B A/A/A/B B/A/A/A A/B/A/A A/A/B/A A/B/B/B

A. Therapeutic Nucleic Acids Encoding Therapeutic Genes

As discussed above, within various embodiments of the present invention there may be a need to provide a patient with a therapeutic gene for the purposes of treating a hyperproliferative disease. The term "gene therapy" within this application can be defined as delivery of a therapeutic gene or other therapeutic nucleic acid to a patient in need of such for purposes of treating a hyperproliferative disease or for treating a condition which, if left untreated may result in a hyperproliferative disease. Encompassed within the definition of "therapeutic gene" is a "biologically functional equivalent" therapeutic gene. Accordingly, sequences that have about 70% to about 99% homology of amino acids that are identical or functionally equivalent to the amino acids of the therapeutic gene will be sequences that are biologically functional equivalents provided the biological activity of the protein is maintained. Classes of therapeutic genes include tumor suppressor genes, cell cycle regulators, pro-apoptotic genes, cytokines, toxins, anti-angiogenic factors, and molecules than inhibit oncogenes, pro-angiogenic factors, growth factors, antisense transcripts, ribozymes and RNAi.

Examples of therapeutic genes include, but are not limited to, Rb, CFTR, p16, p21, p27, p57, p73, C-CAM, APC, CTS-1, zac1, scFV ras, DCC, NF-1, NF-2, WT-1, MEN-I, MEN-II, BRCA1, VHL, MMAC1, FCC, MCC, BRCA2, IL-1, IL-2, IL-3, IL-4, IL-5, IL-6, IL-7, IL-8, IL-9, IL-10, IL-11 IL-12, GM-CSF, G-CSF, thymidine kinase, mda7, fus, interferon α, interferon β, interferon γ, ADP, p53, ABLI, BLC1, BLC6, CBFA1, CBL, CSFIR, ERBA, ERBB, EBRB2, ETS1, ETS2, ETV6, FGR, FOX, FYN, HCR, HRAS, JUN, KRAS, LCK, LYN, MDM2, MLL, MYB, MYC, MYCL1, MYCN, NRAS, PIM1, PML, RET, SRC, TAL1, TCL3, YES, MADH4, RB1, TP53, WT1, TNF, BDNF, CNTF, NGF, IGF, GMF, aFGF, bFGF, NT3, NT5, ApoAI, ApoAIV, ApoE, Rap1A, cytosine deaminase, Fab, ScFv, BRCA2, zac1, ATM, HIC-1, DPC-4, FHIT, PTEN, ING1, NOEY1, NOEY2, OVCA1, MADR2, 53BP2, IRF-1, Rb, zac1, DBCCR-1, rks-3, COX-1, TFPI, PGS, Dp, E2F, ras, myc, neu, raf, erb, fms, trk, ret, gsp, hst, abl, E1A, p300, VEGF, FGF, thrombospondin, BAI-1, GDAIF, or MCC.

Other examples of therapeutic genes include genes encoding enzymes. Examples include, but are not limited to, ACP desaturase, an ACP hydroxylase, an ADP-glucose pyrophorylase, an ATPase, an alcohol dehydrogenase, an amylase, an amyloglucosidase, a catalase, a cellulase, a cyclooxygenase, a decarboxylase, a dextrinase, an esterase, a DNA polymerase, an RNA polymerase, a hyaluron synthase, a galactosidase, a glucanase, a glucose oxidase, a GTPase, a helicase, a hemicellulase, a hyaluronidase, an integrase, an invertase, an isomerase, a kinase, a lactase, a lipase, a lipoxygenase, a lyase, a lysozyme, a pectinesterase, a peroxidase, a phosphatase, a phospholipase, a phosphorylase, a polygalacturonase, a proteinase, a peptidase, a pullanase, a recombinase, a reverse transcriptase, a topoisomerase, a xylanase, a reporter gene, an interleukin, or a cytokine.

Further examples of therapeutic genes include the gene encoding carbamoyl synthetase I, ornithine transcarbamylase, arginosuccinate synthetase, arginosuccinate lyase, arginase, fumarylacetoacetate hydrolase, phenylalanine hydroxylase, alpha-1 antitrypsin, glucose-6-phosphatase, low-density-lipoprotein receptor, porphobilinogen deaminase, factor VIII, factor IX, cystathione β-synthase, branched chain ketoacid decarboxylase, albumin, isovaleryl-CoA dehydrogenase, propionyl CoA carboxylase, methyl malonyl CoA mutase, glutaryl CoA dehydrogenase, insulin, β-glucosidase, pyruvate carboxylase, hepatic phosphorylase, phosphorylase kinase, glycine decarboxylase, H-protein, T-protein, Menkes disease copper-transporting ATPase, Wilson's disease copper-transporting ATPase, cytosine deaminase, hypoxanthine-guanine phosphoribosyltransferase, galactose-1-phosphate uridyltransferase, phenylalanine hydroxylase, glucocerbrosidase, sphingomyelinase, α-L-iduronidase, glucose-6-phosphate dehydrogenase, HSV thymidine kinase, or human thymidine kinase.

Therapeutic genes also include genes encoding hormones. Examples include, but are not limited to, genes encoding growth hormone, prolactin, placental lactogen, luteinizing hormone, follicle-stimulating hormone, chorionic gonadotropin, thyroid-stimulating hormone, leptin, adrenocorticotropin, angiotensin I, angiotensin II, β-endorphin, β-melanocyte stimulating hormone, cholecystokinin, endothelin I, galanin, gastric inhibitory peptide, glucagon, insulin, lipotropins, neurophysins, somatostatin, calcitonin, calcitonin gene related peptide, β-calcitonin gene related peptide, hypercalcemia of malignancy factor, parathyroid hormone-related protein, parathyroid hormone-related protein, glucagon-like peptide, pancreastatin, pancreatic peptide, peptide YY, PHM, secretin, vasoactive intestinal peptide, oxytocin, vasopressin, vasotocin, enkephalinamide, metorphinamide, α melanocyte stimulating hormone, atrial natriuretic factor, amylin, amyloid P component, corticotropin releasing hormone, growth hormone releasing factor, luteinizing hormone-releasing hormone, neuropeptide Y, substance K, substance P, or thyrotropin releasing hormone.

Other examples of therapeutic genes include genes encoding antigens present in hyperproliferative tissues that can be used to elicit and immune response against that tissue. Anti-cancer immune therapies are well known in the art, for example, in greater detail in PCT application WO0333029, WO0208436, WO0231168, and WO0285287, each of which is specifically incorporated by reference in its entirety.

Yet other therapeutic genes are those that encode inhibitory molecules, such as antisense, ribozymes, siRNA and single chain antibodies. Such molecules can be used advantageously to inhibit hyperproliferative genes, such as oncogenes, inducers of cellular proliferation and pro-angiogenic factors.

1. Nucleic Acids Encoding Tumor Suppressors

A "tumor suppressor" refers to a polypeptide that, when present in a cell, reduces the tumorigenicity, malignancy, or hyperproliferative phenotype of the cell. The nucleic acid sequences encoding tumor suppressor gene amino acid sequences include both the full length nucleic acid sequence of the tumor suppressor gene, as well as non-full length sequences of any length derived from the full length sequences. It being further understood that the sequence includes the degenerate codons of the native sequence or sequences which may be introduced to provide codon preference in a specific host cell.

"Tumor suppressor genes" are generally defined herein to refer to nucleic acid sequences that reduce the tumorigenicity, malignancy, or hyperproliferative phenotype of the cell. Thus, the absence, mutation, or disruption of normal expression of a tumor suppressor gene in an otherwise healthy cell increases the likelihood of, or results in, the cell attaining a neoplastic state. Conversely, when a functional tumor suppressor gene or protein is present in a cell, its presence suppresses the tumorigenicity, malignancy or hyperproliferative phenotype of the host cell. Examples of tumor suppressor nucleic acids within this definition include, but are not limited to APC, CYLD, HIN-1, KRAS2b, p16, p19, p21, p27, p27mt, p53, p57, p73, PTEN, Rb, Uteroglobin, Skp2, BRCA-1, BRCA-2, CHK2, CDKN2A, DCC, DPC4, MADR2/JV18, FHIT, MEN1, MEN2, MTS1, NF1, NF2, VHL, WRN, WT1, CFTR, C-CAM, CTS-1, zac1, scFV, ras, MMAC1, FCC, MCC, Gene 26 (CACNA2D2), PL6, Beta* (BLU), Luca-1 (HYAL1), Luca-2 (HYAL2), 123F2 (RASSF1), 101F6, Gene 21 (NPRL2), or a gene encoding a SEM A3 polypeptide and FUS1. Other exemplary tumor suppressor genes are described in a database of tumor suppressor genes at (the world-wide-web cise.ufl.edu/~yyl/HTML-TSGDB/Homepage.html), incorporated therein by reference. This database is herein specifically incorporated by reference into this and all other sections of the present application. Nucleic acids encoding tumor suppressor genes, as discussed above, include tumor suppressor genes, or nucleic acids derived therefrom (e.g., cDNAs, cRNAs, mRNAs, and subsequences thereof encoding active fragments of the respective tumor suppressor amino acid sequences), as well as vectors comprising these sequences. One of ordinary skill in the art would be familiar with tumor suppressor genes that can be applied in the present invention.

2. Nucleic Acids Encoding Single Chain Antibodies

In certain embodiments of the present invention, the nucleic acid of the pharmaceutical compositions and devices set forth herein encodes a single chain antibody. Single-chain antibodies are described in U.S. Pat. Nos. 4,946,778 and 5,888,773, each of which are hereby incorporated by reference.

3. Nucleic Acids Encoding Cytokines

The term "cytokine" is a generic term for proteins released by one cell population which act on another cell as intercellular mediators. A "cytokine amino acid sequence" refers to a polypeptide that, when present in a cell, maintains some or all of the function of a cytokine. The nucleic acid sequences encoding cytokine amino acid sequences include both the full length nucleic acid sequence of the cytokine, as well as non-full length sequences of any length derived from the full length sequences. It being further understood, as discussed above, that the sequence includes the degenerate codons of the native sequence or sequences which may be introduced to provide codon preference in a specific host cell.

Examples of such cytokines are lymphokines, monokines, growth factors and traditional polypeptide hormones. Included among the cytokines are growth hormones such as human growth hormone, N-methionyl human growth hormone, and bovine growth hormone; parathyroid hormone; thyroxine; insulin; proinsulin; relaxin; prorelaxin; glycoprotein hormones such as follicle stimulating hormone (FSH), thyroid stimulating hormone (TSH), and luteinizing hormone (LH); hepatic growth factor; prostaglandin, fibroblast growth factor; prolactin; placental lactogen, OB protein; tumor necrosis factor-$\alpha$ and -$\beta$; mullerian-inhibiting substance; mouse gonadotropin-associated peptide; inhibin; activin; vascular endothelial growth factor; integrin; thrombopoietin (TPO); nerve growth factors such as NGF-$\beta$; platelet-growth factor; transforming growth factors (TGFs) such as TGF-$\alpha$ and TGF-$\beta$; insulin-like growth factor-I and -II; erythropoietin (EPO); osteoinductive factors; interferons such as interferon-$\alpha$, -$\beta$, and -$\gamma$; colony stimulating factors (CSFs) such as macrophage-CSF (M-CSF); granulocyte-macrophage-CSF (GM-CSF); and granulocyte-CSF (G-CSF); interleukins (ILs) such as IL-1, IL-1$\alpha$, IL-2, IL-3, IL-4, IL-5, IL-6, IL-7, IL-8, IL-9, IL-10, IL-11, IL-12; IL-13, IL-14, IL-15, IL-16, IL-17, IL-18, IL-24 (MDA-7), LIF, G-CSF, GM-CSF, M-CSF, EPO, kit-ligand or FLT-3.

4. Nucleic Acids Encoding Pro-Apoptotic Genes/Regulators of Programmed Cell Death Apoptosis, or programmed cell death, is an essential process for normal embryonic development, maintaining homeostasis in adult tissues, and suppressing carcinogenesis (Kerr et al., 1972). The Bcl-2 family of proteins and ICE-like proteases have been demonstrated to be important regulators and effectors of apoptosis in other systems. The Bcl-2 protein, discovered in association with follicular lymphoma, plays a prominent role in controlling apoptosis and enhancing cell survival in response to diverse apoptotic stimuli (Bakhshi et al., 1985; Cleary and Sklar, 1985; Cleary et al., 1986; Tsujimoto et al., 1985; Tsujimoto and Croce, 1986). The evolutionarily conserved Bcl-2 protein now is recognized to be a member of a family of related proteins, which can be categorized as death agonists or death antagonists.

Subsequent to its discovery, it was shown that Bcl-2 acts to suppress cell death triggered by a variety of stimuli. Also, it now is apparent that there is a family of Bcl-2 cell death regulatory proteins which share in common structural and sequence homologies. These different family members have been shown to either possess similar functions to Bcl-2 (e.g., $Bcl_{XL}$, $Bcl_W$, $Bcl_S$, Mcl-1, A1, Bfl-1) or counteract Bcl-2 function and promote cell death. The latter, known as pro-apoptotic genes, encode proteins that induce or sustain apoptosis to an active form. The present invention contemplates inclusion of any pro-apoptotic gene amino acid sequence known to those of ordinary skill in the art. Exemplary pro-apoptotic genes include CD95, caspase-3, Bax, Bag-1, CRADD, TSSC3, bax, hid, Bak, MKP-7, PERP, bad, bcl-2, MST1, bbc3, Sax, BIK, BID, and mda7. One of ordinary skill in the art would be familiar with pro-apoptotic genes, and other such genes not specifically set forth herein that can be applied in the methods and compositions of the present invention.

Nucleic acids encoding pro-apoptotic gene amino acid sequences include pro-apoptotic genes, or nucleic acids derived therefrom (e.g., cDNAs, cRNAs, mRNAs, and subsequences thereof encoding active fragments of the respective pro-apoptotic amino acid sequence), as well as vectors comprising these sequences. A "pro-apoptotic gene amino acid sequence" refers to a polypeptide that, when present in a cell, induces or promotes apoptosis.

5. Nucleic Acids Encoding Inhibitors of Angiogenesis

Inhibitors of angiogenesis include angiostatin and endostatin. Angiostatin is a polypeptide of approximately 200 amino acids. It is produced by the cleavage of plasminogen, a plasma protein that is important for dissolving blood clots. Angiostatin binds to subunits of ATP synthase exposed at the surface of the cell embedded in the plasma membrane. (Before this recent discovery, ATP synthase was known only as a mitochondrial protein. Endostatin is a polypeptide of 184 amino acids. It is the globular domain found at the C-terminus of Type XVIII (Mulder et al., 1995) collagen, a collagen found in blood vessels, cut off from the parent molecule.

Inhibitors of angiogenesis also include inhibitors or pro-angiongenic factors, such as antisense, ribozymes, siRNAs and single-chain antibodies, which are described elsewhere in this document. Epithelial cells express transmembrane proteins on their surface, called integrins, by which they anchor themselves to the extracellular matrix. It turns out that the new blood vessels in tumors express a vascular integrin, designated $\alpha v/\beta 3$, that is not found on the old blood vessels of normal tissues. Vitaxin®, a monoclonal antibody directed against the $\alpha v/\beta 3$ vascular integrin, shrinks tumors in mice without harming them. In Phase II clinical trials in humans, Vitaxin® has shown some promise in shrinking solid tumors without harmful side effects.

6. Nucleic Acids Encoding Inducers of Cellular Proliferation

The proteins that induce cellular proliferation further fall into various categories dependent on function. The commonality of all of these proteins is their ability to regulate cellular proliferation. For example, a form of PDGF, the sis oncogene, is a secreted growth factor. Oncogenes rarely arise from genes encoding growth factors, and at the present, sis is the only known naturally-occurring oncogenic growth factor.

The proteins FMS, ErbA, ErbB and neu are growth factor receptors. Mutations to these receptors result in loss of regulatable function. For example, a point mutation affecting the transmembrane domain of the Neu receptor protein results in the neu oncogene. The erbA oncogene is derived from the intracellular receptor for thyroid hormone. The modified oncogenic ErbA receptor is believed to compete with the endogenous thyroid hormone receptor, causing uncontrolled growth.

The largest class of oncogenes includes the signal transducing proteins (e.g., Src, Abl and Ras). The protein Src is a cytoplasmic protein-tyrosine kinase, and its transformation from proto-oncogene to oncogene in some cases, results via mutations at tyrosine residue 527. In contrast, transformation of GTPase protein ras from proto-oncogene to oncogene, in one example, results from a valine to glycine mutation at amino acid 12 in the sequence, reducing ras GTPase activity.

The proteins Jun, Fos and Myc are proteins that directly exert their effects on nuclear functions as transcription factors.

Antisense methodology takes advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject. In other embodiment of the present invention, it is contemplated that siRNA, ribozyme and single-chain antibody therapies directed at particular inducers of cellular proliferation can be used to prevent expression of the inducer of cellular proliferation, and hence provide a clinical benefit to a cancer patient.

7. Additional Nucleic Acid Based Therapies

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a particular embodiment includes an antisense construct with complementarity to regions within 50-200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology, but also contains a non-homologous region (e.g., ribozyme; see below) could be designed. These molecules, though having less than 50% homology, would bind to target sequences under appropriate conditions.

It may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

In certain embodiments of the present invention, the nucleic acid of the pharmaceutical compositions and devices set forth herein is a ribozyme. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cook, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cook et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cook et al., 1981). For example, U.S. Pat. No. 5,354,855 reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991; Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

In certain embodiments of the present invention, the therapeutic nucleic acid of the pharmaceutical compositions set forth herein is an RNAi. RNA interference (also referred to as "RNA-mediated interference" or RNAi) is a mechanism by which gene expression can be reduced or eliminated. Double-stranded RNA (dsRNA) has been observed to mediate the reduction, which is a multi-step process. dsRNA activates post-transcriptional gene expression surveillance mechanisms that appear to function to defend cells from virus infection and transposon activity (Fire et al., 1998; Grishok et al., 2000; Ketting et al., 1999; Lin and Avery et al., 1999; Montgomery et al., 1998; Sharp and Zamore, 2000; Tabara et al., 1999). Activation of these mechanisms targets mature, dsRNA-complementary mRNA for destruction. RNAi offers major experimental advantages for study of gene function. These advantages include a very high specificity, ease of movement across cell membranes, and prolonged down-regulation of the targeted gene (Fire et al., 1998; Grishok et al., 2000; Ketting et al., 1999; Lin and Avery et al., 1999; Montgomery et al., 1998; Sharp et al., 1999; Sharp and Zamore, 2000; Tabara et al., 1999). Moreover, dsRNA has been shown to silence genes in a wide range of systems, including plants, protozoans, fungi, *C. elegans, Trypanasoma, Drosophila*, and mammals (Grishok et al., 2000; Sharp et al., 1999; Sharp and Zamore, 2000; Elbashir et al., 2001). It is generally accepted that RNAi acts post-transcriptionally, targeting RNA transcripts for degradation. It appears that both nuclear and cytoplasmic RNA can be targeted (Bosher and Labouesse, 2000).

The endoribonuclease Dicer is known to produce two types of small regulatory RNAs that regulate gene expression: small interfering RNAs (siRNAs) and microRNAs (miRNAs) (Bernstein et al., 2001; Grishok et al., 2001; Hutvgner et al., 2001; Ketting et al., 2001; Knight and Bass, 2001). In animals, siRNAs direct target mRNA cleavage (Elbashir et al., 2001), whereas miRNAs block target mRNA translation (Lee et al., 1993; Reinhart et al., 2000; Brennecke et al., 2003; Xu et al., 2003). Recent data suggest that both siRNAs and miRNAs incorporate into similar perhaps even identical protein complexes, and that a critical determinant of mRNA destruction versus translation regulation is the degree of sequence complementary between the small RNA and its mRNA target (Hutvgner and Zamore, 2002; Mourelatos et al., 2002; Zeng et al., 2002; Doench et al., 2003; Saxena et al., 2003; Zeng et al., 2003). Many known miRNA sequences and their position in genomes or chromosomes can be found at www.sanger.ac.uk/Software/Rfam/mirna/help/summary.shtml.

siRNAs must be designed so that they are specific and effective in suppressing the expression of the genes of interest. Methods of selecting the target sequences, i.e., those sequences present in the gene or genes of interest to which the siRNAs will guide the degradative machinery, are directed to avoiding sequences that may interfere with the siRNA's guide function while including sequences that are specific to the gene or genes. Typically, siRNA target sequences of about 21 to 23 nucleotides in length are most effective. This length reflects the lengths of digestion products resulting from the processing of much longer RNAs as described above (Montgomery et al., 1998).

The making of siRNAs has been mainly through direct chemical synthesis; through processing of longer, double-stranded RNAs through exposure to *Drosophila* embryo lysates; or through an in vitro system derived from S2 cells. Use of cell lysates or in vitro processing may further involve the subsequent isolation of the short, 21-23 nucleotide siRNAs from the lysate, etc., making the process somewhat cumbersome and expensive. Chemical synthesis proceeds by making two single stranded RNA-oligomers followed by the annealing of the two single stranded oligomers into a double-stranded RNA. Methods of chemical synthesis are diverse. Non-limiting examples are provided in U.S. Pat. Nos. 5,889,136, 4,415,723, and 4,458,066, expressly incorporated herein by reference, and in Wincott et al. (1995).

Several further modifications to siRNA sequences have been suggested in order to alter their stability or improve their effectiveness. It is suggested that synthetic complementary 21-mer RNAs having di-nucleotide overhangs (i.e., 19 complementary nucleotides+3' non-complementary dimers) may provide the greatest level of suppression. These protocols primarily use a sequence of two (2'-deoxy) thymidine nucleotides as the di-nucleotide overhangs. These dinucleotide overhangs are often written as dTdT to distinguish them from the typical nucleotides incorporated into RNA. The literature has indicated that the use of dT overhangs is primarily motivated by the need to reduce the cost of the chemically synthesized RNAs. It is also suggested that the dTdT overhangs might be more stable than UU overhangs, though the data available shows only a slight (<20%) improvement of the dTdT overhang compared to an siRNA with a UU overhang.

WO 99/32619 and WO 01/68836 suggest that RNA for use in siRNA may be chemically or enzymatically synthesized. Both of these texts are incorporated herein in their entirety by reference. The enzymatic synthesis contemplated in these references is by a cellular RNA polymerase or a bacteriophage RNA polymerase (e.g., T3, T7, SP6) via the use and production of an expression construct as is known in the art. For example, see U.S. Pat. No. 5,795,715. The contemplated constructs provide templates that produce RNAs that contain nucleotide sequences identical to a portion of the target gene. The length of identical sequences provided by these references is at least 25 bases, and may be as many as 400 or more bases in length. An important aspect of this reference is that the authors contemplate digesting longer dsRNAs to 21-25mer lengths with the endogenous nuclease complex that converts long dsRNAs to siRNAs in vivo. They do not describe or present data for synthesizing and using in vitro transcribed 21-25mer dsRNAs. No distinction is made between the expected properties of chemical or enzymatically synthesized dsRNA in its use in RNA interference.

Similarly, WO 00/44914, incorporated herein by reference, suggests that single strands of RNA can be produced enzymatically or by partial/total organic synthesis. Particularly, single-stranded RNA is enzymatically synthesized from the PCR products of a DNA template, particularly a cloned cDNA template and the RNA product is a complete transcript of the cDNA, which may comprise hundreds of nucleotides. WO 01/36646, incorporated herein by reference, places no limitation upon the manner in which the siRNA is synthesized, providing that the RNA may be synthesized in vitro or in vivo, using manual and/or automated procedures. This reference also provides that in vitro synthesis may be chemical or enzymatic, for example using cloned RNA polymerase (e.g., T3, T7, SP6) for transcription of the endogenous DNA (or cDNA) template, or a mixture of both. Again, no distinction in the desirable properties for use in RNA interference is made between chemically or enzymatically synthesized siRNA.

U.S. Pat. No. 5,795,715 reports the simultaneous transcription of two complementary DNA sequence strands in a single reaction mixture, wherein the two transcripts are immediately hybridized. The templates used are particularly of between 40 and 100 base pairs, and which is equipped at each end with a promoter sequence. The templates are particularly attached to a solid surface. After transcription with RNA polymerase, the resulting dsRNA fragments may be used for detecting and/or assaying nucleic acid target sequences.

U.S. Patent App. 20050203047 reports of a method of modulating gene expression through RNA interference by incorporating a siRNA or miRNA sequence into a transfer RNA (tRNA) encoding sequence. The tRNA containing the siRNA or miRNA sequence may be incorporated into a nucleic acid expression construct so that this sequence is spliced from the expressed tRNA. The siRNA or miRNA sequence may be positioned within an intron associated with an unprocessed tRNA transcript, or may be positioned at either end of the tRNA transcript.

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266 032, incorporated herein by reference, or via deoxynucleoside H-phosphonate intermediates as described by Froehler et al. (1986) and U.S. Pat. No. 5,705,629, each incorporated herein by reference. Various mechanisms of oligonucleotide synthesis may be used, such as those methods disclosed in, U.S. Pat. Nos. 4,659,774; 4,816,571; 5,141,813; 5,264,566; 4,959,463; 5,428,148; 5,554,744; 5,574,146; 5,602,244 each of which are incorporated herein by reference.

A non-limiting example of an enzymatically produced nucleic acid include nucleic acids produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 2001, incorporated herein by reference).

B. Other Therapies

1. Surgery

Approximately 60% of persons with cancer will undergo surgery of some type, which includes preventative, diagnostic or staging, curative and palliative surgery. Curative surgery is a cancer treatment that may be used in conjunction with other therapies, such as the treatment of the present invention, chemotherapy, radiotherapy, hormonal therapy, gene therapy, immunotherapy and/or alternative therapies.

Curative surgery includes resection in which all or part of cancerous tissue is physically removed, excised, and/or destroyed. Tumor resection refers to physical removal of at least part of a tumor. In addition to tumor resection, treatment by surgery includes laser surgery, cryosurgery, electrosurgery, and microscopically controlled surgery (Mohs' surgery). It is further contemplated that the present invention may be used in conjunction with removal of superficial cancers, precancers, or incidental amounts of normal tissue.

Intratumoral injection prior to surgery or upon excision of part of all of cancerous cells, tissue, or tumor, a cavity may be formed in the body. Treatment may be accomplished by perfusion, direct injection or local application of these areas with an additional anti-cancer therapy. Such treatment may be repeated, for example, every 1, 2, 3, 4, 5, 6, or 7 days, or every 1, 2, 3, 4, and 5 weeks or every 1, 2, 3, 4, 5, 6, 7, 8, 9, 10, 11, or 12 months. These treatments may be of varying dosages as well.

2. Chemotherapy

A wide variety of chemotherapeutic agents may be used in accordance with the present invention. The term "chemotherapy" refers to the use of drugs to treat cancer. A "chemotherapeutic agent" is used to connote a compound or composition that is administered in the treatment of cancer. These agents or drugs are categorized by their mode of activity within a cell, for example, whether and at what stage they affect the cell cycle. Alternatively, an agent may be characterized based on its ability to directly cross-link DNA, to intercalate into DNA, or to induce chromosomal and mitotic aberrations by affecting nucleic acid synthesis. Most chemotherapeutic agents fall into the following categories: alkylating agents, antimetabolites, antitumor antibiotics, mitotic inhibitors, and nitrosoureas.

a. Alkylating Agents

Alkylating agents are drugs that directly interact with genomic DNA to prevent the cancer cell from proliferating. This category of chemotherapeutic drugs represents agents that affect all phases of the cell cycle, that is, they are not phase-specific. Alkylating agents can be implemented to treat chronic leukemia, non-Hodgkin's lymphoma, Hodgkin's disease, multiple myeloma, and particular cancers of the breast, lung, and ovary. They include: busulfan, chlorambucil, cisplatin, cyclophosphamide (cytoxan), dacarbazine, ifosfamide, mechlorethamine (mustargen), and melphalan. Troglitazaone can be used to treat cancer in combination with any one or more of these alkylating agents, some of which are discussed below.

b. Antimetabolites

Antimetabolites disrupt DNA and RNA synthesis. Unlike alkylating agents, they specifically influence the cell cycle during S phase. They have used to combat chronic leukemias in addition to tumors of breast, ovary and the gastrointestinal tract. Antimetabolites include 5-fluorouracil (5-FU), cytarabine (Ara-C), fludarabine, gemcitabine, and methotrexate.

5-Fluorouracil (5-FU) has the chemical name of 5-fluoro-2,4(1H,3H)-pyrimidinedione. Its mechanism of action is thought to be by blocking the methylation reaction of deoxyuridylic acid to thymidylic acid. Thus, 5-FU interferes with the synthesis of deoxyribonucleic acid (DNA) and to a lesser extent inhibits the formation of ribonucleic acid (RNA). Since DNA and RNA are essential for cell division and proliferation, it is thought that the effect of 5-FU is to create a thymidine deficiency leading to cell death. Thus, the effect of 5-FU is found in cells that rapidly divide, a characteristic of metastatic cancers.

c. Antitumor Antibiotics

Antitumor antibiotics have both antimicrobial and cytotoxic activity. These drugs also interfere with DNA by chemically inhibiting enzymes and mitosis or altering cellular membranes. These agents are not phase specific so they work in all phases of the cell cycle. Thus, they are widely used for a variety of cancers. Examples of antitumor antibiotics include bleomycin, dactinomycin, daunorubicin, doxorubicin (Adriamycin), and idarubicin, some of which are discussed in more detail below. Widely used in clinical setting for the treatment of neoplasms these compounds are administered through bolus injections intravenously at doses ranging from 25-75 $mg/m^2$ at 21 day intervals for adriamycin, to 35-100 $mg/m^2$ for etoposide intravenously or orally.

d. Mitotic Inhibitors

Mitotic inhibitors include plant alkaloids and other natural agents that can inhibit either protein synthesis required for cell division or mitosis. They operate during a specific phase during the cell cycle. Mitotic inhibitors comprise docetaxel, etoposide (VP16), paclitaxel, taxol, taxotere, vinblastine, vincristine, and vinorelbine.

e. Nitrosureas

Nitrosureas, like alkylating agents, inhibit DNA repair proteins. They are used to treat non-Hodgkin's lymphomas, multiple myeloma, malignant melanoma, in addition to brain tumors. Examples include carmustine and lomustine.

f. Other Agents

Other agents that may be used include bevacizumab (brand name AVASTIN®), gefitinib (IRESSA®), trastuzumab (HERCEPTIN®), cetuximab (ERBITUX®), panitumumab (VECTIBIX® ), bortezomib (VELCADE®), and GLEEVAC® (imatinib). In addition, growth factor inhibitors and small molecule kinase inhibitors have utility in the present invention as well. All therapies described in Cancer: Principles and Practice of Oncology ($7^{th}$ Ed.), a) 2004, and Clinical Oncology ($3^{rd}$ Ed., 2004) are hereby incorporated by reference. The following additional therapies are encompassed, as well.

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

Immunotherapy, thus, could be used as part of a combined therapy, in conjunction with p53 gene therapy. The general approach for combined therapy is discussed below. Generally, the tumor cell must bear some marker that is amenable to targeting, i.e., is not present on the majority of other cells. Many tumor markers exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155. In addition, p53 itself may be an immunotherapy target. See U.S. Publication 2005/0171045, incorporated herein by reference Tumor Necrosis Factor is a glycoprotein that kills some kinds of cancer cells, activates cytokine production, activates macrophages and endothelial cells, promotes the production of collagen and collagenases, is an inflammatory mediator and also a mediator of septic shock, and promotes catabolism, fever and sleep. Some infectious agents cause tumor regression through the stimulation of TNF production. TNF can be quite toxic when used alone in effective doses, so that the optimal regimens probably will use it in lower doses in combination with other drugs. Its immunosuppressive actions are potentiated by gamma-interferon, so that the combination potentially is dangerous. A hybrid of TNF and interferon-α also has been found to possess anticancer activity.

The use of sex hormones according to the methods described herein in the treatment of cancer. While the methods described herein are not limited to the treatment of a specific cancer, this use of hormones has benefits with respect to cancers of the breast, prostate, and endometrial (lining of the uterus). Examples of these hormones are estrogens, anti-estrogens, progesterones, and androgens.

Corticosteroid hormones are useful in treating some types of cancer (lymphoma, leukemias, and multiple myeloma). Corticosteroid hormones can increase the effectiveness of other chemotherapy agents, and consequently, they are frequently used in combination treatments. Prednisone and dexamethasone are examples of corticosteroid hormones.

3. Radiotherapy

Radiotherapy, also called radiation therapy, is the treatment of cancer and other diseases with ionizing radiation. Ionizing radiation deposits energy that injures or destroys cells in the area being treated by damaging their genetic material, making it impossible for these cells to continue to grow. Although radiation damages both cancer cells and normal cells, the latter are able to repair themselves and function properly. Radiotherapy may be used to treat localized solid tumors, such as cancers of the skin, tongue, larynx, brain, breast, or cervix. It can also be used to treat leukemia and lymphoma (cancers of the blood-forming cells and lymphatic system, respectively).

Radiation therapy used according to the present invention may include, but is not limited to, the use of γ-rays, X-rays, and/or the directed delivery of radioisotopes to tumor cells. Other forms of DNA damaging factors are also contemplated such as microwaves and UV-irradiation. It is most likely that all of these factors effect a broad range of damage on DNA, on the precursors of DNA, on the replication and repair of DNA, and on the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

Radiotherapy may comprise the use of radiolabeled antibodies to deliver doses of radiation directly to the cancer site (radioimmunotherapy). Antibodies are highly specific proteins that are made by the body in response to the presence of antigens (substances recognized as foreign by the immune system). Some tumor cells contain specific antigens that trigger the production of tumor-specific antibodies. Large quantities of these antibodies can be made in the laboratory and attached to radioactive substances (a process known as radiolabeling). Once injected into the body, the antibodies actively seek out the cancer cells, which are destroyed by the cell-killing (cytotoxic) action of the radiation. This approach can minimize the risk of radiation damage to healthy cells.

Conformal radiotherapy uses the same radiotherapy machine, a linear accelerator, as the normal radiotherapy treatment but metal blocks are placed in the path of the x-ray beam to alter its shape to match that of the cancer. This ensures that a higher radiation dose is given to the tumor. Healthy surrounding cells and nearby structures receive a lower dose of radiation, so the possibility of side effects is reduced. A device called a multi-leaf collimator has been developed and can be used as an alternative to the metal blocks. The multi-leaf collimator consists of a number of metal sheets which are fixed to the linear accelerator. Each layer can be adjusted so that the radiotherapy beams can be shaped to the treatment area without the need for metal blocks. Precise positioning of the radiotherapy machine is very important for conformal radiotherapy treatment and a special scanning machine may be used to check the position of your internal organs at the beginning of each treatment.

High-resolution intensity modulated radiotherapy also uses a multi-leaf collimator. During this treatment the layers of the multi-leaf collimator are moved while the treatment is being given. This method is likely to achieve even more precise shaping of the treatment beams and allows the dose of radiotherapy to be constant over the whole treatment area.

Although research studies have shown that conformal radiotherapy and intensity modulated radiotherapy may reduce the side effects of radiotherapy treatment, it is possible that shaping the treatment area so precisely could stop microscopic cancer cells just outside the treatment area being destroyed. This means that the risk of the cancer coming back in the future may be higher with these specialized radiotherapy techniques. Stereotactic radiotherapy is used to treat brain tumors. This technique directs the radiotherapy from many different angles so that the dose going to the tumor is very high and the dose affecting surrounding healthy tissue is very low. Before treatment, several scans are analyzed by computers to ensure that the radiotherapy is precisely targeted, and the patient's head is held still in a specially made frame while receiving radiotherapy. Several doses are given.

Stereotactic radio-surgery (gamma knife) for brain and other tumors does not use a knife, but very precisely targeted beams of gamma radiotherapy from hundreds of different angles. Only one session of radiotherapy, taking about four to five hours, is needed. For this treatment you will have a specially made metal frame attached to your head. Then several scans and x-rays are carried out to find the precise area where the treatment is needed. During the radiotherapy for brain tumors, the patient lies with their head in a large helmet, which has hundreds of holes in it to allow the radiotherapy beams through. Related approaches permit positioning for the treatment of tumors in other areas of the body.

Scientists also are looking for ways to increase the effectiveness of radiation therapy. Two types of investigational drugs are being studied for their effect on cells undergoing radiation. Radiosensitizers make the tumor cells more likely to be damaged, and radioprotectors protect normal tissues from the effects of radiation. Hyperthermia, the use of heat, is also being studied for its effectiveness in sensitizing tissue to radiation.

V. Examples

The following examples are included to further illustrate various aspects of the invention. It should be appreciated by those of skill in the art that the techniques disclosed in the examples that follow represent techniques and/or compositions discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLE 1

ADVEXIN® (Ad5CMV-p53, INGN 201) Treatment Compares Favorably with Overall Survival Benefit Obtained with Approved Therapies SCCHN patients having loco-regional recurrence invariably experience substantial tumor-related morbidity. The need for improved treatments to gain control of regional progression and preserve function in this patient population cannot be over-emphasized. In patients who have failed previous radiation and are deemed unresectable, chemotherapy is accepted as a standard treatment approach. The main goal of recurrent tumor treatment is the palliation of symptoms.

Several chemotherapy and targeted molecular monotherapy regimens have been used in the standard care of recurrent SCCHN with results summarized in comparison with ADVEXIN® (Ad5CMV-p53, INGN 201) the table below. The median overall survivals for ADVEXIN® (Ad5CMV-p53, INGN 201) and standard of care therapies are similar (approximately 5-6 months) and exceed historical median survival rates with no treatment (approximately 3-4 months). (TARCEVA® (erlinotinib) U.S. Product Label, ERBITUX® (cetuximab) U.S. Product Label, 2007).

TABLE 1

Median Overall Survival in Monotherapy Studies in SCCHN (ITT Population)

| Drug | Dose/Cycle | Median Overall Survival(months) |
|---|---|---|
| Methotrexate | 40-60 mg/m² IV | 4.2-5.6 |
| Cisplatin/5FU | 60-100 mg/m²/ 600-1000 mg/m² IV | 5.6-6.4 |
| Carboplatin/5FU | 300-400 mg/m²/ 600-1000 mg/m² IV | 5.0 |
| Docetaxel | 100 mg/m² IV | 6.6 |
| Paclitaxel | 135-175 mg/m² IV | 4.4 |
| Cetuximab | 400 mg/m² IV initially 250 mg/m² IV weekly | 5.8 |
| Erlotinib | 150 mg p.o. | 5.8 |
| Advexin ® Pivotal Trials | >2 × 10$^{11}$-≥2 × 10$^{12}$ vp/day IT | 5.X |
| Advexin ® Pivotal Trials Favorable p53 Biomarker Profiles | >2 × 10$^{11}$-≥2 × 10$^{12}$ vp/day IT | 8.5 |

Importantly, the 8.5 month median survival of ADVEXIN® (Ad5CMV-p53, INGN 201) treated patients with p53 biomarker profiles predictive of ADVEXIN® (Ad5CMV-p53, INGN 201) efficacy compares favorably with the overall survival of conventional treatments (approximately 5 to 6 months). However, the biomarker profiles expected to predict ADVEXIN® (Ad5CMV-p53, INGN 201) efficacy did not predict methotrexate efficacy. In addition, ADVEXIN® (Ad5CMV-p53, INGN 201) has a superior safety profile compared to standard treatments that often compound tumor morbidities. These important advantages of ADVEXIN® (Ad5CMV-p53, INGN 201) therapy are clarified and described in more detail in the sections below.

EXAMPLE 2

ADVEXIN® (Ad5CMV-p53, INGN 201) has a Superior Safety Profile Compared to Standard Therapies The safety data compiled from thousands of administrations in over 400 patients demonstrate that ADVEXIN® (Ad5CMV-p53, INGN 201) is a very well tolerated anticancer treatment and most adverse events are local in nature, self-limiting, and/or amenable to supportive care treatment. The side-effect profile is different from that of systemic chemotherapies and monoclonal antibody treatments for which the adverse events often can be dose-limiting and could potentially develop into more life-threatening sequelae than the local, and often self-limiting events observed with ADVEXIN® (Ad5CMV-p53, INGN 201) therapy. ADVEXIN® (Ad5CMV-p53, INGN 201) was proven to be safe in both males and females and across a wide age range of doses. No clinically significant differences in the ADVEXIN® (Ad5CMV-p53, INGN 201) adverse event profile were noted for gender or age.

The ADVEXIN® (Ad5CMV-p53, INGN 201)Advexin® related serious adverse event rate was very low. For SCCHN patients treated with ADVEXIN® (Ad5CMV-p53, INGN 201), the most frequently reported adverse event was fever (2.9% of all SCCHN patients). For patients treated on the Phase III SCCHN study, ADVEXIN® (Ad5CMV-p53, INGN 201) related serious adverse events included dyspnea (6.6%) and fever (4.9%). The most frequently reported Grade 3 or 4 events for ADVEXIN® (Ad5CMV-p53, INGN 201). SCCHN patients, regardless of causality, were injection site pain and general pain. In the Phase III study, ADVEXIN® (Ad5CMV-p53, INGN 201) Grade 3 or 4 events were generally related to the local administration of ADVEXIN® (Ad5CMV-p53, INGN 201) injection (injection site pain), and these events were often self-limiting and/or amenable to prophylactic local anesthetic infiltration into the site prior to injection, as well as the use of non-steroidal anti-inflammatory and analgesic over-the-counter medications. The incidence of Grade 3 or 4 laboratory changes for ADVEXIN® (Ad5CMV-p53, INGN 201) -treated patients was also low. A total of 49 (18.9%) of patients treated in all ADVEXIN® (Ad5CMV-p53, INGN 201) SCCHN studies reported a Grade 3 or 4 laboratory change from baseline.

In the same study, more methotrexate patients reported Grade 3 or 4 events that were related to systemic methotrexate administration (stomatitis, pneumonia, leucopenia). The systemic adverse events associated with methotrexate treatment may lead to potentially life-threatening sequelae and are potentially more dangerous than the local, and often self-limiting events observed with ADVEXIN® (Ad5CMV-p53, INGN 201) therapy. In addition, as expected for the methotrexate patients treated in the Phase III SCCHN study, a higher incidence of Grade 3 or 4 laboratory events was seen (39.5%) than for ADVEXIN® (Ad5CMV-p53, INGN 201) -treated patients in the same study (19.2%). These events included leukopenia (12.1% of methotrexate patients), neutropenia (12.1%) and lymphopenia (25.6%). For methotrexate patients on the Phase III study, higher incidences of stomatitis, nausea, pneumonia, paresthesia, leucopenia and neutropenia were noted relative to ADVEXIN® (Ad5CMV-p53, INGN 201). The higher rates of stomatitis and nausea associated with methotrexate therapy may have compounded tumor morbidities leading to poorer nutritional intake for these patients and more body weight loss was noted over time for methotrexate patients than for ADVEXIN® (Ad5CMV-p53, INGN 201) patients treated on the Phase III SCCHN study.

Importantly, the systemic adverse events and laboratory abnormalities known to be associated with the use of methotrexate therapy, are potentially more dangerous and life-threatening sequelae than the local, and often self-limiting events observed with ADVEXIN® (Ad5CMV-p53, INGN 201) therapy. In this regard, no patients died due to ADVEXIN® (Ad5CMV-p53, INGN 201) treatment, however, in the Phase III recurrent SCCHN study, one death, due to leukopenia, was attributed to methotrexate. Furthermore, patients on the methotrexate arm of this study were allowed to dose reduce for toxicity, which likely prevented an even higher incidence of individual serious adverse events for methotrexate patients.

ADVEXIN® (Ad5CMV-p53, INGN 201) administered IT did not exacerbate the toxicities of commonly administered chemotherapy agents (docetaxel, doxorubicin or cisplatin) or radiation therapy when given concomitantly for the treatment of "other" tumor types, including locally-advanced breast cancer, prostate cancer, colorectal cancer (CRC), or advanced non-small cell lung cancer (NSCLC). Safety data provided for patients who received radio- or chemotherapy concurrently with ADVEXIN® (Ad5CMV-p53, INGN 201) demonstrated that ADVEXIN® (Ad5CMV-p53, INGN 201) could be combined with these treatment modalities with an acceptable safety profile. Importantly, no exacerbation of the toxicities of these commonly used agents was observed when they were administered in combination with ADVEXIN® (Ad5CMV-p53, INGN 201).

In conclusion, the very favorable clinical safety profile indicates that ADVEXIN® (Ad5CMV-p53, INGN 201) is a highly safe and well-tolerated therapy when administered IT at a dose of $2 \times 10^{12}$ virus particles to patients with recurrent or refractory SCCHN. ADVEXIN® (Ad5CMV-p53, INGN 201) adverse events were often self-limiting and/or amenable to prophylactic local anesthetic treatment, as well as the use of non-steroidal anti-inflammatory and analgesic over-the-counter medications. This well-tolerated safety profile contrasts with the systemic adverse events known to be associated with conventional recurrent SCCHN systemic therapies that can potentially develop into more life-threatening sequelae than the local, and often self-limiting events observed with ADVEXIN® (Ad5CMV-p53, INGN 201) treatment.

EXAMPLE 3

ADVEXIN® (Ad5CMV-p53, INGN 201) Responders have Statistically Significant Increased 3Survival in Recurrent SCCHN Patients Refractory to Approved Treatments Tumor Growth Control Response is Correlated with Statistically Significant Increased Survival Following ADVEXIN® (Ad5CMV-p53, INGN 201) Therapy. Concordant with the findings of Lara et al. (2008), ADVEXIN® (Ad5CMV-p53, INGN 201) therapy in the ITT populations of both T301 and T201 pivotal trials resulted in highly significant increased survival for patients with tumor growth control (CR+PR+SD) responses compared to non-responders in recurrent SCCHN patients who were refractory to other therapies.

In the ADVEXIN® (Ad5CMV-p53, INGN 201) Phase 3 pivotal trial T301, there was a statistically significant increase in survival for patients with TGC responses compared to non-responders (median survival TGC responders 7.6 months vs. non-responders 2.9 months, p=0.0002). These results are depicted in the Kaplan-Meier analysis in FIG. 5.

Similar results were observed in the ADVEXIN® (Ad5CMV-p53, INGN 201) pivotal trial T201 and there was also a statistically significant increase in survival for patients with TGC responses compared to non-responders (median survival TGC responders 6.7 months vs. non-responders 3.6 months, p=0.0269). These results are shown in the Kaplan-Meier analysis in FIG. 6.

Similar analysis of the combined T301 and T201 pivotal clinical trials ITT patient population comprised of 175 ADVEXIN® (Ad5CMV-p53, INGN 201) -treated patients revealed a highly statistically significant increase in survival for the TGC responders compared to non-responders (median survival TGC responders 7.0 months vs. non-responders 3.0 months, p<0.0001). These findings are shown in the Kaplan-Meier analysis in FIG. 7.

Table 2 summarizes the results of these analyses and provides the corresponding data for patients treated with methotrexate in the pivotal Phase 3 T301 study. The methotrexate treated patients also showed an increase in median survival for the TGC responders (7.5 months) compared to non-responders (3.8 months) but the difference was not statistically significant by logrank analysis (p=0.1560). These data clearly indicate a statistically significant survival benefit for patients who achieved a TGC response following ADVEXIN® (Ad5CMV-p53, INGN 201) therapy. This important efficacy result was demonstrated with high statistical significance in two independent, randomized controlled trials of ADVEXIN® (Ad5CMV-p53, INGN 201) therapy in late stage, recurrent SCCHN patients with limited alternative treatment options.

TABLE 2

Correlation of Tumor Growth Control with Survival in Recurrent
SCCHN-ITT Populations Treated with Advexin ®

| Trial Arm | No. of Patients | % Tumor Growth Control | Median Survival (months) (95% CI) | | p Value (Log Rank) |
|---|---|---|---|---|---|
| | | | Responders | Non-Responders | |
| Advexin T301 | 63 | 57.1 | 7.6 | 2.9 | 0.0002 |
| Advexin T201 | 112 | 61.6 | 6.7 | 3.6 | 0.0269 |
| Advexin T301 + T201 | 175 | 60.0 | 7.0 | 3.0 | <0.0001 |
| Methotrexate | 60 | 53.3 | 7.5 | 3.8 | 0.1560 |

Analysis of the correlation of increased survival with tumor responses defined by the Choi criteria (2007) (reduction in tumor size of .gtoreq.10%) also demonstrated a highly statistically significant increase in survival for the responders compared to non-responders in the combined T301 and T201 pivotal clinical trials ITT patient population comprised of 175 ADVEXIN® (Ad5CMV-p53, INGN 201) -treated patients (median survival responders ≥10% tumor reduction 11.2 months vs. non-responders 5.1 months, p=0.0010). These findings are shown in the Kaplan-Meier analysis in FIG. 8.

Conventional definitions of tumor response (.gtoreq.50% reduction in tumor size) also demonstrated a highly statistically significant increase in survival for the responders compared to non-responders in the combined T301 and T201 pivotal clinical trials ITT (N=175) ADVEXIN® (Ad5CMV-p53, INGN 201) treated patients. The median survival for responders with >50% tumor reduction was 41.0 months vs. 5.8 months for non-responders, p=0.0049) (FIG. 9).

As shown in Table 3, similar correlations between tumor responses defined by tumor reductions of >10% and >50% were also observed for the ITT population treated with methotrexate. The percentage of patients with TGC responses was similar for both ADVEXIN® (Ad5CMV-p53, INGN 201) and methotrexate-treated populations (ADVEXIN® (Ad5CMV-p53, INGN 201) =60.0% vs. methotrexate=53.3%). As expected from their known mechanisms of action, a higher proportion of the TGC responders in the ADVEXIN® (Ad5CMV-p53, INGN 201) population had cell cycle arrest/senescence responses while the methotrexate population had a higher proportion of apoptotic responses with reductions in tumor size. Interestingly, ADVEXIN® (Ad5CMV-p53, INGN 201) -treated patients with apoptotic tumor responses resulting in .gtoreq.50% reduction in tumor size had a remarkable median survival of 41.0 months compared to 14.4 months for methotrexate treated patients with similar reductions in tumor size.

TABLE 3

Correlation of Tumor Response with Survival
in Recurrent SCCHN-ITT Populations

| Population/Response | No. of Patients | % Tumor Response | Median Survival (months) (95% CI) | | p Value (Log Rank) |
|---|---|---|---|---|---|
| | | | Responders | Non-Responders | |
| Advexin T301 + T201 TGC | 175 | 60.0 | 7.0 | 3.0 | <0.0001 |
| Methotrexate TGC | 60 | 53.3 | 7.5 | 3.8 | 0.1560 |
| Advexin T301 + T201 ≥10% | 175 | 10.3 | 11.2 | 5.1 | 0.0010 |
| Methotrexate ≥10% | 60 | 18.3 | 11.9 | 4.3 | 0.0594 |
| Advexin T301 + T201 ≥50% | 175 | 4.0 | 41.0 | 5.8 | 0.0049 |
| Methotrexate ≥50% | 60 | 11.7 | 14.4 | 4.6 | 0.0397 |

Overall, these data provide substantial evidence of efficacy for both ADVEXIN® (Ad5CMV-p53, INGN 201) and methotrexate in patients with recurrent SCCHN. Tumor responses for both agents defined by a variety of criteria clearly demonstrate a statistically significant increased survival for responding patients compared to non-responders. Spontaneous remissions do not occur in recurrent SCCHN and the reductions in tumor size observed in these populations were therefore due to these therapeutic agents. Consistent with the important principles demonstrated by Lara et al. (2007) and Choi et al. (2007), tumor responses for both agents defined by tumor growth control or reductions in tumor size.gtoreq.10% were more sensitive predictors of increased survival compared to conventional.gtoreq.50% tumor size reduction criteria.

It is important to realize that with respect to the unmet medical needs of recurrent SCCHN patients, identifying additional agents with efficacy is critical as treatment failure with existing therapies is nearly universal. Comparisons of relative efficacy between these agents is a secondary issue that may impact the sequence in which these agents are administered. Additional factors important in the selection of agents for therapy are potential toxicities and it has been clearly demonstrated that the safety profile of ADVEXIN® (Ad5CMV-p53, INGN 201) has advantages compared to traditional therapies. Another determinant in selecting the most appropriate therapies for recurrent SCCHN patients are biomarkers that may predict therapeutic efficacy of available treatments. As described below, p53 biomarker profiles that predict ADVEXIN® (Ad5CMV-p53, INGN 201) efficacy and indicate that patients benefiting from ADVEXIN® (Ad5CMV-p53, INGN 201) and methotrexate have different molecular profiles. These findings have important implications for guiding individual patient treatment with ADVEXIN® (Ad5CMV-p53, INGN 201) and methotrexate.

EXAMPLE 4

Biomarkers Based on ADVEXIN® (Ad5CMV-p53, INGN 201) Mechanism of Action Predict ADVEXIN® (Ad5CMV-p53, INGN 201) Efficacy and Identify Patients Most Likely to Benefit from ADVEXIN® (Ad5CMV-p53, INGN 201) Treatment with Increased Tumor Responses and Survival, but do not Predict Efficacy of other Treatments The FDA's Critical Path Initiative and the U.S. Department of Health and Human Services Oncology Biomarker Qualification Initiative have encouraged the identification of novel clinical and molecular biomarkers predictive of therapeutic efficacy to guide the most appropriate application of new therapies and facilitate drug approvals. Pursuit of these initiatives has resulted in the identification of p53 Biomarker Profiles Predictive of ADVEXIN® (Ad5CMV-p53, INGN 201) Efficacy in recurrent squamous cell carcinoma of the head and neck that are described in this report.

Biomarker profiles predictive of ADVEXIN® (Ad5CMV-p53, INGN 201) efficacy are based upon p53 gene configurations assessed by sequence analyses and their level of protein expression determined by immunohistochemistry. These p53 biomarker assessments were first described in the results of the Phase 1 ADVEXIN® (Ad5CMV-p53, INGN 201) clinical trial INT-002 in SCCHN patients performed and reported by Clayman et al. (1998) and were subsequently incorporated into pivotal clinical trial protocols and statistical analysis plans. The p53 profiles predictive of ADVEXIN® (Ad5CMV-p53, INGN 201) efficacy are consistent with known mechanisms of tumor p53 inactivation and ADVEXIN® (Ad5CMV-p53, INGN 201) activity as described below.

FIG. 9 depicts the two major mechanisms of tumor p53 inactivation and the p53 gene sequencing and immunohistochemistry profiles associated with these different types of p53 abnormalities. Inactivation of p53 by gene mutation is associated with a mutated p53 gene sequence resulting in an abnormal p53 protein that may be expressed at either high or low levels as determined by immunohistochemistry (FIG. 10, left panel). Alternatively, when p53 is inactivated by upregulation of the p53 inhibitors mdm-2 or mdm-4 (FIG. 10, right panel), the p53 gene sequence is wild-type and the resulting normal p53 protein may be expressed at either high or low level levels as detected by immunohistochemistry.

p53 Biomarker Profiles Favorable for ADVEXIN® (Ad5CMV-p53, INGN 201) Efficacy. In tumors with wild-type p53 gene sequences, p53 is typically inactivated by upregulation of the p53 inhibitors mdm-2 and/or mdm-4 (Valentin-Vega et al., 2007). These findings have been confirmed for the recurrent SCCHN patients in ADVEXIN® (Ad5CMV-p53, INGN 201) pivotal trials, with 93% (27/29 evaluated patients) having wild-type p53 gene sequences also having upregulation of either mdm-2 and/or mdm-4. p53 biomarker profiles with wild-type p53 sequences were found to be favorable for ADVEXIN® (Ad5CMV-p53, INGN 201) efficacy by Clayman et al. (1998). As diagrammed in FIG. 11, the combination of normal p53 delivered by ADVEXIN® (Ad5CMV-p53, INGN 201) and endogenous wild-type p53 produced by the tumor is sufficient to overcome the inhibition of mdm-2/mdm-4.

Another major mechanism of tumor p53 inactivation is through mutation of the p53 gene resulting in the loss of p53 function. As shown in FIG. 12, the vast majority of p53 mutations (>80%) occur in the DNA binding domain of the p53 molecule.

Functional p53 is a tetramer requiring the combination of four normal p53 molecules that are joined through their tetramerization regions. The tetramer normally binds to DNA and subsequently regulates the expression of other genes that are responsible for tumor suppression. As depicted in the FIG. 13 below, p53 with mutations in the DNA binding domain will not be functional as these tetramers will not be able to bind to DNA.

The p53 biomarker profile with mutated p53 sequence and low level p53 protein expression by immunohistochemistry (.ltoreq.50% positive tumor cells) was found to be favorable for ADVEXIN® (Ad5CMV-p53, INGN 201) efficacy. As illustrated in the FIG. 14 below, when tumors have low level expression of mutated p53, ADVEXIN® (Ad5CMV-p53, INGN 201) can provide sufficient normal p53 to form functional tetramers and restore p53 tumor suppression.

p53 Biomarker Profiles Unfavorable for ADVEXIN® (Ad5CMV-p53, INGN 201) Efficacy. In contrast, p53 biomarker profiles with mutated p53 sequence and high level p53 protein expression by immunohistochemistry (>50% positive tumor cells) are unfavorable for ADVEXIN® (Ad5CMV-p53, INGN 201) efficacy. This observation is consistent with the association of these biomarker profiles with the dominant-negative effect of high level expression of p53 proteins with DNA binding domain mutations that are known to inhibit normal p53 delivered by ADVEXIN® (Ad5CMV-p53, INGN 201). As depicted in FIG. 15, p53 with mutations in the DNA binding domain can inhibit normal p53 through the formation of non-functional heterotetramers that are a mixture of normal and mutated p53 molecules. This is the basis for the "dominant-negative" effect of p53 mutations in the DNA binding domain when they are expressed at high levels (>50% positive tumor cells by immunohistochemistry).

Hence, normal p53 delivered by ADVEXIN® (Ad5CMV-p53, INGN 201) is inhibited in tumors with high level expression of p53 protein mutated in the DNA binding domain. These "dominant-negative" p53 biomarker profiles characterized by p53 sequence mutations in the DNA binding domain and high p53 protein levels by immunohistology are expected to be unfavorable for ADVEXIN® (Ad5CMV-p53, INGN 201) efficacy.

In summary, the presence of wild-type p53 gene configurations and the absence of high level protein expression of dominant-negative p53 mutations are expected to be predictive of ADVEXIN® (Ad5CMV-p53, INGN 201) efficacy. These favorable and unfavorable P53 biomarker profiles are consistent with known mechanisms of ADVEXIN® (Ad5CMV-p53, INGN 201) action and tumor p53 inactivation as described above. Table 4 summarizes the characteristics of the favorable and unfavorable p53 biomarker profiles for ADVEXIN® (Ad5CMV-p53, INGN 201) efficacy defined by combined p53 sequencing and immunohistochemistry evaluations. The nature of the associated p53 proteins and the mechanisms of ADVEXIN® (Ad5CMV-p53, INGN 201) efficacy and p53 inactivation are also listed.

TABLE 4

Characteristics of Favorable and Unfavorable p53 Biomarker Profiles for Advexin ® Efficacy

| Advexin efficacy | p53 Biomarker Profiles | | p53 Protein Type | p53 Protein Level | Mechanisms of Action |
|---|---|---|---|---|---|
| | p53 Sequence | p53 Immunohistology | | | |
| Favorable | Wild type | Negative | Normal | Low | Advexin reverses p53 inhibitors (mdm-2/4) |
| Favorable | Wild type | Positive | Normal | High | |
| Favorable | Mutated | Negative | Abnormal | Low | Advexin restores mutated p53 function |
| Unfavorable | Mutated | Positive | Abnormal | High | Advexin inhibited by dominant negative effects |

ADVEXIN® (Ad5CMV-p53, INGN 201) mechanism of action is targeted to restoration of p53 function and p53 biomarker profiles predictive of ADVEXIN® (Ad5CMV-p53, INGN 201) efficacy were shown to identify patients with increased tumor responses and survival in pivotal trial data analyses. Biomarker profiles predictive of ADVEXIN® (Ad5CMV-p53, INGN 201) efficacy were based upon the assessment of p53 gene configuration by sequence analyses and their level of protein expression determined by immunohistochemistry. The presence of wild-type p53 gene configurations and the absence of high level protein expression of dominant-negative p53 mutations were predictive of ADVEXIN® (Ad5CMV-p53, INGN 201) efficacy. FIG. 16 depicts these favorable and unfavorable p53 profiles based upon p53 sequence and immunohistochemistry evaluations.

Approximately 75% of recurrent SCCHN patients have p53 biomarker profiles favorable for ADVEXIN® (Ad5CMV-p53, INGN 201) efficacy while 25% have unfavorable profiles. As described above, there is a statistically significant association of tumor response with increased survival in patients treated with ADVEXIN® (Ad5CMV-p53, INGN 201). Based upon the known mechanisms of tumor p53 inactivation and the above-noted ADVEXIN® Ad5CMV, INGN 201). efficacy, the inventors would expect that patients with favorable p53 biomarker profiles would demonstrate statistically significant associations with TGC responses and increased median survival compared to patients with unfavorable p53 profiles. These are precisely the results that were observed with very high statistical significance as described below.

Importantly, these p53 biomarker profiles did not predict outcomes following methotrexate therapy indicating that they were not merely prognostic markers for any form of treatment. Furthermore, the molecular profiles of patients benefiting from ADVEXIN® (Ad5CMV-p53, INGN 201) and methotrexate therapy were found to be different and complementary having important implications for guiding the therapy of recurrent SCCHN patients with these agents.

p53 Biomarker Profiles for ADVEXIN® (Ad5CMV-p53, INGN 201) Efficacy Predict Tumor Growth Control in Recurrent SCCHN. As shown in Table 5, there was a highly statistically significant correlation between p53 profiles favorable for ADVEXIN® (Ad5CMV-p53, INGN 201) efficacy and TGC responses following ADVEXIN® (Ad5CMV-p53, INGN 201) treatment. A very high proportion of ADVEXIN® (Ad5CMV-p53, INGN 201) -treated patients with p53 profiles favorable for ADVEXIN® (Ad5CMV-p53, INGN 201) efficacy had TGC responses (79%) compared to only 25% of patients with unfavorable profiles for ADVEXIN® (Ad5CMV-p53, INGN 201) efficacy (p=0.004 by Fisher's Exact Test).

TABLE 5 p53 Biomarker Profiles for Advexin ® Efficacy Predict Tumor Growth Control in Recurrent SCCHN Cancer INT-002, T201 and T301 Advexin Treated Patients with p53 Profile Data-Preliminary Analysis

| p53 Profile | Tumor Growth Control |
|---|---|
| Favorable | 45/57 (79%) |
| Unfavorable | 2/8 (25%) |

Fisher's exact text p value = 0.004

Comparison of the p53 mutational status in TGC responders to ADVEXIN® (Ad5CMV-p53, INGN 201) and methotrexate treatment revealed differences in their molecular features indicating beneficial effects in different populations of recurrent SCCHN patients. As shown in Table 6, methotrexate TGC responders were associated with mutated p53 while the opposite was observed for ADVEXIN® (Ad5CMV-p53, INGN 201) responders who tended to have a higher proportion of wild-type p53 profiles.

TABLE 6

Tumor Growth Control Occurs in Different Patient Populations Following Advexin ® and Methotrexate (MTX) Treatment T301A Advexin Treated Patients N = 31

| p53 Gene Status | Tumor Growth Control |
|---|---|
| Wild Type | 12/14 (86%) |
| Mutated | 9/17 (53%) |

Fisher's exact text p value = 0.0580

T301B Methotrexate Treated Patients N- 35

| p53 Gene Status | Tumor Growth Control |
|---|---|
| Wild Type | 11/20 (55%) |
| Mutated | 13/15 (87%) |

Fisher's exact text p value = 0.0493 p53 Profiles Favorable and Unfavorable for ADVEXIN® (Ad5CMV-p53, INGN 201) Efficacy Predict ADVEXIN® (Ad5CMV-p53, INGN 201) Survival Benefit in Recurrent SCCHN but Do Not Predict Methotrexate Efficacy. As depicted in FIG. 17, the T301 phase 3 pivotal trial p53 biomarker analyses revealed a statistically significant increased survival following ADVEXIN® (Ad5CMV-p53, INGN 201) therapy for patients with p53 profiles favorable for ADVEXIN® (Ad5CMV-p53, INGN 201) efficacy compared to those with unfavorable profiles (median survival 7.2 vs. 2.7 months; log rank test p<0.0001).

Similar results were obtained when biomarker survival data from pivotal trials T201 and T301 were combined as shown in FIG. 18. The combined T301 and T201 pivotal trials p53 biomarker analyses revealed a statistically significant increased survival following ADVEXIN® (Ad5CMV-p53, INGN 201) therapy for patients with p53 profiles favorable for ADVEXIN® (Ad5CMV-p53, INGN 201) efficacy compared to those with unfavorable profiles (median survival 8.5 vs. 2.8 months; log rank test p=0.0017). The findings indicate that these p53 biomarker profiles can predict patients most likely to benefit from ADVEXIN® (Ad5CMV-p53, INGN 201) therapy. These favorable and unfavorable p53 biomarker profiles are consistent with known mechanisms of ADVEXIN® (Ad5CMV-p53, INGN 201) action and tumor p53 inactivation described above.

Importantly, these p53 biomarker profiles did not predict methotrexate efficacy in the phase 3 pivotal T301 trial as shown in FIG. 19. These results indicate that the predictive p53 biomarker profiles of ADVEXIN® (Ad5CMV-p53, INGN 201) efficacy were not merely general prognostic profiles that would predict outcomes with any therapy but rather were specific for ADVEXIN® (Ad5CMV-p53, INGN 201) outcomes. This result is not surprising as these predictive biomarkers were developed based upon known mechanisms of p53 inactivation and ADVEXIN® (Ad5CMV-p53, INGN 201efficacy.

Implications of p53 Biomarker Profiles for the Management of Recurrent SCCHN Patients with ADVEXIN® (Ad5CMV-p53, INGN 201)Advexin® and Methotrexate Therapies. The results of these p53 biomarker analyses have important implications for the management of recurrent SCCHN patients with ADVEXIN® (Ad5CMV-p53, INGN 201) and methotrexate who are refractory to cisplatin and taxanes. As shown in FIG. 20, there was a highly statistically significant difference in survival outcomes by log rank analysis (p=0.0003) for patients treated with ADVEXIN® (Ad5CMV-p53, INGN 201) or methotrexate based upon profiles that were favorable or unfavorable for ADVEXIN® (Ad5CMV-p53, INGN 201) efficacy.

The median survivals for these populations ranged from 7.2 months for patients with profiles predictive of ADVEXIN® (Ad5CMV-p53, INGN 201) efficacy who were treated with ADVEXIN® (Ad5CMV-p53, INGN 201) to only 2.7 months for patients with profiles unfavorable for ADVEXIN® (Ad5CMV-p53, INGN 201) efficacy who received ADVEXIN® (Ad5CMV-p53, INGN 201) treatment. Intermediate median survival times were observed for the patients with profiles favorable and unfavorable for ADVEXIN® (Ad5CMV-p53, INGN 201) efficacy who were treated with methotrexate (4.3 and 6.0 months respectively). As noted above, there was no statistical difference in median survival for the methotrexate treated patients based upon p53 profiles predictive of ADVEXIN® (Ad5CMV-p53, INGN 201) efficacy.

Hence, the efficacy and safety data reviewed above supports the use of ADVEXIN® (Ad5CMV-p53, INGN 201) for the treatment of recurrent SCCHN patients with p53 profiles favorable for ADVEXIN® (Ad5CMV-p53, INGN 201) efficacy who are refractory to cisplatin and taxanes. Recurrent SCCHN patients with TGC responses following ADVEXIN® (Ad5CMV-p53, INGN 201) treatment have statistically significant increased survival and p53 biomarker profiles predictive of ADVEXIN® (Ad5CMV-p53, INGN 201) efficacy are associated with TGC responses with high statistical significance. Furthermore, patients with p53 biomarker profiles favorable for ADVEXIN® (Ad5CMV-p53, INGN 201) efficacy have statistically significant increased survival compared to unfavorable p53 profiles in response to ADVEXIN® (Ad5CMV-p53, INGN 201) treatment. These biomarkers do not predict methotrexate efficacy and indicate that ADVEXIN® (Ad5CMV-p53, INGN 201) and methotrexate provide TGC and increased survival in complementary subpopulations of recurrent SCCHN. The superior safety profile of ADVEXIN® (Ad5CMV-p53, INGN 201) compared to methotrexate further supports selection of ADVEXIN® (Ad5CMV-p53, INGN 201) for the treatment of recurrent SCCHN patients with p53 profiles favorable for ADVEXIN® (Ad5CMV-p53, INGN 201) efficacy.

Conversely, the same data analyses indicate that patients with p53 biomarker profiles unfavorable for ADVEXIN® (Ad5CMV-p53, INGN 201) efficacy are very unlikely to benefit from ADVEXIN® (Ad5CMV-p53, INGN 201) treatment and that alternative therapy should be considered for these patients. FIG. 21 indicates that methotrexate is efficacious in patients with p53 biomarker profiles unfavorable for ADVEXIN® (Ad5CMV-p53, INGN 201) efficacy with a statistically significant increased survival following methotrexate compared to ADVEXIN® (Ad5CMV-p53, INGN 201) therapy for patients with p53 profiles unfavorable for ADVEXIN® (Ad5CMV-p53, INGN 201) (median survival 6.0 vs. 2.7 months; log rank test p=0.0112).

This result is consistent with the differences in the p53 molecular profiles of TGC responders to ADVEXIN® (Ad5CMV-p53, INGN 201) and methotrexate described above indicating that methotrexate responders were associated with mutated p53 profiles and ADVEXIN® (Ad5CMV-p53, INGN 201) responders with wild-type p53 genotypes. Overall, the tumor response, survival and p53 biomarker analyses indicate that both ADVEXIN® (Ad5CMV-p53, INGN 201) and methotrexate demonstrate substantial evidence of efficacy in recurrent SCCHN patients refractory to cisplatin and taxanes and that appropriate treatment with ADVEXIN® (Ad5CMV-p53, INGN 201) or methotrexate may be guided by determination of p53 biomarker profiles favorable and unfavorable for ADVEXIN® (Ad5CMV-p53, INGN 201) efficacy.

* * *

All of the compositions and/or methods disclosed and claimed herein can be made and executed without undue experimentation in light of the present disclosure. While the compositions and methods of this invention have been described in terms of particular embodiments, it will be apparent to those of skill in the art that variations may be applied to the compositions and/or methods in the steps or in the sequence of steps of the method described herein without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

VI. References

The following references, to the extent that they provide exemplary procedural or other details supplementary to those set forth herein, are specifically incorporated herein by reference:

U.S. Pat. No. 4,415,723
U.S. Pat. No. 4,458,066
U.S. Pat. No. 4,659,774
U.S. Pat. No. 4,682,195
U.S. Pat. No. 4,683,202
U.S. Pat. No. 4,797,368
U.S. Pat. No. 4,816,571
U.S. Pat. No. 4,879,236
U.S. Pat. No. 4,946,778
U.S. Pat. No. 4,959,463
U.S. Pat. No. 5,139,941
U.S. Pat. No. 5,141,813
U.S. Pat. No. 5,264,566
U.S. Pat. No. 5,302,523
U.S. Pat. No. 5,322,783
U.S. Pat. No. 5,354,855
U.S. Pat. No. 5,384,253
U.S. Pat. No. 5,428,148
U.S. Pat. No. 5,464,765
U.S. Pat. No. 5,538,877
U.S. Pat. No. 5,538,880
U.S. Pat. No. 5,550,318
U.S. Pat. No. 5,554,744
U.S. Pat. No. 5,563,055
U.S. Pat. No. 5,574,146
U.S. Pat. No. 5,580,859
U.S. Pat. No. 5,589,466
U.S. Pat. No. 5,602,244
U.S. Pat. No. 5,610,042
U.S. Pat. No. 5,645,897
U.S. Pat. No. 5,656,610
U.S. Pat. No. 5,670,488
U.S. Pat. No. 5,672,344
U.S. Pat. No. 5,677,178
U.S. Pat. No. 5,702,932
U.S. Pat. No. 5,705,629
U.S. Pat. No. 5,736,524
U.S. Pat. No. 5,747,469
U.S. Pat. No. 5,747,869
U.S. Pat. No. 5,780,448
U.S. Pat. No. 5,789,215
U.S. Pat. No. 5,795,715
U.S. Pat. No. 5,871,986
U.S. Pat. No. 5,879,703
U.S. Pat. No. 5,888,773
U.S. Pat. No. 5,889,136
U.S. Pat. No. 5,932,210
U.S. Pat. No. 5,945,100
U.S. Pat. No. 5,981,225
U.S. Pat. No. 5,981,274
U.S. Pat. No. 5,994,136
U.S. Pat. No. 5,994,624
U.S. Pat. No. 6,013,516
U.S. Pat. No. 6,017,524
U.S. Pat. No. 6,069,134
U.S. Pat. No. 6,136,594
U.S. Pat. No. 6,143,290
U.S. Pat. No. 6,210,939
U.S. Pat. No. 6,296,845
U.S. Pat. No. 6,410,010
U.S. Pat. No. 6,511,184
U.S. Pat. No. 6,511,847
U.S. Pat. No. 6,555,376
U.S. Pat. No. 6,627,190
U.S. Pat. No. 6,797,704
U.S. Patent App. 2005/0171045
U.S. Patent App. 2004/0213764
U.S. Patent App. 2002/0077313
U.S. Patent App. 2002/0028785
U.S. Patent App. 2002/0006914
U.S. Patent App. 20050143336
U.S. Patent App. 20050196343
U.S. Patent App. 20050203047
U.S. Patent App. 20050260276
U.S. Application Ser. No. 09/351,778
Ahomadegbe et al., *Oncogene*, 10(6):1217-1227, 1995.
Aksentijevich et al., *Hum. Gene Ther.*, 7(9):1111-1122, 1996.
Argiris et al., *Cancer*, 101(10):2222-2229, 2004.
Ausubel et al., In: *Current Protocols in Molecular Biology*, John, Wiley & Sons, Inc, New York, 1996.
Baichwal and Sugden, In: *Gene Transfer*, Kucherlapati (Ed.), NY, Plenum Press, 117-148, 1986.
Bakhshi et al., *Cell*, 41(3):899-906, 1985.
Bargonetti et al., *Cell*, 65(6):1083-1091, 1991.
Batterson and Roizman, *J. Virol.*, 46(2):371-377, 1983.
Bernstein et al., *Nature*, 409:363-366, 2001.
Bittner et al., *Methods in Enzymol*, 153:516-544, 1987.
Blomer et al., *J. Virol.*, 71(9):6641-6649, 1997.
Bosher and Labouesse, *Nat. Cell. Biol.*, 2:E31-E36, 2000.
Brennecke et al., *Cell*, 113:25-36, 2003.
Cancer: Principles and Practice of Oncology (7th Ed.), 2004.
Cancer: Principles and Practice of Oncology Single Volume (CD-ROM), Devita et al. (Eds.), Lippencott, 2001.
Cariello, *Human Genetics*, 42:726, 1988.
Casey et al., *Oncogene*, 6(10):1791-1797, 1991.
Chen and Okayama, *Mol. Cell Biol.*, 7(8):2745-2752, 1987.
Clayman et al., *Cancer Res.*, 55(14):1-6, 1995.
Clayman et al., *Clin. Cancer Res.*, 5(7):1715-1722, 1999.
Clayman et al., *J. Clin. Oncol.*, 16(6):2221-2232, 1998.
Cleary and Sklar, *Proc. Natl. Acad. Sci. USA*, (21):7439-7443, 1985.
Cleary et al., *J. Exp. Med.*, 164(1):315-320, 1986.
Clinical Oncology (3rd Ed.), Martin (Eds.), 2004.
Cook et al., *Cell*, 27:487-496, 1981.
Cotton et al., *Proc. Natl. Acad. Sci. USA*, 85: 4397, 1988.
Couch et al., *Am. Rev. Resp. Dis.*, 88:394-403, 1963.
Dameron et al. *Science* 265:1582-1584, 1994.
De Vries et al., *Proc Natl Acad Sci USA.* 99(5):2948-53, 2002.
DeLuca et al., *J. Virol.*, 56(2):558-570, 1985.
Doench et al., *Genes Dev.*, 17:438-442, 2003.
Edelman and Nemunaitis, *Curr. Opin. Mol. Ther.*, 5(6):611-617, 2003.
Elbashir et al., *EMBO J.*, 20:6877-6888, 2001.
Elbashir et al., *Genes Dev.*, 5(2):188-200, 2001.
Elroy-Stein et al., *Proc. Natl. Acad. Sci. USA*, 86(16):6126-6130, 1989.
EP 266 032
Erbitux®U.S. Product Label, 2007
Fechheimer, et al., *Proc Natl. Acad. Sci. USA*, 84:8463-8467, 1987.
Felgner et al., *Proc. Natl. Acad. Sci. USA*, 84(21):7413-7417, 1987.
Fields and Jang, *Science*, 249(4972):1046-1049, 1990.
Fire et al., *Nature*, 391(6669):806-811, 1998.
Fitzgibbon et al., *Leukemia*, 21(7):1514-20, 2007.
Flotho et al., *Oncogene*, 26(39):5816-21, 2007.
Forster and Symons, *Cell*, 49(2):211-220, 1987.

Fraley et al., *Proc. Natl. Acad. Sci. USA*, 76:3348-3352, 1979.
Froehler et al., *Nucleic Acids Res.*, 14(13):5399-5407, 1986.
Gabizon et al., *Cancer Res.*, 50(19):6371-6378, 1990.
Gallo et al., *Cancer*, 75(8):2037-2044, 1995.
Ganly et al., *Br. J. Cancer*, 82(2):392-398, 2000.
Geisler et al., *Clinical Cancer Research*, 8:3445-3453, 2002.
George et al., *J. Clinical Oncology*, 25(34):5352-5358, 2007.
George et al., *PLoS ONE*, 2(2):e255, 2007.
Gerlach et al., *Nature (London)*, 328:802-805, 1987.
Ghosh and Bachhawat, In: *Liver Diseases, Targeted Diagnosis and Therapy Using Specific Receptors and Ligands*, Wu et al. (Eds.), Marcel Dekker, NY, 87-104, 1991.
Glorioso et al., *Mol. Biotechnol.*, 4(1):87-99, 1995.
Gomez-Foix et al., *J. Biol. Chem.*, 267:25129-25134, 1992.
Gopal, *Mol. Cell Biol.*, 5:1188-1190, 1985.
Graham and Prevec, *Biotechnology*, 20:363-390, 1992.
Graham and Van Der Eb, *Virology*, 52:456-467, 1973.
Graham et al, *J. General Virology*, 36:59-74, 1977.
Grishok et al., *Cell*, 106:23-34, 2001.
Grishok et al., *Science*, 287:2494-2497, 2000.
Grunhaus and Horwitz, *Seminar in Virology*, 3:237-252, 1992.
Harland and Weintraub, *J. Cell Biol.*, 101(3):1094-1099, 1985.
Hartwell and Kastan, *Science*, 266(5192):1821-1828, 1994.
Herz and Gerard, *Proc. Natl. Acad. Sci. USA*, 90:2812-2816, 1993.
Herz and Roizman, *Cell*, 33(1):145-151, 1983.
Holland and Holland, *J Biol Chem*, 255(6):2596-605, 1980.
Hollstein et al., *Science*, 253(5015):49-53, 1991.
Honess and Roizman, *J. Virol.*, 14(1):8-19, 1974.
Honess and Roizman, *J. Virol.*, 16(5):1308-1326, 1975.
Hutvgner and Zamore, *Science*, 297:2056-2060, 2002.
Hutvgner et al., *Science*, 293:834-838, 2001.
Joyce, *Nature*, 338:217-244, 1989.
Kaeppler et al., *Plant Cell Reports*, 9:415-418, 1990.
Kaneda et al., *Science*, 243:375-378, 1989.
Kastan et al., *Cancer Metastasis Rev.*, 14(1):3-15, 1995.
Kato et al, *J. Biol. Chem.*, 266:3361-3364, 1991.
Kawamata et al., *Blood*, 111(2):776-84, 2008.
Kerr et al., *Br. J. Cancer*, 26(4):239-257, 1972.
Ketting et al., *Genes Dev.*, 15(20):2654-2659, 2001.
Ketting et al., *Cell*, 99(2):133-141, 1999.
Kim and Cook, *Proc. Natl. Acad. Sci. USA*, 84(24):8788-8792, 1987.
Knight and Bass, *Science*, 293:2269-2271, 2001.
Kyzas et al., *J. Natl. Cancer Inst.*, 97(14):1043-1055, 2005.
Ladner et al. *Cancer Res.* 60:3493-503, 2000.
Lai et al., *Genes, Chromosones, Cancer,* 46:532-542, 2007.
Lara et al., *Journal of Clinical Oncology*, 26: 463-467, 2008.
Laughlin et al., *J. Virol.*, 60(2):515-524, 1986.
Le Gal La Salle et al., *Science*, 259:988-990, 1993.
Lebkowski et al., *Mol. Cell. Biol.*, 8(10):3988-3996, 1988.
Lee et al., *Cell*, 75:843-854, 1993.
Levrero et al., *Gene*, 101:195-202, 1991.
Lin and Avery, *Nature*, 402:128-129, 1999.
Lindbjerg et al., *Carcinogenesis*, 28(1):38-48, 2007.
Lips et al., *Cancer Res.*, 65(22):10188-10191, 2005.
Mann et al., *Cell*, 33:153-159, 1983.
Martin et al., *Nature*, 345(6277):739-743, 1990.
Matsumura et al., *Oncology*, 53(4):308-312, 1996.
McKaig et al., *Head Neck*, 20(3):250-265, 1998.
McLaughlin et al., *J. Virol.*, 62(6):1963-1973, 1988.
McPake et al., *Cancer Res.*, 59:4247-4251, 1999
Melcher et al., *Cytogenet Genome Res.*, 118(2-4):214-21, 2007.
Mercer, *Critic. Rev. Eukar. Gene Express.* 2:251-263, 1992.
Meyers et al., *Science*, 230:1242, 1985.
Michel and Westhof, *J. Mol. Biol.*, 216:585-610, 1990.
Mietz et al., *EMBO J.*, 11(13):5013-5020, 1992.
Miller et al., *Am. J. Clin. Oncol.*, 15(3):216-221, 1992.
Montgomery et al., *Proc. Natl. Acad. Sci. USA*, 95:15502-15507, 1998.
Mourelatos et al., *Genes. Dev.*, 16:720-728, 2002.
Mulder et al., *Br. J. Cancer*, 71(6):1257-1262, 1995.
Muzyczka, *Curr. Topics Microbiol. Immunol.*, 158:97-129, 1992.
Nabel et al., *Science*, 244(4910):1342-1344, 1989.
Naldini et al., *Science*, 272(5259):263-267, 1996.
Nemunaitis et al., *J. Clin. Oncol.*, 18(3):609-622, 2000.
Nemunaitis et al., *N. Engl. J. Med.*, 324(25):1773-1778, 1991.
Nicolas and Rubenstein, In: *Vectors: A survey of molecular cloning vectors and their uses*, Rodriguez and Denhardt (Eds.), Stoneham: Butterworth, 494-513, 1988.
Nicolau and Sene, *Biochim. Biophys. Acta*, 721:185-190, 1982.
Nicolau et al., *Methods Enzymol.*, 149:157-176, 1987.
Olivier et al., *Clin. Cancer Res.*, 12(4):1157-1167, 2006.
Paskind et al., *Virology*, 67:242-248, 1975.
PCT Appln. WO 00/44914
PCT Appln. WO 01/36646
PCT Appln. WO 01/68836
PCT Appln. WO 02/08436
PCT Appln. WO 02/31168
PCT Appln. WO 02/85287
PCT Appln. WO 03/33029
PCT Appln. WO 94/09699
PCT Appln. WO 95/06128
PCT Appln. WO 98/07408
PCT Appln. WO 99/18933
PCT Appln. WO 99/32619
Peitjean et al., *Oncogene*, 26:2157-2165, 2007.
Peng, *Hum. Gene Ther.*, 16(9):1016-1027, 2005.
Philip et al., *J. Biol. Chem.*, 268(22):16087-16090, 1993.
Pivot et al., *Oncology*, 61(3):197-204, 2001.
Poeta et al., *NE J. Medicine*, 357(25):2552-2561, 2007.
Post et al., *Cell*, 24(2):555-65, 1981.
Potter et al., *Proc. Natl. Acad. Sci. USA*, 81:7161-7165, 1984.
Purdie et al., *Genes Chromosomes Cancer*, 46(7):661-9, 2007.
Racher et al., *Biotechnology Techniques*, 9:169-174, 1995.
Ragot et al., *Nature*, 361:647-650, 1993.
Recondo et al., *Laryngoscope*, 101(5):494-501, 1991.
Reinhart et al., *Nature*, 403:901-906, 2000.
Reinhold-Hurek and Shub, *Nature*, 357:173-176, 1992.
Renan, *Radiother. Oncol.*, 19:197-218, 1990.
Resnick and Inga, *Proc. Natl. Acad. Sci. USA*, 100(17):9934-9939, 2003.
Rich et al., *Hum. Gene Ther.*, 4:461-476, 1993.
Ridgeway, In: *Vectors: A survey of molecular cloning vectors and their uses*, Rodriguez and Denhardt (Eds.), Stoneham: Butterworth, 467-492, 1988.
Rippe et al., *Mol. Cell Biol.*, 10:689-695, 1990.
Rosenfeld et al., *Science*, 252:431-434, 1991.
Rosenfeld, et al., *Cell*, 68:143-155, 1992.
Ross, et al., *1: Clin. Cancer Res.*, 13(16):4777-85, 2007.
Roth et al., *Nat Med.*, 2(9):985-991, 1996.
Roux et al., *Proc. Natl. Acad. Sci. USA*, 86:9079-9083, 1989.
Saiki et al., *Science*, 239:487, 1988.

Sambrook et al., In: *Molecular cloning*, Cold Spring Harbor Laboratory Press, Cold Spring Harbor, N.Y., 2001.
Sarkis et al., *J. Clin. Oncol.*, 13(6):1384-1390, 1995.
Sarver et al., *Science*, 247:1222-1225, 1990.
Sauter et al., *J. Surg. Oncol.*, 58(4):269-273, 1995.
Saxena et al., *J. Biol. Chem.*, 278:44312-44319, 2003.
Scanlon et al., *Proc. Natl. Acad. Sci. USA*, 88:10591-10595, 1991.
Sharp and Zamore, *Science*, 287:2431-2433, 2000.
Sharp, *Genes Dev.*, 13:139-141, 1999.
Shaw et al., *Proc. Natl. Acad. Sci. USA*, 89(10):4495-4499, 1992.
Shenk et al., *Proc. Natl. Acad. Sci. USA*, 72:989, 1975.
Smith and Moss, *Gene*, 25(1):21-28, 1983.
Solodin et al., *Biochemistry*, 34(41):13537-13544, 1995.
Souissi et al., *Nat. Rev. Cancer*, 6:83-90, 2006.
Stenmark-Askmalm et al., *Br. J. Cancer*, 72(3):715-719, 1995.
Stratford-Perricaudet and Perricaudet, In: *Human Gene Transfer*, Eds, Cohen-Haguenauer and Boiron, John Libbey Eurotext, France, 51-61, 1991.
Stratford-Perricaudet et al., *Hum. Gene. Ther.*, 1:241-256, 1990.
Swisher et al., *J. Natl. Cancer Inst.*, 91(9):763-771, 1999.
Tabara et al., *Cell*, 99(2):123-132, 1999.
Tarceva® U.S. Product Label
Temin, In: *Gene Transfer*, Kucherlapati (Ed.), NY, Plenum Press, 149-188, 1986.
Templeton et al., *Nat. Biotechnol.*, 15(7):647-652, 1997.
Thierry et al., *Proc. Natl. Acad. Sci. USA*, 92(21):9742-9746, 1995.
Top et al., *J. Infect. Dis.*, 124:155-160, 1971.
Tratschin et al., *Mol. Cell. Biol.*, 4:2072-2081, 1984.
Trkova et al., *Cancer Gene. Cytogen.*, 145:60-64, 2003.
Tsujimoto and Croce, *Proc. Natl. Acad. Sci. USA*, 83(14):5214-5218, 1986.
Tsujimoto et al., *Science*, 228(4706):1440-1443, 1985.
Tsukamoto et al., *Nat. Genet.*, 9(3):243-248, 1995.
Tur-Kaspa et al., *Mol. Cell Biol.*, 6:716-718, 1986.
Valentin-Vega et al., *Hum. Pathol.*, 38(10):1553-1562, 2007.
van Beers et al., *Br. J. Cancer*, 94(2), 333-337, 2006.
Weinberg, *Science*, 254(5035):1138-1146, 1991.
Wilcock and Lane, *Nature*, 349(6308):429-431, 1991.
Wilder et al., *Cancer Res.*, 59:410-413, 1999a.
Wilder et al., *Gene Therapy*, 6:57-62, 1999b.
Wilson et al., *Science*, 244:1344-1346, 1989.
Wincott et al., *Nucleic Acids Res.*, 23(14):2677-2684, 1995.
Winter et al., *Proc. Natl. Acad. Sci. USA*, 82:7575, 1985.
Wong et al., *Gene*, 10:87-94, 1980.
Wu and Wu, *Biochemistry*, 27:887-892, 1988.
Wu and Wu, *J. Biol. Chem.*, 262:4429-4432, 1987.
Xu et al., *Curr. Biol.*, 13:790-795, 2003.
Yamamoto et al., 1: *Am J Hum Genet.* 81(1):114-26, 2007.
Yang and Huang, *Gene Therapy*, 4 (9):950-960, 1997.
Yonish-Rouach et al., *Nature*, 352(6333):345-347, 1991.
Zakut-Houri et al., *EMBO J.*, 4(5):1251-1255, 1985.
Zeng et al., *Mol. Cell*, 9:1327-1333, 2002.
Zeng et al., *Proc. Natl. Acad. Sci. USA*, 100:9779-9784, 2003.
Zhang et al., *Hum. Gene Ther.*, 6(2):155-164, 1995.
Zhu et al., *Science*, 261(5118):209-211, 1993.
Zufferey et al., *Nat. Biotechnol.*, 15(9):871-875, 1997.

The invention claimed is:

1. A method of treating a subject using p53 gene therapy comprising:
   a) identifying a subject having a tumor, wherein the tumor cells comprise two wild type p53 alleles; and
   b) treating the patient with the p53 gene therapy.

2. A method of treating a subject using p53 gene therapy comprising:
   a) identifying a subject having a tumor, wherein the tumor cells have been first tested and determined not to contain a p53 mutant allele; and
   b) then treating the patient with the p53 gene therapy.

3. The method of claim 1 or 2, wherein the p53 gene of the p53 gene therapy is comprised in a non-viral vector.

4. The method of claim 3, wherein the non-viral vector is entrapped in a lipid vehicle.

5. The method of claim 4, wherein the lipid vehicle is a liposome or a nanoparticle.

6. The method of claim 1 or 2, wherein the p53 gene of the p53 gene therapy is comprised in a viral vector.

7. The method of claim 6, wherein the viral vector is a retroviral vector, an adenoviral vector, an adeno-associated viral vector, a pox viral vector, a polyoma viral vector, a lentiviral vector, or a herpes viral vector.

8. The method of claim 1 or 2, wherein the tumor is a benign tumor growth further defined as is benign prostatic hyperplasia, oral leukoplakia, a colon polyp, an esophageal pre-cancerous growth or a benign lesion.

9. The method of claim 1 or 2, wherein the tumor is a cancer, further defined as an oral cancer, oropharyngeal cancer, nasopharyngeal cancer, respiratory cancer, urogenital cancer, gastrointestinal cancer, central or peripheral nervous system tissue cancer, an endocrine or neuroendocrine cancer or hematopoietic cancer, glioma, sarcoma, carcinoma, lymphoma, melanoma, fibroma, meningioma, brain cancer, oropharyngeal cancer, nasopharyngeal cancer, renal cancer, biliary cancer, pheochromocytoma, pancreatic islet cell cancer, Li-Fraumeni tumors, thyroid cancer, parathyroid cancer, pituitary tumors, adrenal gland tumors, osteogenic sarcoma tumors, multiple neuroendrcine type I and type II tumors, breast cancer, lung cancer, head and neck cancer, prostate cancer, esophageal cancer, tracheal cancer, liver cancer, bladder cancer, stomach cancer, pancreatic cancer, ovarian cancer, uterine cancer, cervical cancer, testicular cancer, colon cancer, rectal cancer or skin cancer.

10. The method of claim 7, wherein the viral vector is an adenoviral vector.

* * * * *